United States Patent
Shoda et al.

(10) Patent No.: US 6,376,546 B1
(45) Date of Patent: Apr. 23, 2002

(54) BIPHENYL-5-ALKANOIC ACID DERIVATIVES AND USE THEREOF

(75) Inventors: Motoshi Shoda; Hiromichi Itoh, both of Shizuoka (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 09/509,683

(22) PCT Filed: Oct. 2, 1998

(86) PCT No.: PCT/JP98/04456

§ 371 Date: Jun. 8, 2000

§ 102(e) Date: Jun. 8, 2000

(87) PCT Pub. No.: WO99/19291

PCT Pub. Date: Apr. 22, 1999

(30) Foreign Application Priority Data

Oct. 14, 1997 (JP) .............................. 9-280814

(51) Int. Cl.[7] .............................. A61K 31/19
(52) U.S. Cl. ................ 514/568; 514/567; 514/532; 514/533; 514/534; 514/539; 514/561; 514/564; 514/570; 562/469; 562/429; 562/435; 562/473; 562/492; 560/21; 560/37; 560/42; 560/51; 560/53; 560/59
(58) Field of Search ................ 514/568, 567, 514/532, 533, 534, 539, 561, 564, 570; 562/469, 429, 435, 438, 451, 465, 473, 492; 560/21, 37, 42, 51, 53, 59, 81, 102

(56) References Cited

U.S. PATENT DOCUMENTS

| | | |
|---|---|---|
| 4,008,323 A | 2/1977 | Cousse et al. |
| 4,058,558 A | 11/1977 | Cousse et al. |
| 4,485,202 A | 11/1984 | Terada et al. |
| 5,136,090 A | 8/1992 | Suzuki et al. |
| 5,155,259 A | 10/1992 | Suzuki et al. |
| 5,232,948 A | 8/1993 | Huang et al. |
| 5,312,960 A | 5/1994 | Kramer et al. |
| 5,380,914 A | 1/1995 | Kramer et al. |
| 5,391,817 A | * 2/1995 | Springer et al. |
| 5,464,809 A | 11/1995 | Kramer et al. |

FOREIGN PATENT DOCUMENTS

| | | |
|---|---|---|
| JP | 50-135050 | 10/1975 |
| JP | 57-35543 | 2/1982 |
| JP | 58-55469 | 4/1983 |
| JP | 4019307 | 12/1991 |
| JP | 4-95025 | 3/1992 |
| JP | 4-95049 | 3/1992 |
| JP | 6-503812 | 4/1994 |

OTHER PUBLICATIONS

"Synthetic Choleretics; II. Phenol Derivatives"; by Robert R. Burtner and John M. Brown, received Aug. 13, 1952, Contribution from the Research Laboratories of G.D. Searle & Co., vol. 75, pp. 2334–2340.

"An approach for General Synthesis of Biphenyl Neolignans by the Reaction of 1–Oxaspiro[4.5]deca–6,9–diene–2,8–dione with the Grignard Reagent and Synthesis of Magnaldehyde B"; Tetsuya Takeya et al., Chem. Pharm. Bull., 35(5), 1755–1761, (1987).

"Synthesis of Biphenyls by Acid–Catalyzed Condensation Reactions of 1–Oxaspiro[4.5]deca–6,9–diene–2,8–dione with Phenols or Phenol–ethers", Tetsuya Takeya et al., Chem. Pharm. Bull., 35 (5), 1762–1769, (1987).

"Synthesis and Antiinflammatory Activity of 4–(p–Biphenylyl)–3–hydroxybutyric Acid and Related Compounds"; D.I. Barron et al., pp. 1139–1144, vol. 11, Nov. 1968.

* cited by examiner

Primary Examiner—Deborah D. Carr
(74) Attorney, Agent, or Firm—Young & Thompson

(57) ABSTRACT

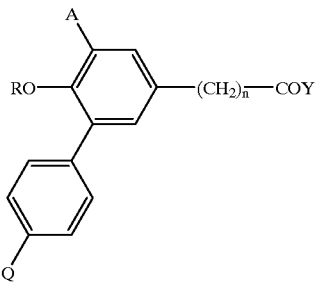

Compounds represented by general formula I or salts thereof, wherein n is an integer of 2 or 3; R represents a straight-chain or branched saturated alkyl group having 4 or 4 carbon atoms, a cyclopentyl group, a cyclohexyl group or the like, Y represents a hydroxyl or amino group, A represents a hydrogen atom, a hydroxyl, methoxy, nitro group or the like, Q represents a hydrogen atom or a hydroxyl or methoxy group. They can be formulated to give pharmaceutical compositions that are effective as prophylactic or therapeutic agents for allergic diseases associated with IgE production inhibitors or IgE antibodies.

6 Claims, No Drawings

BIPHENYL-5-ALKANOIC ACID DERIVATIVES AND USE THEREOF

This application is a 371 of PCT JP/98/04456 Oct. 2, 1998

FILED OF THE INVENTION

This invention relates to novel biphenyl-5-alkanoic acid derivatives or salt thereof and a pharmaceutical composition containing the same as an active ingredient, especially IgE antibody production suppressor and drugs for treatment and prevention of allergic diseases characterized by IgE antibody suppressive action.

PRIOR ARTS

Allergic diseases such as bronchial asthma, allergic rhinitis, atopic dermatitis, allergic conjunctivitis and anaphylaxis are classified into type I allergic reaction. The type I allergic reaction consists of, generally, the following three steps during the process of generation. Namely, these are: (1) the first step: antigen is entered into the body, and immunoglobulin E (IgE) is produced as a result of interaction with antigen-presenting cells such as macrophage, T cells and B cells, then the IgE antibody is bound with receptor on the cell membrane of mast cells and basophils to establish sensitization; (2) the second step: the reentry of antigen results to bind with IgE which is bound with the receptor, to generate degranulation of mast cells or basophils by antigen-antibody reaction to release chemical mediators such as histamine and SRS-A; and (3) the third step: the released chemical mediators induce contraction of the smooth muscle, capillary hyperpermeability and increase in mucous secretion to lead allergic reaction.

As above explained, the type I allergic reaction has known to be induced by IgE antibody production, and, in fact, serum or tissue levels of IgE antibody in patients with the aforementioned allergic diseases showed, in most cases, higher than those of the healthy subjects. Consequently, a compound, which selectively suppresses IgE antibody production, might be a useful agent for causal therapy of allergic diseases, and development of such a compound and its pharmaceutical product has been desired.

The known example of compound, which has similar structure of the compound of the present invention, is, for example, 3-(2-methoxy-1,1'-biphenyl-5-yl)propionic acid (J. Am. Chem. Soc., 75:2334, 1953) as choleretic agent. The said compound has different structure from the compound of the present invention in the ether moiety in phenolic hydroxy group in its structure, and in addition, no information on an action of IgE antibody production is disclosed. The same report discloses 3-(3-phenyl-4-methoxybenzoyl) propionic acid, however the said compound is different from the compound of the present invention in the ether moiety, furthermore a part of an oxo group in methylene moiety between biphenyl moiety and carboxy group is different in each other.

In the reference, Chem. Pharm. Bull. 35(5):1755, 1987, discloses methyl 3-(4'-allyloxy-2-benzyloxy-1,1'-biphenyl-5-yl)propionate is disclosed, however it is different from ether moiety from the compound of the present invention. In addition, the said compound was synthesized as an intermediate of a natural compound magaldehyde and no pharmacological action was disclosed. Further, in the said reference, on page 1762, methyl 3-(2,4'-dihydroxy-1,1'-biphenyl-5-yl)propionate and methyl 3-(4'-allyloxy-2-hydroxy-1,1'-biphenyl-5-yl)propionate were reported, however it was different in its ether moiety from the compound of the present invention, furthermore no pharmacological action has reported.

DE-4019307 and Japanese Patent Unexamined Publication No. Hei 4-230252 disclose methyl 2-methoxyimino-3-(4'-chloro-2-methoxy-1,1'-biphenyl-5-yl)propionate as harmful organisms preventive agent. The said compound is different from the compound of the present invention in the structure on the points having different structure in the ether moiety and having methoxyimino group in methylene moiety between biphenyl moiety and carboxy group. In addition, no action about IgE antibody production is disclosed.

DE-2513157 and Japanese Patent Unexamined Publication No. Sho 50-135050 disclose methyl 4-oxo-4-(2-methoxy-1,1'-biphenyl-5-yl)-2-methylene butyric acid as anti-inflammatory agent. The said compound is different from the compound of the present invention on the point that it has ether moiety and has oxo group and methylene group in the methylene moiety between biphenyl moiety and carboxy group. In addition, no IgE production is disclosed.

In Japanese Patent Unexamined Publication No. Sho 58-55469 describes 3-(3-t-butoxy-2-hydroxy-1,1'-biphenyl-5-yl)propionic acid as a stabilizer for resin. The said compound is different from the compound of the present invention on the point of substituents in the ether moiety and biphenyl moiety. Further, no pharmacological action is disclosed.

J. Med. Chem. 11:1139, 1968, discloses 4-(4-butoxy-1,1'-biphenyl-5-yl)-3-hydroxy butyric acid as anti-inflammatory agent. The said compound is different from the compound of the present invention on the point of position of substituent in ether moiety and having hydroxy group in methylene moiety between biphenyl moiety and carboxy group. Further, no IgE antibody production is disclosed.

In Japanese Patent Unexamined Publications No. Hei 4-95025 and No. Hei 4-95049 disclose biphenyl-5,5'-bis-alkanoic acid derivative as an aldose reductase inhibitor. The said compound is different from the compound of the present invention on the point having alkanoic acid in both of benzene rings in biphenyl moiety. Further, no IgE antibody production is disclosed.

U.S. Pat. No. 5,391,817 and Japanese Patent Unexamined Publication No. Hei 7-223997 disclose biphenyl derivatives as biaryl phospholipase $A_2$ inhibitor. The said compounds are different from the compound of the present invention on the point of ether moiety and no compound of the present invention is included in their claims. Further, no IgE antibody production is disclosed in these patents.

Problems to be Solved by the Invention

An aspect of the present invention is to provide a compound for treatment and prevention of allergic diseases caused by type I allergic reaction, which is suppressed by selectively suppressing IgE antibody production.

Means for Solving the Problems

In order to solve the above problems, we have extensively studied and found that the novel compound biphenyl-5-alkanoic acid derivatives represented by the general formula shown below have selective and superior suppressive action against IgE antibody production, then completed the present invention.

An object of the present invention is to provide a compound of the general formula (I) or salt thereof.

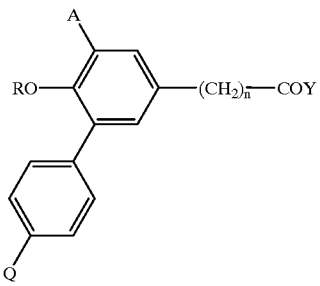

(I)

wherein n is an integer of either 2 or 3, R is straight or branched saturated alkyl of carbon numbers 4 or 5 (a), cyclopentyl, cyclohexyl, cyclopentylmethyl, cyclohexylmethyl or —$(CH_2)_m$W, proviso that saturated alkyl (a) may optionally be substituted by hydroxy, oxo or halogen, m is an integer of 1–3, W is carboxy or —$CONR^1R^2$, in which $R^1$ and $R^2$ are in together or each separately hydrogen or lower alkyl of $C_{1-4}$, Y is hydroxy or amino, A is hydrogen, hydroxy, methoxy, nitro or —NHZ, in which Z is —CO $R^3$ or —$SO_2$ $R^4$, in which $R^3$ is hydrogen, saturated alkyl (b) of $C_{1-4}$ or —$NR^5{}_2$, the saturated alkyl (b) may optionally be substituted by hydroxy or halogen, $R^4$ is saturated alkyl (c) of $C_{1-4}$ or —$NR^6{}_2$, the saturated alkyl (c) may optionally be substituted by halogen, $R^5$ and $R^6$ are hydrogen or lower alkyl of $C_{1-4}$, and Q is hydrogen, hydroxy or methoxy [hereinafter sometimes designates as "the compound (I)"].

Another object of the present invention is to provide a drug comprising the compound of the above general formula (I) or pharmacologically acceptable salt thereof as an active ingredient.

In the above general formula (I), n is defined as any one of integer of 2 or 3. No effect is obtained wherein n is 1 or 4. Since it is extremely characteristics when n is 2 or 3, ethylene in 2 or trimethylene in 3 is preferable.

A group R is defined as straight or branched saturated alkyl of carbon numbers 4 or 5 (a), cyclopentyl, cyclohexyl, cyclopentylmethyl, cyclohexylmethyl or —$(CH_2)_m$W, proviso that saturated alkyl (a) may optionally be substituted by hydroxy, oxo or halogen, and m is an integer of 1–3, and W is carboxy or —$CONR^1R^2$, in which $R^1$ and $R^2$ are in together or each separately hydrogen or lower alkyl of $C_{1-4}$.

In a group R, examples of straight or branched saturated alkyl of carbon numbers 4 or 5 are n-butyl, isobutyl, 1-methylpropyl, t-butyl, n-pentyl, isopentyl, 2-methylbutyl and 1-methylbutyl. Among them, n-butyl, isobutyl, n-pentyl, and isopentyl are preferable, and n-butyl is most preferable.

In a group R, examples of straight or branched saturated alkyl of carbon numbers 4 or 5 substituted by hydroxy are straight or branched saturated alkyl of carbon numbers 4 or 5 substituted by a hydroxy in any carbons except for carbon constituting ether bonding in the saturated alkyl. Examples are 2-hydroxybutyl, 3-hydroxybutyl, 4-hydroxybutyl, 2-hydroxypentyl, 3-hydroxypentyl, 4-hydroxypentyl and 5-hydroxypentyl. Among them, 2-hydroxybutyl and 3-hydroxybutyl are preferable.

In a group R, examples of straight or branched saturated alkyl of carbon numbers 4 or 5 substituted by oxo are straight or branched saturated alkyl of carbon numbers 4 or 5 substituted by an oxo in a secondary carbon except for carbon constituting ether bonding in the saturated alkyl. Examples are 2-oxobutyl and 2-oxopentyl, and 2-oxobutyl is a preferable example.

A "halogen" in a group R of straight or branched saturated alkyl of carbon numbers 4 or 5 substituted by halogen means fluorine, chlorine, bromine or iodine. Examples of straight or branched saturated alkyl of carbon numbers 4 or 5 substituted by halogen are straight or branched saturated alkyl of carbon numbers 4 or 5 substituted by 1–3 halogens in any carbons except for carbon constituting ether bonding in the saturated alkyl. Examples are 2-chlorobutyl, 3-chlorobutyl, 2-chloropentyl, 3-chloropentyl, 4-chloropentyl, 5-chloropentyl, 4-bromobutyl and 4,4,4-trifluorobutyl. 3-chlorobutyl and 4,4,4-trifluorobutyl are preferable.

In a group R, cyclopentyl, cyclohexyl, cyclopentylmethyl and cyclohexylmethyl are preferable, and cyclohexylmethyl is most preferable.

In a group R, wherein R is —$(CH_2)_m$W, m is preferably integers of 1–3, especially methylene, in which m is 1, is preferable. W is most preferably a carboxy. When W is —$CONR^1R^2$, examples of $R^1$ and $R^2$ are hydrogen, methyl, ethyl, n-propyl, isopropyl, n-butyl, isobutyl and t-butyl, and $R^1$ and $R^2$ can be the same or different. Among them, hydrogen, methyl and ethyl are preferable, and hydrogen is most preferable. Consequently, when W is —$CONR^1R^2$, preferable examples are carbamoyl, N-methylcarbamoyl, N-ethylcarbamoyl, N,N-dimethylcarbamoyl and N,N-diethylcarbamoyl, and among them, carbamoyl is most preferable.

Examples of —$(CH_2)_m$W are carboxymethyl, 2-carboxyethyl, 3-carboxypropyl, carbamoylmethyl, 2-carbamoylethyl, 3-carbamoylpropyl, (N-methylcarbamoyl)methyl, (N-ethylcarbamoyl)methyl, (N,N-dimethylcarbamoyl)methyl, (N,N-diethylcarbamoyl)methyl, 2-(N,N-dimethylcarbamoyl)ethyl and 3-(N,N-dimethylcarbamoyl)propyl. Among them, carboxymethyl, 2-carboxyethyl, 3-carboxypropyl, carbamoylmethyl, and (N,N-dimethylcarbamoyl)methyl are preferable, especially carboxymethyl and carbamoylmethyl are most preferable.

When R contains asymmetric carbon, in case of one asymmetric carbon, two optical isomers, and in case of two asymmetric carbons, four optical isomers can be possible. Any these isomers are preferable examples. In a mixture thereof, it is preferable for easier production.

A group Y is defined as hydroxy or amino, and any substituents are preferable.

A group A is hydrogen, hydroxy, methoxy, nitro or —NHZ, in which Z is —$COR^3$ or —$SO_2$ $R^4$, in which $R^3$ is hydrogen, saturated alkyl (b) of $C_{1-4}$ or —$NR^5{}_2$. The saturated alkyl (b) may optionally be substituted by hydroxy or halogen. $R^5$ is hydrogen or lower alkyl of $C_{1-4}$. $R^4$ is saturated alkyl (c) of $C_{1-4}$ or —$NR^6{}_2$. The saturated alkyl (c) may optionally be substituted by halogen. $R^6$ is hydrogen or lower alkyl of $C_4$. Any substituents are preferable for the group A, and especially hydrogen is most preferable substituent.

When the group A is —NHZ and Z is —$COR^3$, a group $R^3$ is, for example, preferably hydrogen. When the group $R^3$ is saturated alkyl (b) of $C_{14}$, the saturated alkyl (b) may optionally have branched chain, and examples thereof are methyl, ethyl, n-propyl, isopropyl, n-butyl, isobutyl and t-butyl. Among them, methyl and ethyl are preferable, and methyl is most preferable. In the saturated alkyl (b), any carbons in the saturated alkyl may optionally be substituted by one hydrogen. Examples thereof are hydroxymethyl and 2-hydroxyethyl, and hydroxymethyl is preferable. In the saturated alkyl (b), any carbons in the saturated alkyl may optionally be substituted by 1–3 halogens. Examples thereof are chloromethyl and trifluoromethyl, and chloromethyl is preferable. When $R^3$ is —$NR^5{}_2$, the group $R^5$ is hydrogen, methyl, ethyl, n-propyl, isopropyl, n-butyl, isobutyl and t-butyl. Among them, hydrogen and methyl are preferable, and hydrogen is most preferable.

Examples of —$NR^5{}_2$ are amino, dimethylamino and diethylamino. Among them, amino and dimethylamino are preferable, and amino is most preferable. Consequently, preferable examples of —$COR^3$ are formyl, acetyl, propionyl, hydroxyacetyl, chloroacetyl, carbamoyl and N,N-dimethylcarbamoyl. Among them, formyl, acetyl and carbamoyl are most preferable examples.

When a group A is —NHZ and the group Z is —$SO_2R^4$, in which $R^4$ is saturated alkyl (c) of $C_{1-4}$, the saturated alkyl (c) may optionally have branched chain. Examples thereof are methyl, ethyl, n-propyl, isopropyl, n-butyl, isobutyl and t-butyl, and among them, methyl is most preferable. In the saturated alkyl (c), any carbons in the saturated alkyl may optionally be substituted by 1–3 halogens, and examples thereof are chloromethyl and trifluoromethyl. When $R^4$ is —$NR^6{}_2$, the group $R^6$ is hydrogen, methyl, ethyl, n-propyl, isopropyl, n-butyl, isobutyl and t-butyl, and methyl are preferable.

Examples of —$NR^6{}_2$ are amino, dimethylamino and diethylamino, and among them, dimethylamino is preferable. Consequently, examples of the group —$SO_2R^4$ are methylsulfonyl, ethylsulfonyl, chloromethylsulfonyl, trifluoromethylsulfonyl, sulfamoyl and N,N-dimethylsulfamoyl. Among them, preferable examples are methylsulfonyl and N,N-dimethylsulfamoyl and methylsulfonyl is most preferable.

Preferable examples of —NHZ in the group A are formylamino, acetylamino, propionylamino, hydroxyacetylamino, chloroacetylamino, carbamoylamino, N,N-dimethylcarbamoylamino, methylsulfonylamino and N,N-dimethylsulfamoylamino. Among them, formylamino, acetylamino, carbamoylamino and methylsulfonylamino are most preferable.

A group Q is defined as hydrogen, hydroxy or methoxy, and any substituents are most preferable.

Preferable scope of the compound of the present invention is a compound in the general formula (I), wherein n is integer of 2 or 3, R is n-butyl, isobutyl, n-pentyl, isopentyl, cyclopentyl, cyclohexyl, cyclopentylmethyl, cyclohexylmethyl, 2-hydroxybutyl, 3-hydroxybutyl, 2-oxobutyl, 3-chlorobutyl, 4,4,4-trifluorobutyl, carboxymethyl, 2-carboxyethyl, 3-carboxypropyl, carbamoylmethyl or (N,N-dimethylcarbamoyl)methyl, Y is hydroxy or amino, A is hydrogen, hydroxy, methoxy, nitro, formylamino, acetylamino, propionylamino, hydroxyacetylamino, chloroacetylamino, carbamoylamino, N,N-dimethylcarbamoylamino, methylsulfonylamino, or N,N-dimethylsulfamoylamino, and Q is hydrogen, hydroxy or methoxy, or salt thereof.

More preferable scope of the compound of the present invention includes a compound in the general formula (I), wherein n is integer of 2 or 3, R is n-butyl, cyclohexylmethyl, carboxymethyl or carbamoylmethyl, Y is hydroxy or amino, A is hydrogen, formylamino, acetylamino, carbamoylamino or methylsulfonylamino, and Q is hydrogen, hydroxy or methoxy, or salt thereof.

The most preferable scope of the compound of the present invention includes a compound in the general formula (I), wherein n is 2, R is cyclohexylmethyl, Y is hydroxy or amino, A is hydrogen, formylamino, acetylamino, carbamoylamino or methylsulfonylamino, and Q is hydrogen, hydroxy or methoxy, or salt thereof.

Concrete examples of the compound of the present invention (I) can be mentioned as follows.

3-(2-butoxy-1,1'-biphenyl-5-yl)propionic acid;
3-(2-isobutoxy-1,1'-biphenyl-5-yl)propionic acid;
3-(2-pentyloxy-1,1'-biphenyl-5-yl)propionic acid;
3-(2-cyclopentyloxy-1,1'-biphenyl-5-yl)propionic acid;
3-(2-cyclohexyloxy-1,1'-biphenyl-5-yl)propionic acid;
3-(2-cyclopentylmethyloxy-1,1'-biphenyl-5-yl)propionic acid;
3-(2-cyclohexylmethyloxy-1,1'-biphenyl-5-yl)propionic acid;
3-[2-(2-hydroxybutyloxy)-1,1'-biphenyl-5-yl]propionic acid;
3-[2-(2-oxobutyloxy)-1,1'-biphenyl-5-yl]propionic acid;
3-(2-carboxymethyloxy-1,1'-biphenyl-5-yl)propionic acid;
3-(2-carbamoylmethyloxy-1,1'-biphenyl-5-yl)propionic acid;
3-(2-butoxy-3-nitro-1,1'-biphenyl-5-yl)propionic acid;
3-(3-acetylamino-2-butoxy-1,1'-biphenyl-5-yl)propionic acid;
3-(2-butoxy-3-methylsulfonylamino-1,1'-biphenyl-5-yl)propionic acid;
3-(3-acetylamino-2-cyclohexylmethyloxy-1,1'-biphenyl-5-yl)propionic acid;
3-(2-cyclohexylmethyloxy-3-methylsulfonylamino-1,1'-biphenyl-5-yl)propionic acid;
3-(2-cyclohexylmethyloxy-3-hydroxyacetylamino-1,1'-biphenyl-5-yl)propionic acid;
3-[2-cyclohexylmethyloxy-3-(N,N-dimethylcarbamoylamino)-1,1'-biphenyl-5-yl]propionic acid;
3-[2-cyclohexylmethyloxy-3-(N,N-dimethylsulfamoylamino)-1,1'-biphenyl-5-yl]propionic acid;
3-(3-carbamoylamino-2-cyclohexylmethyloxy-1,1'-biphenyl-5-yl)propionic acid;
3-(2-cyclohexylmethyloxy-3-methoxy-1,1'-biphenyl-5-yl)propionic acid;
3-(2-cyclohexylmethyloxy-3-hydroxy-1,1'-biphenyl-5-yl)propionic acid;
3-(2-cyclohexylmethyloxy-4'-hydroxy-1,1'-biphenyl-5-yl)propionic acid;
3-(2-cyclohexylmethyloxy-4'-methoxy-1,1'-biphenyl-5-yl)propionic acid;
3-(2-cyclohexylmethyloxy-4,1'-biphenyl-5-yl)propionamide;
4-(2-butoxy-1,1'-biphenyl-5-yl)butyric acid;
4-(2-isobutoxy-1,1'-biphenyl-5-yl)butyric acid;
4-[2-(-methylpropyloxy)-1,1'-biphenyl-5-yl]butyric acid;
4-(2-pentyloxy-1,1'-biphenyl-5-yl)butyric acid;
4-[2-(1-methylbutyloxy)-1,1'-biphenyl-5-yl]butyric acid;
4-[2-(2-methylbutyloxy)-1,1'-biphenyl-5-yl]butyric acid;
4-(2-isopentyloxy-1,1'-biphenyl-5-yl)butyric acid;
4-(2-cyclopentyloxy-1,1'-biphenyl-5-yl)butyric acid;
4-(2-cyclohexyloxy-1,1'-biphenyl-5-yl)butyric acid;
4-(2-cyclopentylmethyloxy-1,1'-biphenyl-5-yl)butyric acid;
4-(2-cyclohexylmethyloxy-1,1'-biphenyl -5-yl)butyric acid;
4-[2-(4-hydroxybutyloxy)-1,1'-biphenyl-5-yl]butyric acid;
4-[2-(3-hydroxybutyloxy)-1,1'-biphenyl-5-yl]butyric acid;
4-[2-(2-hydroxybutyloxy)-1,1'-biphenyl-5-yl]butyric acid;
4-(2-carboxymethyloxy-1,1'-biphenyl-5-yl)butyric acid;
4-[2-(2-carboxyethyloxy)-1,1'-biphenyl-5-yl]butyric acid;
4-[2-(3-carboxypropyloxy)-1,1'-biphenyl-5-yl]butyric acid;
4-(2-carbamoylmethyloxy-1,1'-biphenyl-5-yl)butyric acid;
4-[2-(N,N-dimethylcarbamoylmethyloxy)-1,1'-biphenyl-5-yl]butyric acid;
4-[2-(N,N-diethylcarbamoylmethyloxy)-1,1'-biphenyl-5-yl]butyric acid;
4-(2-butoxy-3-nitro-1,1'-biphenyl-5-yl)butyric acid;
4-(2-butoxy-3-formylamino-1,1'-biphenyl-5-yl)butyric acid;

4-(3-acetylamino-2-butoxy-1,1'-biphenyl-5-yl)butyric acid;
4-(2-butoxy-3-methylsulfonylamino-1,1'-biphenyl-5-yl)butyric acid;
4-(2-butoxy-3-methoxy-1,1'-biphenyl-5-yl)butyric acid;
4-(2-butoxy-1,1'-biphenyl-5-yl)butyramide;
4-(2-carbamoylmethyloxy-1,1'-biphenyl-5-yl)butyramide;
4-[2-(3-carbamoylpropyloxy)-1,1'-biphenyl-5-yl]butyramide;
4-[2-(4-chlorobutyloxy)-1,1'-biphenyl-5-yl]butyric acid;
4-[2-(3-chlorobutyloxy)-1,1'-biphenyl-5-yl]butyric acid;
4-[2-(4-bromobutyloxy)-1,1'-biphenyl-5-yl]butyric acid; and
4-[2-(4,4,4-trifluorobutyloxy)-1,1'-biphenyl-5-yl]butyric acid;

Among them, compounds having optical isomer are as follows.
3-[2-(2-hydroxybutyloxy)-1,1'-biphenyl-5-yl]propionic acid;
4-[2-(1-methylpropyloxy)-1,1'-biphenyl-5-yl]butyric acid;
4-[2-(1-methylbutyloxy)-1,1'-biphenyl-5-yl]butyric acid;
4-[2-(2-methylbutyloxy)-1,1'-biphenyl-5-yl]butyric acid;
4-[2-(3-hydroxybutyloxy)-1,1'-biphenyl-5-yl]butyric acid;
4-[2-(2-hydroxybutyloxy)-1,1'-biphenyl-5-yl]butyric acid; and
4-[2-(3-chlorobutyloxy)-1,1'-biphenyl-5-yl]butyric acid.

These optical isomers and mixtures thereof are preferable examples of the compound (I).

The specifically preferable compounds (I) of the present invention can be listed as follows.
3-(2-butoxy-1,1'-biphenyl-5-yl)propionic acid;
3-(2-cyclohexylmethyloxy-1,1'-biphenyl-5-yl)propionic acid;
3-(2-carboxymethyloxy-1,1'-biphenyl-5-yl)propionic acid,
3-(2-carbamnoylmethyloxy-1,1'-biphenyl-5-yl)propionic acid;
3-(3-acetylamino-2-butyloxy-1,1'-biphenyl-5-yl)propionic acid;
3-(2-butoxy-3-methylsulfonylamino-1,1'-biphenyl-5-yl)propionic acid;
3-(3-acetylamino-2-cyclohexylmethyloxy-1,1'-biphenyl-5-yl)propionic acid;
3-(2-cyclohexylmethyloxy-3-methylsulfonylamino-1,1'-biphenyl-5-yl)propionic acid;
3-(3-carbamoylamino-2-cyclohexylmethyloxy-1,1'-biphenyl-5-yl)propionic acid;
3-(2-cyclohexylmethyloxy-4'-hydroxy-1,1'-biphenyl-5-yl)propionic acid;
3-(2-cyclohexylmethyloxy-4'-methoxy-1,1'-biphenyl-5-yl)propionic acid;
3-(2-cyclohexylmethyloxy-1,1'-biphenyl-5-yl)propionamide;
4-(2-butoxy-1,1'-biphenyl-5-yl)butyric acid;
4-(2-cyclohexyloxy-1,1'-biphenyl-5-yl)butyric acid;
4-(2-carboxymethyloxy-1,1'-biphenyl-5-yl)butyric acid;
4-(2-carbamoylmethyloxy-1,1'-biphenyl-5-yl)butyric acid;
4-(2-butoxy-3-formylamino-1,1'-biphenyl-5-yl)butyric acid;
4-(3-acetylamino-2-butoxy-1,1'-biphenyl-5-yl)butyric acid
4-(2-butoxy-3-methylsulfonylamino-1,1'-biphenyl-5-yl)butyric acid;
4-(2-butoxy-1,1'-biphenyl-5-yl)butyramide; and
4-(2-carbamnoylmethyloxy-1,1'-biphenyl-5-yl)butyramide.

Salt of the compound (I) is preferably pharmaceutically acceptable salt, and in case that Y is hydroxy; W is carboxy; or A or Q is phenolic hydroxy, it means salt of any one or more of these groups. One to four alkaline salts can be formed depending on numbers of acidic groups, and examples of salt are salt with inorganic base such as sodium and ammonium, or organic base such as triethylamine.

The compound (I) of the present invention can be produced, for example, by the following various methods.

[The Process for Production 1]
(Process a)

A Compound of the General Formula II, which is the compound (I) of the present invention, wherein Y is hydroxy;

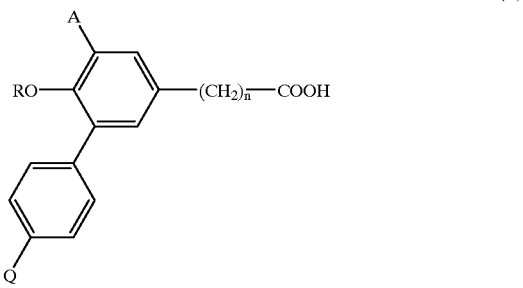

wherein n, R, A and Q have the same meaning hereinbefore, [hereinafter designates as simply "the compound (II)"]can be produced by hydrolyzing a compound of the general formula (III) [hereinafter designates as simply "the compound (III)"]

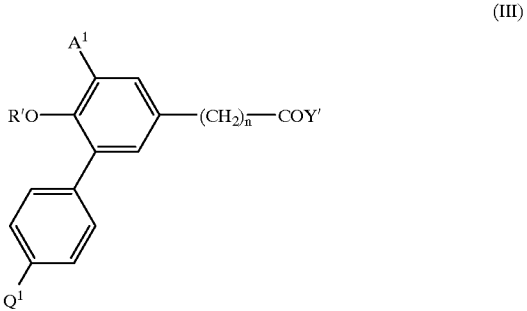

wherein R' is a straight or branched saturated alkyl of $C_4$ or $C_5$ (a'), cyclopentyl, cyclohexyl, cyclopentylmethyl, cyclohexylmethyl or —$(CH_2)_m$W, proviso that in the saturated alkyl (a'), any carbons except for carbon constructing the ether bond may optionally be substituted by one of hydroxy or acetoxy; secondary carbon except for carbon constructing the ether bond may optionally be substituted by one of oxo; or any carbons except for carbon constructing the ether bond may optionally be substituted by 1–3 halogens; W is —$CONR^1R^2$ or alkyloxycarbonyl which can be converted to carboxy by hydrolysis, or nitrile; Y' is lower alkoxy such as methoxy or ethoxy; Al is hydrogen, hydroxy, methoxy, nitro or —NHZ', in which Z' is —$COR^{3'}$ or —$SO_2R^4,R^{3'}$ of which is hydrogen or saturated alkyl of $C_{1-4}$ (b') or —$NR^5_2$; any carbons in the saturated alkyl (b') may optionally be substituted by one of acetoxy or 1–3 halogens; $Q^1$ is hydrogen, hydroxy, methoxy, acetoxy or benzoyloxy; and n, m, $R^1$, $R^2$, $R^4$ and $R^5$ have the same meanings hereinbefore, with base in a polar solvent, converting a group Y' to hydroxy, and simultaneously converting, if those groups exist, acetoxy in the saturated alkyl (a') to hydroxy, alkyloxycarbonyl or nitrile in W' to carboxy, acetoxy in the saturated alkyl (b') to hydroxy, or acetoxy or benzoyloxy in the group Q to hydroxy.

Examples of base used herein are alkaline metal salt such as sodium hydroxide, potassium hydroxide, sodium carbonate, potassium carbonate, sodium methoxide and potassium t-butoxide, and organic base such as triethylamine. Amount of use thereof is, generally, 1–20 molar excess in case of alkaline metal salt, preferably 1–10 molar excess, and equimolar to large excess in case of organic base.

Examples of polar solvent are water, methanol, ethanol, tetrahydrofuran and dioxane, and these can be used by mixing if necessary. Reaction temperature can be selected within suitable temperature from room temperature to reflux temperature of the solvent. Reaction time is usually 0.5–72 hours when alkaline metal salt is used, preferably 1–48 hours, and when organic base is used, it is usually from 5 hours to 14 days. The reaction process can be traced by thin layer chromatography (TLC) and high performance liquid chromatography (HPLC), consequently, the reaction can be terminated when the yield of the compound (II) reaches to maximum.

The thus obtained compound (II) can be isolated from the reaction mixture in the stage of free carboxyic acid, in case of the polar solvent being aqueous solvent, by distilling the solvent, neutralizing with inorganic acid such as hydrochloric acid, dissolving the residue with non-aqueous solvent, washing with weak acidic aqueous solution or water, and removing the solvent. In case that the polar solvent is non-aqueous solvent, the compound (II) can be isolated by neutralizing the reaction mixture, washing with water and removing the solvent.

In case that, after reaction, the compound (II) is solidified by forming salt with using base, salt of the compound (II) can be obtained by isolating it with conventional manner and being purified.

[The Process for Production 2]
(Process b-1)

A compound of the general formula (IV), which is the compound (I) of the present invention, wherein Y is amino and R is —$(CH_2)_m$COOH;

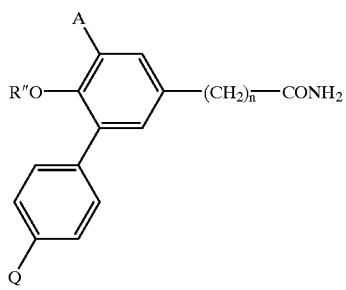

(IV)

wherein R" is straight or branched saturated alkyl of C4 or C5 (a), cyclopentyl, cyclohexyl, cyclopentylmethyl, cyclohexylmethyl or —$(CH_2)_m$CONR$^1$R$^2$, n, m, A, Q, R$^1$, R$^2$ and saturated alkyl (a) have the same meanings hereinbefore [hereinafter simply designates as "compound (IV)"], can be produced by reacting, for example, the compound (II) hereinbefore with inorganic halogenide without presence of solvent or in an inert solvent to convert acid halogenide, which is then reacting with excess concentrated aqueous ammonia directly or dissolved in an inert solvent.

Examples of inorganic halogenide are thionyl chloride, phosphoryl chloride, phosphorus pentachloride and phosphorus trichloride, and among them, thionyl chloride is preferable. Amount of halogenide to be used is generally equivalent to large excess for the compound (II), preferably 1.5–5 molar excess. Examples of inert solvent are halogenated hydrocarbon such as dichloromethane, chloroform and 1,2-dichloroethane, ether such as tetrahydrofuran and dioxane and benzenes such as benzene, toluene, xylene and chlorobenzene. These solvents can be used alone or mixture thereof. Catalytic amount of N,N-dimethylformamide can optionally be added for stimulating the reaction. Reaction temperature can be selected generally at room temperature to reflux temperature of the solvent. Reaction time is usually 0.5–24 hours, preferably 1–6 hours.

Examples of inert solvent used in a reaction with ammonia are halogenated hydrocarbon such as dichloromethane, chloroform and 1,2-dichloroethane, ether such as tetrahydrofuran and dioxane and benzenes such as benzene, toluene, xylene and chlorobenzene. Reaction temperature can be selected generally from −10° C. to room temperature. Reaction time is generally 0.5–24 hours, preferably 0.5–6 hours.

(Process b-2)

The compound (IV) can be produced according to a method described in New Experimental Chemistry Series (Japan Chemical Society Ed., Maruzen Publ. Co.), Vol. 14, page 1147, Ammonolysis, in which the compound (III) hereinbefore is reacted in an excess amount of concentrated aqueous ammonia in the presence of catalysis such as ammonium chloride, sodium methoxide or butyl lithium.

(Process b-3)

The compound (I), wherein Y is amino and R is —$(CH_2)_m$COOH, i.e. a compound represented by the general formula (V)

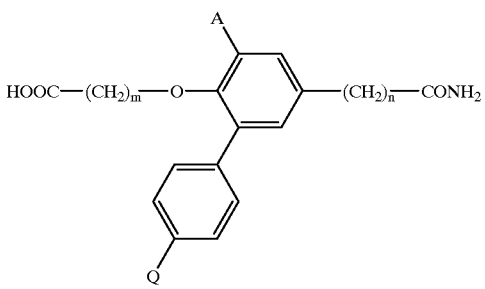

(V)

wherein n, m, A and Q have the same meanings hereinbefore, [hereinafter simply designates as "the compound (V)"] can be synthesized by subjecting to amidation of the compound (III), wherein R is —$(CH_2)_m$COOBn, i.e. a compound (VI) of the formula,

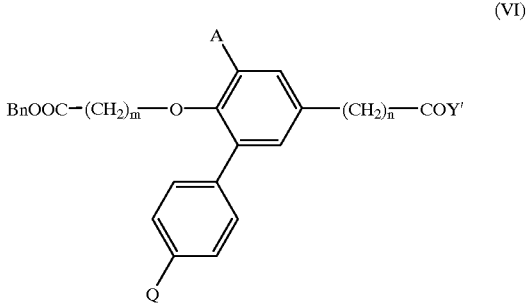

(VI)

wherein Bn is benzyl, and n, m, Y', A and Q have the same meanings hereinbefore, [hereinafter simply designates as "the compound (VI)"], according to a method of ammonolysis shown in the above process b-2, then the benzyl ester is hydrogenated using hydrogen source such as hydrogen gas in the presence of catalysis such as palladium carbon powder in an inert solvent such as methanol to convert carboxy.

The compound (III) [including the compound (VI)] used in the processes 1 and 2 for production of the compound (I) can be produced by, for example, the following methods 1–4 for synthesis of intermediates.

[Process for Production of Intermediate 1]

(Process c-1)

The compound (III), wherein $A^1$ and $Q^1$ are hydrogen, i.e. a compound (VII) of the general formula,

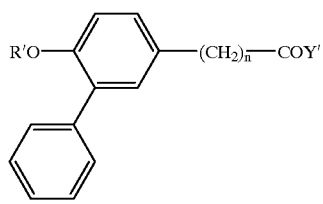

(VII)

wherein n, R' and Y' have the same meanings hereinbefore, [hereinafter simply designates as "the compound (VII)"], can be produced by reacting the compound of the formula (VIII),

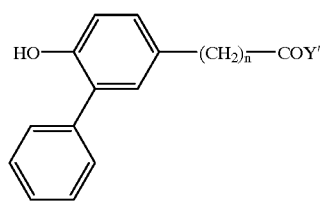

(VIII)

wherein n, and Y' have the same meanings hereinbefore, [hereinafter simply designates as "the compound (VIII)"], with the formula (IX),

R'—X (IX)

wherein X is halogen such as chlorine, bromine and iodine or sulfate such as p-toluenesulfonyloxy, methanesulfonyloxy and (2,4,6-trimethylphenyl) sulfonyloxy (mesitylenesulfonyloxy), and R' has the same meaning hereinbefore, (hereinafter simply designates as "alkylating agent"), in an inert solvent in the presence of suitable base.

Examples of alkylating agent used herein are the straight or branched alkyl halide of $C_4$ or $C_5$ such as alkyl iodide, alkyl bromide, alkyl chloride or cyclohexylmethyl bromide, the haloalkane carboxylate such as bromoacetic acid ester and 4-bromobutyric acid ester, and the haloalkane carboxamide such as bromoacetamide and chloroacetic acid dimethylamide, in all of which carbon except for carbon binding with halogen is optionally substituted by an acetoxy, secondary carbon except for carbon binding with halogen is optionally substituted by an oxo, or carbon except for carbon binding with halogen is optionally substituted by 1–3 halogens, or the alkyl sulfate obtained by conventionally mesylated, tosylated or methylene sulfonylated straight or branched primary or secondary alcohol or cyclopentylmethyl alcohol, or the alkyl sulfate obtained by that the commercially available alkyl diol of $C_4$ or $C_5$ having primary and secondary hydroxy is conventionally methylenesulfonylated the primary alcohol, then the secondary alcohol is conventionally protected by acetyl. Amount of use thereof is generally equimolar to 40 molar excess, preferably equimolar to 10 molar excess, of the compound (VIII). Examples of inert solvent used in the reaction are alcohol such as methanol or ethanol, ether such as tetrahydrofuran or dioxane, benzens such as benzene, toluene or xylene, N,N-dimethylformamide, acetonitrile or acetone, and can be used if necessary with mixture thereof. Examples of base used herein are, for example, alkaline metal such as sodium hydroxide, potassium hydroxide, sodium carbonate, potassium carbonate, sodium hydride, sodium methoxide and potassium t-butoxide, and tertiary organic amine such as pyridine, 4-dimethylamino pyridine, 1,8-diazabicyclo [5,4,0]-undecene, trimethylamine and triethylamine. Amount of use thereof is generally equimolar to 10 molar excess, preferably equimolar to 5 molar excess, of the compound (VIII). Reaction temperature can be selected within suitable temperature from room temperature to reflux temperature of the solvent, preferably at room temperature to 80° C. Reaction time is usually 1 hour–6 days, preferably 2–48 hours. The reaction process can be traced by thin layer chromatography (TLC) and high performance liquid chromatography (HPLC), consequently, the reaction can be terminated when the yield of the compound (VII) reaches to maximum. In case of slow reaction, 0.1–1.5 molar excess of catalyst such as potassium iodide or copper powder can optionally be added.

(Process c-2)

The compound (VII) can be produced by the Mitsunobu reaction from the compound (VIII) according to the reference (O. Mitsunobu, Synthesis, page 1, 1981). Namely, it can be obtained by reacting the compound (VIII) in organic solvent in the presence of phosphine such as triphenylphosphine and tributylphosphine and azo compound such as diethyl azodicarboxyate, N,N,N',N'-tetramethyl azodicarboxamide, 1,1'-(azodicarbonyl) dipiperidine and N,N,N',N'-tetraisopropyl carboxamide, with commercially available straight or branched primary or secondary alcohol of $C_4$ or $C_5$, cyclopentyl alcohol, cyclohexyl alcohol or cyclopentylmethyl alcohol. Examples of solvent are ether such as diethyl ether, tetrahydrofuran or dimethoxyethane, and benzens such as benzene, toluene or xylene, and can be used if necessary with mixture thereof. Amount of phosphins used is generally equimolar to 10 molar excess, preferably 1.5 to 5 molar excess, of the compound (VIII). Amount of azo compound used is generally equimolar to 10 molar excess, preferably 1.5 to 5 molar excess, of the compound (VIII). Reaction temperature can be selected within suitable temperature from −20° C. to room temperature, preferably at 0° C. to room temperature. Reaction time is usually 3 hours–3 days, preferably 6–24 hours. The reaction process can be traced by thin layer chromatography (TLC) and high performance liquid chromatography (HPLC), consequently, the reaction can be terminated when the yield of the compound (VII) reaches to maximum.

(Process c-3)

The compound (VII), wherein R' is 2-hydroxy alkyl of $C_4$ or $C_5$, can also be produced by reacting the compound (VIII) with the corresponding 1,2-epoxy alkane such as 1,2-epoxy butane and 1,2-epoxy pentane in the presence of base in an organic solvent. Amount of 1,2-epoxy alkane used is generally equimolar to large excess, preferably 3 to 10 molar excess, of the compound (VIII). Examples of base used herein are, for example, alkaline metal such as sodium hydroxide, potassium hydroxide, sodium carbonate, potassium carbonate, sodium hydride, sodium methoxide and potassium t-butoxide, and tertiary organic amine such as pyridine, 4-dimethylamino pyridine, 1,8-diazabicyclo [5,4,0]-undecene, trimethylamine, triethylamine and diisopropylethylamine. Amount of use thereof is generally equimolar to large excess, preferably 3 to 20 molar excess, of the compound (VIII).

Since this reaction needs for long time, it is preferably proceeded in the autoclave. Examples of solvent used are alcohol such as methanol or ethanol, ether such as tetrahydrofuran or dioxane, benzens such as benzene, toluene or xylene, N,N-dimethylformamide, acetonitrile or acetone. Reaction temperature is generally at room temperature to 200° C. Reaction time is generally for 1 hour to 7 days.

(Process c-4)

The compound (VII), wherein R' is —(CH$_2$)$_2$W, can be produced by reacting the compound (VI) with acrylic acid derivative such as acrylate, acrylamide or acrylonitrile and base, if required adding copper catalyst. Amount of acrylic acid derivative is generally 2 molar excess to large excess of the compound (VIII). Examples of base used in this reaction are alkaline metal such as metallic sodium, sodium methoxide and potassium t-butoxide, tertiary ammonium such as toriton B (trimethylbenzyl ammonium hydroxide), and tertiary organic amine such as trimethylamine, triethylamine and isopropyl ethylamine. Examples of copper catalyst are cupric hydroxide and copper acetate hydrate. Amount used thereof is generally 0.1—equimolar of the compound (VIII). Reaction can be proceeded generally in acrylic acid derivative as a solvent or in alcohol such as methanol and ethanol or benzenes such as benzene, toluene and xylene. Reaction time is usually 3–24 hours. The reaction process can be traced by thin layer chromatography (TLC) and high performance liquid chromatography (HPLC), consequently, the reaction can be terminated when the yield of the compound (VII) reaches to maximum.

(Process d)

The compound (VIII), wherein n is 2, can be produced by conventionally demethylating the known 3-(2-methoxy-1,1'-biphenyl-5-yl)propionic acid disclosed in the reference (R. R. Burtner et al. J. Am. Chem. Soc. 75: 2334, 1953) and conventionally esterifying the carboxyic acid. For example, 3-(2-methoxy-1,1'-biphenyl-5-yl)propionic acid can be obtained by reacting at about 180° C. in pyridine-hydrochloric acid complex to convert methoxy to hydroxy, and reacting the thus obtained compound with thionyl chloride in alcohol such as methanol.

(Process d)

The compound (VIII), wherein n is 3, can be produced by demethylating and esterifying the compound of the formula (X), [hereinafter simply designates as "the compound (X)"],

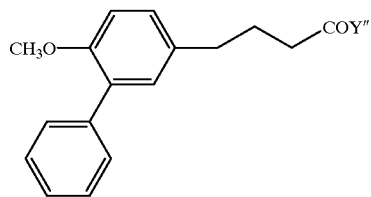
(X)

wherein Y" is hydroxy or lower alkoxy such as methoxy and ethoxy, according to the same method described in the process d for production of the intermediate 1.

(Process e)

The compound (X) can be produced by reducing a ketone carbonyl of the formula (XI), [hereinafter simply designates as "the compound (XI)"],

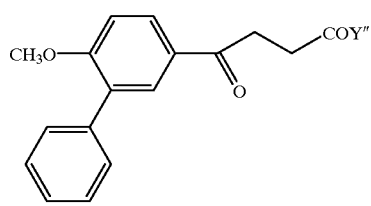
(XI)

wherein Y" has the same meaning hereinbefore, according to a method described in the reference (K. P. Mathai et al. J. Indian Chem. Soc. 42: 86, 1965).

The compound (X) can also be produced by hydrogenating the compound (XI) by using hydrogen source such as hydrogen gas, ammonium formate and hydrazine hydride in inert solvent in the presence of catalyst. Examples of inert solvent are alcohol such as methanol and ethanol, halogenated hydrocarbon such as dichloromethane and 1,2-dichloroethane, ether such as tetrahydrofuran and dioxane, and ethyl acetate, and these solvent can optionally be used in a mixture thereof. Trace amount of acid such as hydrochloric acid and acetic acid can be added for stimulating the reaction. Catalyst used herein is palladium carbon powder, platinum oxide, and the like.

(Process f)

The compound (XI), wherein Y" is hydroxy, i.e. 3-(4-methoxy-3-phenylbenzoyl)propionic acid is a known compound in the reference (R. R. Burtner et al. J. Am. Chem. Soc. 75: 2334, 1953). The compound, wherein Y" is lower alkoxy such as methoxy and ethoxy, can be produced by reacting the commercially available 2-methoxy biphenyl with 3-alkoxycarbonyl propionyl chloride in the presence of Lewis acid catalyst in Friedel-Crafts reaction. Amount of acid chloride is generally 1–10 molar excess, preferably 1.5–4 molar excess of the raw material. Examples of Lewis acid are aluminum chloride, tin chloride or titanium chloride. Amount of these materials is generally 1–10 molar excess, preferably 1–4 molar excess. Example of solvent used in the reaction is halogenized hydrocarbon such as dichloromethane and 1,2-dichloroethane, nitrobenzene and carbon disulfide. Reaction temperature is selected suitable temperature of generally at −10–100° C., preferably 0° C.—room temperature. Reaction time is usually 1–16 hours, preferably 2–8 hours. The reaction process can be traced by thin layer chromatography (TLC) and high performance liquid chromatography (HPLC), consequently, the reaction can be terminated when the yield of the compound (XI) reaches to maximum.

[Process for Production of Intermediate 2]

(Process d)

The compound (III), wherein any one of A$^1$ and Q$^1$ is hydrogen and n is 2, i.e. a compound (XII) of the general formula,

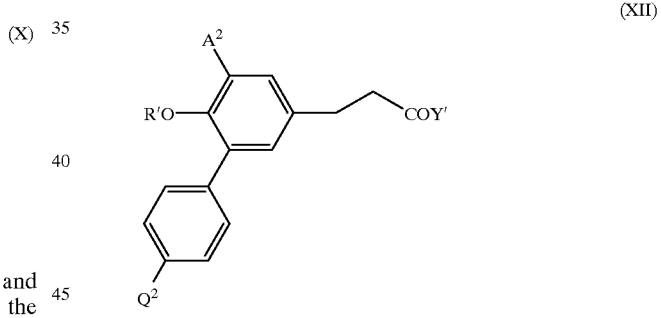
(XII)

wherein A$^2$ and Q$^2$ are hydrogen or hydroxy, and at least one of them is hydroxy, and R' and Y' have the same meanings hereinbefore, [hereinafter simply designates as "the compound (XII)"], can be produced by the same process of demethylating and esterifying the compound of the formula (XIII),

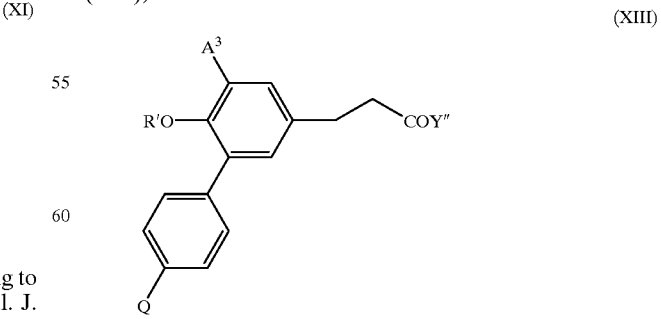
(XIII)

wherein A$^3$ is hydrogen or methoxy, and R' and Y7 have the same meanings hereinbefore and at least one of them is other than hydrogen [hereinafter simply designates as "the compound (XIII)"], as shown in the process for production of intermediate 1, process d.

(Process g)

The compound (XIII) can be produced by catalytic reaction of the compound (XIV) of the formula,

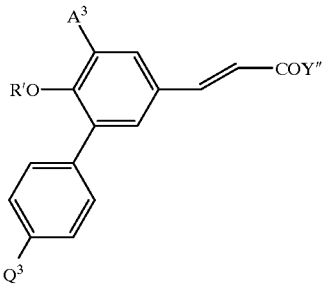

(XIV)

wherein $Q^3$ is hydrogen, methoxy or benzyloxy, R', Y" and $A^3$ have same meanings hereinbefore, [hereinafter simply designates as "the compound (XIV)"], as described in the chemical reference. For example, double bond in the compound (XIV) is hydrogenated by using hydrogen source such as hydrogen gas, ammonium formate and hydrazine hydride, in alcoholic solvent such as methanol or ethyl acetate alone or with mixture, in the presence of catalyst such as palladium carbon, and simultaneously converting benzyloxy of $Q^3$ to hydroxy, if it exists.

(Process h)

The compound (XIV) can be produced, for example, according to a method described in New Experimental Chemistry Series (Japan Chemical Society Ed., Maruzen Publ. Co.), Vol. 14, page 238, Homer-Emmons reaction, from the compound (XV) of the formula (XV),

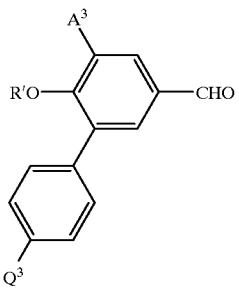

(XV)

wherein R', $A^3$ and $Q^3$ have same meanings hereinbefore and at least one of $A^3$ and $Q^3$ is other than hydrogen, [hereinafter simply designates as "the compound (XV)"]. Namely, the compound (XV) is reacted with the commercially available dialkyl phosphono acetic acid ester in inert solvent, for example alcohol such as methanol and ethanol, or ether such as tetrahydroftiran and dimethoxy ethane, in the presence of sodium hydride or sodium alkoxide. Reaction temperature is generally at −10° C.—reflux temperature of the solvent, preferably at 0° C.—room temperature. Reaction time is generally at 1–16 hours, preferably at 2–8 hours. The reaction process can be traced by thin layer chromatography (TLC) and high performance liquid chromatography (HPLC), consequently, the reaction can be terminated when the yield of the compound (XIV) reaches to maximum.

(Process i)

The compound (XV) can be produced from the compound (XVI) of the formula,

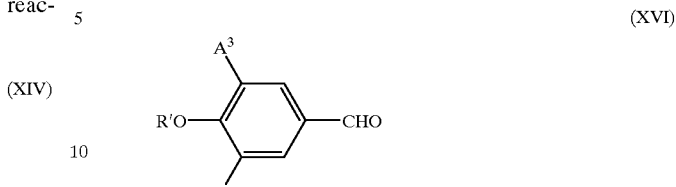

(XVI)

wherein X' is bromine or iodine, and R' and $A^3$ have the same meanings hereinbefore, [hereinafter simply designates as "the compound (XVI)"] and the compound (XVII) of the formula,

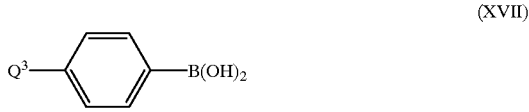

(XVII)

wherein $Q^3$ has the same meanings hereinbefore, [hereinafter simply designates as "the compound (XVII)"], according to the method described in Experimental Chemistry Series, 4th Ed. (Japan Chemical Society Ed., Maruzen Publ. Co.), Vol. 25, page 403, Suzuki reaction. Namely, the compound can be obtained by reacting the compound (XVI) with the compound (XVII) in solvent in the presence of catalyst prepared from phosphine such as triphenyl phosphine, tri(o-toryl)phosphine, 1,2-bis(diphenyl phosphino)ethane and 1,1'-bis(diphenylphosphino)ferrocene and palladium complex such as palladium acetate and tris-dibenzylidene acetone palladium (O), or tetrakis (triphenylphosphine)palladium (O) catalyst, and base such as potassium carbonate, sodium hydroxide or triethylamine. Examples of solvent are ether such as dioxane and dimethoxy ethane, benzens such as benzene, toluene and xylene, N,N-dimethylformamide and water, if necessary mixture thereof. Amount of catalyst used is generally 0.001—equimolar amount, preferably 0.01–0.10 molar excess of the compound (XVI). Amount of base used is generally 1–20 molar excess, preferably 1–5 molar excess of the compound (XVI). Amount of the compound (XVII) is generally 1–10 molar excess, preferably 1–5 molar excess of the compound (XVI). Reaction temperature is generally at −10° C.—reflux temperature of the solvent, preferably at 0° C.—room temperature. Reaction time is generally at 1–24 hours, preferably at 2–8 hours. The reaction process can be traced by thin layer chromatography (TLC) and high performance liquid chromatography (HPLC), consequently, the reaction can be terminated when the yield of the compound (XV) reaches to maximum. 4-benzyloxyphenyl boric acid in the compound (XVII) can be produced from the compound, which is produced by benzylating hydroxy in the commercially available 4-bormophenol, according to the reference (Y. Satoh et al. Synthesis, page 1146, 1994).

Process c)

The compound (XVI) can be produced by etherifying 3-bromo-4-hydroxybenzaldehyde, which is produced by conventional demethylation of the commercially available 3-bromo-4-methoxybenzaldehyde described in the Chemical references, or the commercially available 5-iodovanillin according to any methods shown in the prior process c in the production method of the intermediate 1.

[Process for Production of Intermediate 3]
(Process d)

The compound (III), wherein A' or Q' is hydroxy and n is 3, i.e. the compound (XVIII) of the formula,

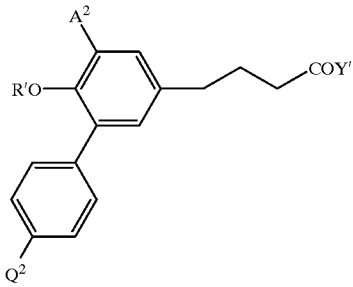

(XVIII)

wherein R', Y', A² and Q² have the same meanings hereinbefore, and at least either A² or Q² is hydroxy, [hereinafter simply designates as "the compound (XVIII)"], can be produced by demethylating and esterifying the compound of the formula (XIX),

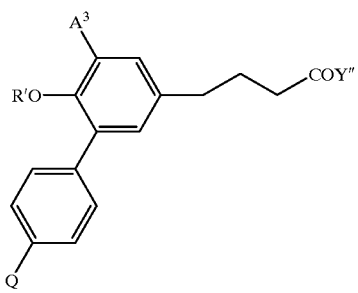

(XIX)

wherein R', Y", A³ and Q have the same meanings hereinbefore, and at least either A³ or Q is other than hydrogen, [hereinafter simply designates as "the compound (XIX)"], according to the same method described in the process d for production of the intermediate 1.

(Process e)

The compound (XIX) can be produced from the compound (XX) of the formula,

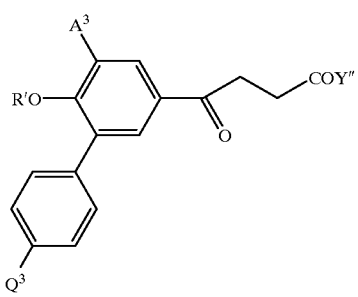

(XX)

wherein R', Y", A³ and Q³ have the same meanings hereinbefore, and at least either A³ or Q³ is other than hydrogen, [hereinafter simply designates as "the compound (XX)"], according to the same method described in the process e for production of the intermediate 1.

(Process f)

The compound (XX) can be produced from the compound (XXI) of the formula,

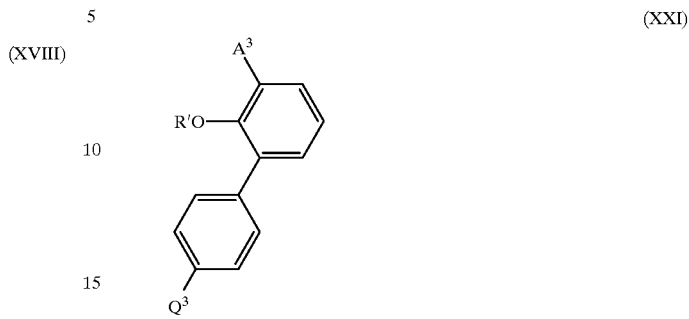

(XXI)

wherein R', A³ and Q³ have the same meanings hereinbefore, and at least either A³ or Q³ is other than hydrogen, [hereinafter simply designates as "the compound (XXI)"], according to the same method described in the process f for production of the intermediate 1.

(Process c)

The compound (XXI) can be produced from the compound (XXII) of the formula,

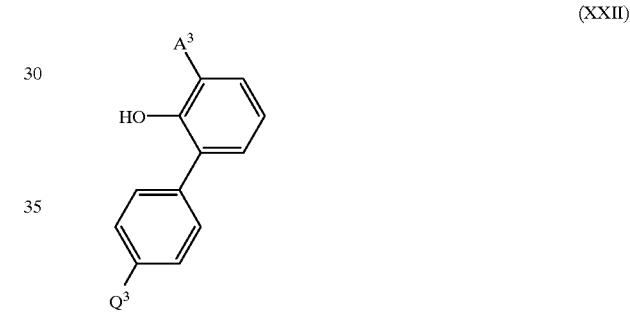

(XXII)

wherein A³ and Q³ have the same meanings hereinbefore, and at least either A³ or Q³ is other than hydrogen, [hereinafter simply designates as "the compound (XXII)"], according to the same method described in the process c for production of the intermediate 1.

(Process j)

The compound (XXII) can be produced by conventional demethoxymethylation of the compound (XXIII) of the formula,

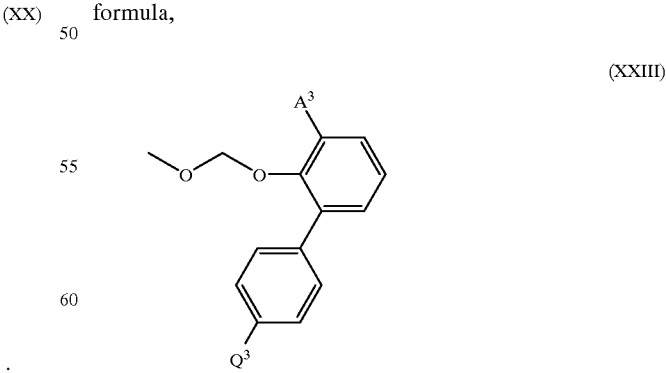

(XXIII)

wherein A³ and Q³ have the same meanings hereinbefore, and at least either A³ or Q³ is other than hydrogen, [hereinafter simply designates as "the compound (XXIII)"].

For example, the compound can be obtained by treating with acid such as phosphoric acid in the water miscible solvent such as dioxane.

(Process k)

The compound (XXIII) can be produced from the compound (XXIV) of the formula,

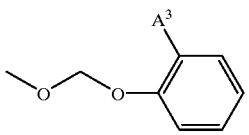
(XXIV)

wherein $A^3$ has the same meaning hereinbefore, [hereinafter simply designates as "the compound (XXIV)"], and the compound (XXV) of the formula,

(XXV)

wherein $Q^3$ and X' have the same meanings hereinbefore, according to the method described in Experimental Chemistry Series, 4th Ed. (Japan Chemical Society Ed., Maruzen Publ. Co.), Vol. 25, page 401, cross-coupling reaction. For example, after the compound (XXIV) is lithiated by alkyl lithium such as n-butyl lithium and t-butyl lithium, the compound, which is subjected to metal exchange with zinc chloride, is reacted with the compound (XXV) in the presence of palladium catalyst such as tetrakis (triphenylphosphine)(O).

The compound (XXIV) can be produced from the commercially available phenol or 2-methoxy phenol and methoxymethyl chloride by the method shown in the process 3, process c-1.

The compound (XXV), wherein $Q^3$ is benzyloxy, can be produced by reacting hydroxy of the commercially available 4-bromophenol with benzyl halide. The other type of compound (XXV) can easily be obtained.

[Process for Production of Intermediate 4]

(Process 1-1)

The compound (III), wherein $A^1$ is —NHZ', i.e. the compound of the formula (XXVI),

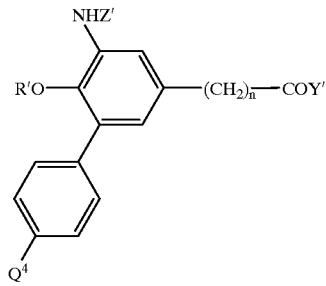
(XXVI)

wherein $Q^4$ is hydrogen, methoxy, acetoxy or benzoyloxy, n, R', Y' and Z' have the same meanings hereinbefore, can be produced by condensing the compound of the formula (XXVII),

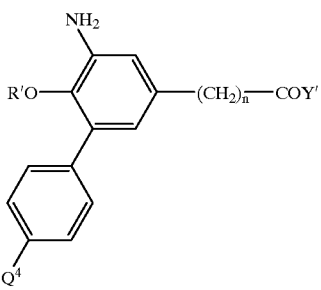
(XXVII)

wherein n, R', Y' and $Q^4$ have the same meanings hereinbefore, [hereinafter simply designates as "the compound (XXVII)"], in an inert solvent with acylating agent such as acid anhydride, acid halide, N,N-dialkylcarbamoyl chloride, alkylsulfonyl chloride or N,N-dialkylsulfamoyl chloride, if necessary in the presence of base. Examples of inert solvent used herein are halogenated hydrocarbon such as dichloromethane and chloroform, ether such as tetrahydrofuran, dioxane and diethyl ether, dimethyl sulfoxide, N,N-dimethylformamide and acetonitrile. These can be used alone or admixture.

Examples of acylating agent, for example, acid anhydride are acetic anhydride, propionic anhydride, butyric anhydride, isobutyric anhydride, pivalic anhydride and trifluoroacetic anhydride. Examples of acid halide are acetyl chloride, propionyl chloride, butyryl chloride, isobutyryl chloride, isovaleryl chloride, pivaloyl chloride, chloroacetyl chloride, acetoxyacetyl chloride and methoxyacetyl chloride. Examples of N,N-dialkylcarbamoyl chloride are N,N-dimethylcarbamoyl chloride and N,N-diethylcarbamoyl chloride. Examples of sulfonic anhydride are trifluoromethanesulfonic anhydride, etc. Examples of alkylsulfonyl chloride are methylsulfonyl chloride and ethylsulfonyl chloride. Examples of N,N-dialkylsulfamoyl chloride are N,N-dimethylsulfamoyl chloride, etc. Amount of use thereof is 1–20 molar excess, preferably 1–10 molar excess of the compound (XXVII).

Examples of base used in the above reaction are alkaline metal such as sodium hydrogen carbonate, sodium hydroxide, potassium carbonate, sodium carbonate, potassium hydroxide and sodium methylate, and organic amine such as pyridine, trimethylamine and triethylamine. Amount use thereof is generally 1–20 molar excess, preferably 1–10 molar excess of the compound (XXVII).

Reaction temperature is generally at −30–120° C., preferably −20–50° C. Reaction time is generally at 0.5–72 hours, preferably at 0.5–48 hours. The reaction process can be traced by thin layer chromatography (TLC) and high performance liquid chromatography (HPLC), consequently, the reaction can be terminated when the yield of the compound (XXVI) reaches to maximum.

The compound (XXVI) hereinabove, wherein Z' is formyl, can be produced by replacing the acylating agent in the above reaction to a mixture of 99% formic acid and acetic anhydride.

(Process 1-2)

The compound (XXVI), wherein Z' is carbamoyl, can be produced, for example, by reacting the compound (XXVII) with 1–5 molar excess of alkaline metal cyanate (such as NaOCN and KOCN) in a mixture of water and acetic acid. Reaction temperature is generally at room temperature −100° C. The reaction time is 1–24 hours.

(Process m)

The compound (XXVII) can be produced by hydrogenating nitro group of the compound (XXVIII) of the formula,

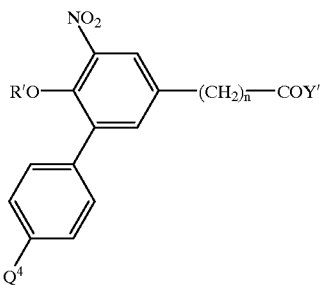

(XXVIII)

wherein n, R', Y' and $Q^4$ have the same meanings hereinbefore, [hereinafter simply designates as "the compound (XXVIII)"], with the conventional method, for example, in a solvent such as methanol, in the presence of catalyst such as palladium carbon powder or palladium oxide, at room temperature or heated temperature, or by reducing with hydrochloric acid in the presence of iron powder or tin (II) salt at room temperature to reflux temperature.

(Process n)

The compound (XXVIII) can be produced by nitrating the compound (XXIX) of the formula,

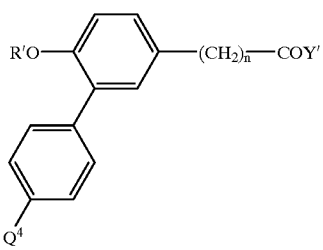

(XXIX)

wherein n, R', Y' and $Q^4$ have the same meanings hereinbefore, [hereinafter simply designates as "the compound (XXIX)"], according to the conventional method described in the chemical reference. For example, a mixture of 70–98% nitric acid and acetic anhydride solution was added to acetic anhydride solution of the compound (XXIX) and reacted at −20–5° C.

(Process o)

The compound (XXIX) can be produced by acetylating or benzoylating the compound (XXX) of the formula,

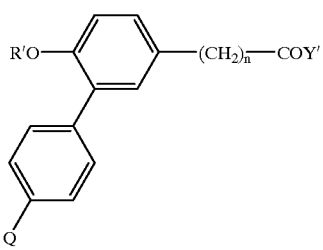

(XXX)

wherein n, R', Y' and Q have the same meanings hereinbefore, [hereinafter simply designates as "the compound (XXX)"], according to the conventional method. For example, the compound (XXX) is reacted with acetyl chloride or benzoyl chloride at 0° C.—room temperature.

The compound (I) of the present invention having assymetric carbon in the substituent R can be isolated as optical isomer of the objective product or its precursor by conventional method. Such the methods include a method of high performance liquid chromatography (HPLC) using optically active column (process p) and a method, in which the compound is condensing with optically active compound, separating the produced diastereoisomer and decomposing the same again. In case that the precursor is isolated to form optical isomer, thereafter the aforementioned process is performed, then the optical isomer of the objective compound (I) can be produced.

The compound (I) of the present invention having acidic functional group such as carboxy and phenolic hydroxy can be converted to pharmaceutically acceptable salt (such as inorganic salt with sodium or ammonium, or organic salt with triethylamine) by conventional method.

In order to obtain inorganic salt, for example, the objective compound (I) is preferably dissolved in aqueous solution containing at least equimolar amount of hydroxide, carbonate or bicarbonate corresponding to the desired inorganic salt. In the reaction, water miscible inert organic solvent such as methanol, ethanol, acetone and dioxane can be mixed. For example, when sodium hydroxide, sodium carbonate or sodium bicarbonate is used, solution of sodium salt can be obtained.

In case that solid salt is required, the solution is evaporated, or slightly polar solvent of water miscible organic solvent such as butanol or ethylmethyl ketone is added to obtain solid salt.

The compounds described in the specification of the present invention can be purified by known methods such as recrystallization or chromatography (column chromatography, flush column chromatography, TLC and HPLC).

The compound (I) of the present invention and pharmaceutically acceptable salt thereof has no effect for production of immunoglobulin G (IgG), which is thought to be important for biological reaction such as prevention of infection, has selective suppressive action against IgE antibody production, and shows no death when administered orally 300 mg/kg in rats. Consequently, it is safe compound for pharmaceuticals and is useful as an active ingredient of the pharmaceuticals. Preferable use of the compound (I) of the present invention as pharmaceuticals includes suppressive agent for IgE antibody production and drug for treatment and/or prevention of allergic diseases caused by IgE antibody production such as bronchial asthma, allergic rhinitis, atopic dermatitis, allergic conjunctivitis and anaphylaxis.

In order to use the compound (I) of the present invention or pharmaceutically acceptable salt thereof as the above pharmaceuticals, effective amount of the compound (I) or pharmaceutically acceptable salt thereof can be used directly or mixed with pharmaceutically acceptable carrier to prepare pharmaceutical composition. Such the carrier can be a suspending agent such as carboxymethyl cellulose or purified water and physiological saline, and other known carriers.

Examples of the pharmaceutical form for preparing formulation of the above pharmaceutical composition are tablet, powder, granule, syrup, suspension, capsule and injection. Various carriers are used for these formulations. For example, carriers for oral formulation include excipient, binder, lubricant, fluid promoter and coloring agent.

Parenteral formulation of the compound of the present invention such as injection can be prepared generally by mixing, for example, with distilled water for injection, physiological saline, glucose solution, vegetable oil for injection, propylene glycol and polyethylene glycol. In addition, in necessary, bactericide, antiseptics, stabilizer, tonicity agent and soothing agent can be added.

In case of administration of the compound of the present to humans, it can be administered orally in the form of tablet, powder, granule, suppository, suspension and capsule. Parenteral administration can be performed in the form of injection including drip infusion, cream or spray. Amount of administration depends on diseases, administration form, age, body weight, and symptoms, but in general 3–1000 mg, 1–3 times per day per adult are administered. Term for administration is generally from several days to 2 months, but the daily dose and dosage term can be changed depending of symptom of patients.

EXAMPLES

Following examples illustrate the present invention in detail.

Thin layer chromatography (TLC) used is a precoated silica gel 60 F254 (Merck). After developing with chloroform:methanol (100–4:1–0), acetonitrile:acetic acid:water (100–200:1–4:1–4), or ethyl acetate:n-hexane (10–0:1–10), the product was confirmed by irradiation with UV, or coloring reaction with ninhydrine or dinitrophenyl hydrazine hydrochloric acid solution. Column chromatography is used with silica gel (Wako gel C-200, Wako Pure Chemical Industry, Ltd.) and flush chromatography is used with silica gel 60 (230–400 mesh, Merck). For measurement with nuclear magnetic resonance (NMR), Gemini-300 (FT-NMR, Varian) is used. Deuterized chloroform ($CDCl_3$) is used, unless specified, as a solvent. Chemical shift is used with tetramethylsilane (TMS) as inner standard, and expressed by δ (ppm). Coupling constant is expressed by J (Hz). Symbols of splitting patters are expressed by s; singlet, d; doublet, t; triplet, q; quartet, dd; doublet doublet, m; multiplet and br; broad, Mass spectrum (MS) used is JEOL-JMS-SX102 (Nippon Denshi) and measured by fast atom bombardment mass spectrum (FAB-MS). Data are shown in table 1.

Example 1
3-(2-butoxy-1,1'-biphenyl-5-yl)propionic acid (Compound 01)
(Process d) Synthesis of Methyl 3-(2-hydroxy-1,1'-biphenyl-5-yl)propionate (Intermediate 1)

3-(2-methoxy-1,1'-biphenyl-5-yl)propionic acid (4.00 g), which was a known compound in the reference (R. R. Burtner et al. J. Am. Chem. Soc. 75: 2334, 1953), was added to pyridine hydrochloric acid complex prepared by heating, after mixing pyridine with conc. Hydrochloric acid (each 15 ml), at 180° C. for 1 hour, and the mixture was stirred at 180° C. for 3 hours. Reaction mixture was poured into ice-cold 5 N—HCl (100 ml) and extracted with ethyl acetate (150 ml×2). After drying the organic layer, the solvent was distilled off in vacuo. Thionyl chloride (2.4 ml) was added dropwise to the residual methanol solution (75 ml) under ice cooling, and stirred for 16 hours by gradually changing to room temperature. Solvent was concentrated in vacuo, and chloroform (200 ml) was added to the residue, washed with aqueous saturated sodium bicarbonate solution and aqueous saturated sodium chloride solution, in this order, then the organic layer was dried and distilled of in vacuo. The residue was purified by flush column chromatography (hexane:ethyl acetate=4:1) to obtain the compound of the title (3.97 g).
(Process c-1) Synthesis of Methyl 3-(2-butoxy-1,1'-biphenyl-5-yl)propionate (Intermediate 2)

The intermediate 1 (1.20 g), n-butyl iodide (1.62 ml, Tokyo Chemical Ind. Co., Ltd.) and anhydride potassium carbonate (810 mg) were added to N,N-dimethylformamide (15.0 ml) and stirred at room temperature for 16 hours. Ethyl acetate (200 ml) was added to the reaction mixture, which was washed with aqueous saturated sodium bicarbonate solution, aqueous saturated ammonium chloride solution and aqueous saturated sodium chloride solution, in this order, then the organic layer was dried and distilled off in vacuo. The residue was purified by flush column chromatography (hexane:ethyl acetate=8:1) to obtain the compound of the title (1.45 g).
(Process a) Synthesis of 3-(2-butoxy-1,1'-biphenyl-5-yl) propionic Acid (Compound 01)

Aqueous 2 N—NaOH solution (5.0 ml) was added to the methanol (10.0 ml) solution of the intermediate 2 (1.44 g) and stirred at room temperature for 16 hours. After concentrating the reaction mixture, the mixture was acidified by adding 5% aqueous HCl, then extracted with ethyl acetate (200 ml). Organic layer was washed with saturated aqueous NaCl solution, dried and distilled off the solvent to obtain the compound of the title (1.29 g).

Rf=0.34 (chloroform:methanol=20:1).

Example 2
3-(2-isobutoxy-1,1'-biphenyl-5-yl)propionic Acid (Compound 02)
(Process c-1) Synthesis of Methyl 3-(2-isobutoxy-1,1'-biphenyl-5-yl)propionate (Intermediate 3)

The compound of the title (420 mg) was obtained by reacting with the intermediate 1 (400 mg), isobutyl bromide (0.86 ml, Tokyo Chemical Ind. Co., Ltd.) and anhydrous potassium carbonate (270 mg) according to the method described in the process c-1 in example 1. [Proviso that the following modification was added. Reaction was carried out at 80° C. for 24 hours. Purification was performed by flush column chromatography (hexane:ethyl acetate=7:1).]
(Process a) Synthesis of 3-(2-isobutoxy-1,1'-biphenyl-5-yl) propionic Acid (Compound 02)

The compound of the title (373 mg) was obtained by reacting with the intermediate 3 (410 mg) according to the process described in the process a in example 1. (Proviso that the reaction was performed at 65° C. for 2 hours.)

Rf=0.35 (chloroform:methanol=20:1)

Example 3
3-(2-pentyloxy-1,1'-biphenyl-5-yl)propionic Acid (Compound 03)
(Process c-1) Synthesis of Methyl 3-(2-pentyloxy-1,1'-biphenyl-5-yl)propionate (Intermediate 4)

The compound of the title (509 mg) was obtained by reacting with the intermediate 1 (400 mg), n-pentyl iodide (0.61 ml, Tokyo Chemical Ind. Co., Ltd.) and anhydrous potassium carbonate (270 mg) according to the method described in the process c-1 in example 1.
(Process a) Synthesis of 3-(2-pentyloxy-1,1'-biphenyl-5-yl) propionic Acid (Compound 03)

The compound of the title (461 mg) was obtained by reacting with the intermediate 4 (500 mg) according to the process described in the process a in example 1.

Rf=0.34 (chloroform:methanol=20:1)

Example 4
3-(2-cyclopentyloxy-1,1'-biphenyl-5-yl)propionic Acid (compound 04)
(Process c-2) Synthesis of Methyl 3-(2-cylcopentyloxy-1,1'-biphenyl-5-yl)propionate (Intermediate 5)

The intermediate 1 (1.00 g), cyclopentyl alcohol (1.68 g, Tokyo Chemical Ind. Co., Ltd.) and triphenylphosphine (5.11 g, Kanto Chemical Co.) were added to anhydrous THF (20 ml) udner argon atmosphere at 0° C. and stirred. Diethyl azodicarboxylate (3.39 g, Nakaritesque Inc.) was slowly added dropwise and gradually changed to room temperature with stirring for 1 day. Reaction mixture was diluted with ethyl acetate (100 ml), and was washed with aqueous saturated ammonium chloride solution and dried, then the solvent was distilled off in vacuo. The residue was purified by flush column chromatography (hexane:ethyl acetate=9:1) to obtain the compound of the title (820 mg).

(Process a) Synthesis of 3-(2-cyclopentyloxy-1,1'-biphenyl-5-yl)propionic Acid (Compound 04)

The compound of the title (653 mg) was obtained by reacting with the intermediate 5 (820 mg) according to the process described in the process a in example 1.

Rf=0.35 (chloroform:methanol=20:1)

Example 5

3-(2-cyclohexyloxy-1,1'-biphenyl-5-yl)propionic Acid (Compound 05)

(Process c-2) Synthesis of Methyl 3-(2-cyclohexyloxy-1,1'-biphenyl-5-yl)propionate (Intermediate 6)

The compound of the title (440 mg) was obtained by reacting with the intermediate 1 (1.03 g), cyclohexyl alcohol (2.02 g, Tokyo Chemical Ind. Co., Ltd.), triphenylphosphine (5.27 g) and diethyl azodicarboxylate (3.50 g) according to the method described in the process c-2 in example 4.

(Process a) Synthesis of 3-(2-cyclohexyloxy-1,1'-biphenyl-5-yl)propionic Acid (Compound 05)

The compound of the title (288 mg) was obtained by reacting with the intermediate 6 (440 mg) according to the process described in the process a in example 1.

Rf=0.35 (chloroform:methanol=20:1)

Example 6

3-(2-cyclopentylmethyloxy-1,1'-biphenyl-5-yl)propionic Acid (Compound 06)

(Process c-1) Synthesis of Methyl 3-(2-cyclopentylmethyloxy-1,1'-biphenyl-5-yl)propionate (Intermediate 7)

The compound of the title (191 mg) was obtained by reacting with the intermediate 1 (256 mg), cyclopentylmethyl-p-toluenesulfonate [763 mg, prepared by reacting with cyclopenylcarbinol (Tokyo Chemical Ind. Co., Ltd.) and p-toluenesulfonyl chlorid] and sodium hydride [60.0 mg, (60% abt. In oil) Tokyo Chemical Ind. Co., Ltd.], according to the method described in the process c-1 in example 1.

(Process a) Synthesis of 3-(2-cyclopentylmethyloxy-1,1'-biphenyl-5-yl)propionic Acid (Compound 06)

The compound of the title (182 mg) was obtained by reacting with the intermediate 7 (191 mg) according to the process described in the process 3 in example 1.

Rf=0.35 (chloroform:methanol=20:1)

Example 7

3-(2-cyclohexylmethyloxy-1,1'-biphenyl-5-yl)propionic Acid (Compound 07)

(Process c-1) Synthesis of Methyl 3-(2-cyclohexylmethyloxy-1,1'-biphenyl-5-yl)propionate (Intermediate 8)

The compound of the title (642 mg) was obtained by reacting with the intermediate 1 (500 mg), bromomethyl cyclohexane (1.35 ml, Tokyo Chemical Ind. Co., Ltd.) and anhydrous potassium carbonate (337 mg) according to the method described in the process c-1 in example 1. [Proviso that the following modification was added. Reaction was carried out at 80° C. for 24 hours. Purification was performed by flush column chromatography (hexane:ethyl acetate=9:1).]

(Process a) Synthesis of 3-(2-cyclohexylmethyloxy-1,1'-biphenyl-5-yl)propionic Acid (Compound 07)

The compound of the title (595 mg) was obtained by reacting with the intermediate 8 (630 mg) according to the process described in the process a in example 1. (Proviso that the reaction was performed at 65° C. for 6 hours.)

Rf=0.35 (chloroform:methanol=20:1)

Example 8

3-[2-(2-hydroxybutyloxy)-1,1'-biphenyl-5-yl]propionic acid (compound 08)

(Process c-3) Synthesis of Methyl 3-[2-(2-hydroxybutyloxy)-1,1'-biphenyl-5-yl]propionate (Intermediate 9)

The intermediate 1 (600 mg), 1,2-butyleneoxide (1.00 ml, Tokyo Chemical Ind. Co., Ltd.) and triethylamine (1.60 ml) were added to tetrahydrofuran (10 ml) and stirred in the autoclave at 170° C. for 3 days. Reaction mixture was allowed to cool, concentrated in vacuo and added ethyl acetate (200 ml), then washed with saturated aqueous ammonium chloride solution, saturated aqueous sodium bicarbonate solution and saturated aqueous sodium chloride solution, in this order. After drying the organic layer, the solvent was distilled off in vacuo. The residue was purified by using silica gel column chromatography (hexane:ethyl acetate=5:1) to obtain the compound in the title (516 mg).

(Process a) Synthesis of 3-[2-(2-hydroxybutyloxy)-1,1'-biphenyl-5-yl]propionic Acid (Compound 08)

The compound of the title (454 mg) was obtained by reacting with the intermediate 9 (505 mg) according to the process described in the process a in example 1. (Proviso that the reaction was performed at 65° C. for 3 hours.)

Rf=0.47 (chloroform:methanol=10:1)

Example 9

Optically Active 3-[2-(2-hydroxybutyloxy)-1,1'-biphenyl-5-yl]propionic Acid (Compound 09)

(Process p) Preparative HPLC of Optically Active Methyl 3-[2-(2-hydroxybutyloxy)-1,1'-biphenyl-5-yl]propionate (Intermediate 10)

The compound in the title (184 mg) was obtained by treating with preparative HPLC using a column CHIRAL-CEL OD (2 cm×25 cm, Daicel Chem. Ind. Ltd.), in which solution prepared by dissolving the intermediate 9 (500 mg) in ethanol at 10 mg/ml was used each 100 µl for treatment. Optical purity: 97.2% ee.

Condition of preparative HPLC: Column temp. 35° C., monitored by UV absorption at 254 nm, solvent; hexane:ethanol=3.8:0.2, flow rate: 4.0 ml/min., retention time 15.9 min.

(Process a) Synthesis of Optically Active 3-[2-(2-hydroxybutyloxy)-1,1'-biphenyl-5-yl]propionic Acid (Compound 09)

The compound of the title (139 mg) was obtained by reacting with the intermediate 10 (184 mg) according to the process described in the process a in example 1.

Condition of preparative HPLC: CHIRALCEL AD (0.46 cm×25 cm, Daicel Chem. Ind. Ltd.), column temp. 35° C., monitored by UV absorption at 254 nm, solvent; hexane:ethanol:trifluoroacetic acid=85:15:0.1, flow rate: 0.5 ml/min., retention time 13.6 min. Optical purity: 96.1% ee.

Rf=0.47 (chloroform:methanol=10:1)

Example 10

Optically Active 3-[2-(2-hydroxybutyloxy)-1,1'-biphenyl-5-yl]propionic Acid (Compound 10)

(Process p) Preparative HPLC of Optically Active Methyl 3-[2-(2-hydroxybutyloxy)-1,1'-biphenyl-5-yl]propionate (Intermediate 11)

The compound in the title (201 mg) was obtained from the intermediate 9 (500 mg) according to the procedure described in the process p in example 9. Optical purity: 93.9% ee.

Condition of preparative HPLC: Column temp. 35° C., solvent; hexane:ethanol=3.8:0.2, flow rate: 4.0 ml/min., retention time 17.8 min.
(Process a) Synthesis of Optically Active 3-[2-(2-hydroxybutyloxy)-1,1'-biphenyl-5-yl]propionic Acid (Compound 10)

The compound of the title (183 mg) was obtained by reacting with the intermediate 11 (201 mg) according to the process described in the process a in example 1.

Condition of preparative HPLC: CHIRALCEL AD (0.46 cm×25 cm), column temp. 35° C., monitored by UV absorption at 254 nm, solvent; hexane:ethanol:trifluoroacetic acid 85:15:0.1, flow rate: 0.5 ml/min., retention time 14.7 min. Optical purity: 94.4% ee.

Rf=0.47 (chloroform:methanol 10:1)

Example 11

3-[2-(2-oxobutyloxy)-1,1'-biphenyl-5-yl]propionic Acid (Compound 11)
(Process c-1) Synthesis of Methyl 3-[2-(2-oxobutyloxy-1,1'-biphenyl-5-yl)propionate (Intermediate 12)

The compound of the title (1.30 g) was obtained by reacting with the intermediate 1 (1.02 g), 1-bromo-2-butanone (1.81 g, Aldrich Inc.) and anhydrous potassium carbonate (1.66 g) according to the method described in the process c-1 in example 1. [Proviso that the following modification was added. Reaction was carried out at room temperature for 3 hours. Purification was performed by flush column chromatography (hexane:ethyl acetate=5:1).]
(Process a) Synthesis of 3-[2-(2-oxobutyloxy)-1,1'-biphenyl-5-yl]propionic Acid (Compound 11)

The compound of the title (198 mg) was obtained by reacting with the intermediate 12 (326 mg) according to the process described in the process a in example 1.

Rf=0.52 (chloroform:methanol=10:1)

Example 12

3-(2-carboxymethyloxy-1,1'-biphenyl-5-yl)propionic acid (Compound 12)
(Process c-1) Synthesis of Methyl 3-(2-ethoxycarbonylmethyloxy -1,1'-biphenyl-5-yl)propionate (Intermediate 13)

The compound of the title (529 mg) was obtained by reacting with the intermediate 1 (400 mg), ethyl bromoacetate (0.52 ml, Tokyo Chemical Ind. Co., Ltd.) and anhydrous potassium carbonate (270 mg) according to the method described in the process c-1 in example 1. [Proviso that purification was performed by flush column chromatography (hexane:ethyl acetate=5:1).]
(Process a) Synthesis of 3-(2-carboxymethyloxy-1,1'-biphenyl-5-yl)propionic Acid (Compound 12)

The compound of the title (433 mg) was obtained by reacting with the intermediate 13 (505 mg) according to the process described in the process a in example 1.

Rf=0.47 (acetonitrile:acetic acid:water 100:2:1)

Example 13

3-(2-carbamoylmethyloxy-1,1'-biphenyl-5-yl)propionic Acid (Compound 13)
(Process c-1) Synthesis of Methyl 3-(2-carbamoylmethyloxy-1,1'-biphenyl-5-yl)propionate (Intermediate 14)

The compound of the title (433 mg) was obtained by reacting with the intermediate 1 (391 mg), 2-bromoacetamide (414 mg, Aldrich Inc.) and anhydrous potassium carbonate (415 mg) according to the method described in the process c-1 in example 1. [Proviso that purification was performed by flush column chromatography (chloroform:methanol=95:5).]

(Process a) Synthesis of 3-(2-carbamoylmethyloxy-1,1'-biphenyl-5-yl)propionic Acid (Compound 13)

The compound of the title (127 mg) was obtained by reacting with the intermediate 14 (319 mg) in a mixture of purified water (10 ml) and tetrahydrofuran (10 ml) with triethylamine (1.0 ml) according to the process described in the process a in example 1. (Proviso that the reaction was proceeded at room temperature for 10 days.)

Rf=0.35 (chloroform:methanol=10:1)

Example 14

3-(2-butoxy-3-nitro-1,1'-biphenyl-5-yl)propionic Acid (Compound 14)
(Process n) Synthesis of Methyl 3-(2-butoxy-3-nitro-1,1'-biphenyl-5-yl)propionate (Intermediate 15)

Previously prepared mixture of 98% fuming nitric acid (0.81 ml, d=1.52, Wako Pure Chemical Ind., Ltd.) and acetic anhydride (4.0 ml) was added dropwise to the acetic anhydride (10 ml) solution of the intermediate 2 (1.20 g) at −10° C. for 5 minutes. The reaction mixture was stirred at −10° C. for 15 minutes. Then the reaction mixture was poured into the ice-water (50 ml), neutralized with 5% aqueous sodium hydroxide solution, and extracted with isopropyl ether (150 ml×2). The organic layer was washed with saturated aqueous sodium bicarbonate solution, saturated aqueous ammonium chloride solution and saturated aqueous sodium chloride solution, in this order. The organic layer was dried and the solvent was distilled off in vacuo. The residue was purified by using flush column chromatography (hexane:ethyl acetate=7:1) to obtain the compound in the title (647 mg).
(Process a) Synthesis of 3-(2-butoxy-3-nitro-1,1'-biphenyl-5-yl)propionic Acid (Compound 14)

The compound of the title (244 mg) was obtained by reacting with the intermediate 14 (275 mg) according to the process described in the process a in example 1.

Rf=0.61 (chloroform:methanol=10:1)

Example 15

3-(3-acetylamino-2-butoxy-1,1'-biphenyl-5-yl)propionic Acid (Compound 15)
(Process m) Synthesis of Methyl 3-(3-amino-2-butoxy-1,1'-biphenyl-5-yl)propionate (Intermediate 16)

Iron powder (395 mg, Kanto Chemical Co.) and conc. HCl (0.90 ml) were added to methanol (10 ml) solution of the intermediate 15 (375 mg), and stirred at room temperature for 3 hours. Insoluble materials were removed by filtration using Celite. Ethyl acetate (200 ml) was added to the filtrate, washed with saturated aqueous sodium bicarbonate solution, saturated aqueous ammonium chloride solution and saturated aqueous sodium chloride solution, in this order. The organic layer was dried and the solvent was distilled off in vacuo. The residue was purified by using flush column chromatography (hexane:ethyl acetate=3:1) to obtain the compound in the title (350 mg).
(Process a) Synthesis of 3-(3-acetylamino-2-butoxy-1,1'-biphenyl-5-yl)propionic Acid (Compound 15)

The compound of the title (323 mg) was obtained by reacting with the intermediate 17 (345 mg) according to the process described in the process a in example 1.

Rf=0.54 (chloroform:methanol=10:1)

Example 16

3-(2-butoxy-3-methylsulfonylamino-1,1'-biphenyl-5-yl)propionic Acid (Compound 16)
(Process l-1) Synthesis of Methyl 3-(2-butoxy-3-methylsulfonylamino-1,1'-biphenyl-5-yl)propionate (Intermediate 18)

The compound of the title (513 mg) was obtained by reacting with the intermediate 16 (435 mg) and methylsulfonyl chloride (0.16 ml, Wako Pure Chemical Ind., Ltd.) in pyridine (5.0 ml) according to the method described in the process 1-1 in example 15. (Proviso that reaction was performed under ice cooling for 1 hour and at room temperature for 1 hour.)
(Process a) Synthesis of 3-(2-butoxy-3-methylsulfonylamino-1,1'-biphenyl-5-yl)propionic Acid (Compound 16)

The compound of the title (422 mg) was obtained by reacting with the intermediate 18 (465 mg) according to the process described in the process a in example 1.

Rf=0.54 (chloroform:methanol=10:1)

Example 17

3-(3-acetylamino-2-cyclohexylmethyloxy-1,1'-biphenyl-5-yl)propionic Acid (Compound 17)
(Process n) Synthesis of Methyl 3-(2-cyclohexylmethyloxy-3-nitro-1,1'-biphenyl-5-yl)propionate (Intermediate 19)

The compound of the title (892 mg) was obtained by reacting with the intermediate 8 (1.00 g) according to the method described in the process n in example 14.
(Process m) Synthesis of Methyl 3-(3-amino-2-cyclohexylmethyloxy-1,1'-biphenyl-5-yl)propionate (Intermediate 20)

The compound of the title (799 mg) was obtained by reacting with the intermediate 19 (870 mg) according to the process described in the process m in example 15.
(Process 1-1) Synthesis of Methyl 3-(3-acetylamino-2-cyclohexylmethyloxy-1,1'-biphenyl-5-yl)propionate (Intermediate 21)

The compound of the title (383 mg) was obtained by reacting with the intermediate 20 (390 mg) and acetic anhydride (0.30 ml) according to the process described in the process 1-1 in example 15.
(Process a) Synthesis of 3-(3-acetylamino-2-cyclohexylmethyloxy-1,1-biphenyl-5-yl)propionic Acid (Compound 17)

The compound of the title (347 mg) was obtained by reacting with the intermediate 21 (375 mg) according to the process described in the process a in example 1.

Rf=0.44 (chloroform:methanol=10:1)

Example 18

3-(2-cyclohexylmethoxy-3-methylsulfonylamino-1,1'-biphenyl-5-yl)propionic Acid (Compound 18)
(Process 1-1) Synthesis of Methyl 3-(2-cyclohexylmethyloxy-3-methylsulfonylamino-1,1'-biphenyl-5-yl)propionate (Intermediate 22)

The compound of the title (403 mg) was obtained by reacting with the intermediate 20 (390 mg) and methylsulfonyl chloride (0.13 ml) in pyridine (3.0 ml) according to the method described in the process 1-1 in example 15. (Proviso that reaction was performed under ice cooling for 0.5 hour and at room temperature for 0.5 hour.)
(Process a) Synthesis of 3-(2-cyclohexylmethyloxy-3-methylsulfonylamino-1,1'-biphenyl-5-yl)propionic Acid (Compound 18)

The compound of the title (364 mg) was obtained by reacting with the intermediate 22 (395 mg) according to the process described in the process a in example 1.

Rf=0.48 (chloroform:methanol=10:1)

Example 19

3-(2-cyclohexylmethyloxy-3-hydroxyacetylamino-1,1'-biphenyl-5-yl)propionic Acid (Compound 19)
(Process 1-1) Synthesis of Methyl 3-(3-acetoxyacetylamino-2-cyclohexylmethyloxy-1,1'-biphenyl-5-yl)propionate (Intermediate 23)

The compound of the title (480 mg) was obtained by reacting with the intermediate 20 (415 mg), acetoxyacetyl chloride (0.15 ml, Aldrich Inc.) and pyridine (0.10 ml) according to the method described in the process 1-1 in example 15. (Proviso that reaction was performed under ice cooling for 0.5 hour and at room temperature for 1 hour.)
(Process a) Synthesis of 3-(2-cyclohexylmethyloxy-3-hydroxyacetylamino-1,1'-biphenyl-5-yl)propionic Acid (Compound 19)

The compound of the title (394 mg) was obtained by reacting with the intermediate 23 (470 mg) according to the process described in the process a in example 1.

Rf=0.26 (chloroform:methanol=10:1)

Example 20

3-(2-cyclohexylmethyloxy-3-(N,N-dimethylcarbamoyl)amino-1,1'-biphenyl-5-yl)propionic Acid (Compound 20)
(Process 1-1) Synthesis of Methyl 3-[2-cyclohexylmethyloxy-3-(N,N-dimethylcarbamoyl)amino-1,1'-biphenyl-5-yl)propionate (Intermediate 24)

The compound of the title (278 mg) was obtained by reacting with the intermediate 20 (410 mg) and dimethylcarbamoyl chloride (0.62 ml, Tokyo Chemical Ind. Co., Ltd.) in pyridine (5.0 ml) according to the method described in the process 1-1 in example 15. (Proviso that reaction was performed under ice cooling for 0.5 hour and at room temperature for 48 hours.)
(Process a) Synthesis of 3-[2-cyclohexylmethyloxy-3-(N,N-dimethylcarbamoyl)amino-1,1'-biphenyl-5-yl)propionic Acid (Compound 20)

The compound of the title (231 mg) was obtained by reacting with the intermediate 24 (270 mg) according to the process described in the process a in example 1.

Rf=0.40 (chloroform:methanol=10:1)

Example 21

3-[2-cyclohexylmethyloxy-3-(N,N-dimethylsulfamoyl)amino-1,1'-biphenyl-5-yl)propionic Acid (Compound 21)
(Process 1-1) Synthesis of Methyl 3-[2-cyclohexylmethyloxy-3-(N,N-dimethylsulfamoyl)amino-1,1'-biphenyl-5-yl)propionate (Intermediate 25)

The compound of the title (290 mg) was obtained by reacting with the intermediate 20 (410 mg), dimethylsulfamoyl chloride (0.48 ml, Aldrich Inc.) and N,N-dimethylaminopyridine (275 mg, Tokyo Chemical Ind. Co., Ltd.) according to the method described in the process 1-1 in example 15. (Proviso that reaction was performed under ice cooling for 0.5 hour and at room temperature for 48 hours.)
(Process a) Synthesis of 3-[2-cyclohexylmethyloxy-3-(N,N-dimethylsulfamoyl)amino-1,1'-biphenyl-5-yl)propionic Acid (Compound 21)

The compound of the title (248 mg) was obtained by reacting with the intermediate 25 (280 mg) according to the process described in the process a in example 1.

Rf=0.42 (chloroform:methanol=10:1)

Example 22

3-(3-carbamoylamino-2-cyclohexylmethyloxy-1,1'-biphenyl-5-yl)propionic Acid (Compound 22)
(Process 1-2) Synthesis of Methyl 3-(3-carbamoylamino-2-cyclohexylmethyloxy-1,1'-biphenyl-5-yl)propionate (Intermediate 26)

Potassium cyanate (180 mg, Wako Pure Chemical Ind., Ltd.) was added to the solution of the intermediate 20 (410 mg) in a mixture of acetic acid (5 ml) and purified water (1 ml) and stirred at room temperature for 1 hour. The reaction mixture was poured into the ice-water (50 ml) and extracted with isopropyl ether (150 ml×2). The organic layer was washed with saturated aqueous sodium bicarbonate solution, saturated aqueous ammonium chloride solution and saturated aqueous sodium chloride solution, in this order. The organic layer was dried and the solvent was distilled off in vacuo to obtain the compound in the title (367 mg).
(Process a) Synthesis of 3-(3-carbamoylamino-2-cyclohexylmethyloxy-1,1'-biphenyl-5-yl)propionic Acid (Compound 22)

The compound of the title (293 mg) was obtained by reacting with the intermediate 26 (350 mg) according to the process described in the process a in example 1.

Rf=0.37 (acetonitrile:acetic acid:water=100:2:1)

Example 23

3-(2-cyclohexylmethyloxy-3-methoxy-1,1'-biphenyl-5-yl)propionic Acid (Compound 23)
(Process c-1) Synthesis of 4-cyclohexylmethyloxy-3-iodo-5-methoxybenzaldehyde (Intermediate 27)

The compound in the title (749 mg) was obtained by reacting with 5-iodovanillin (556 mg, Aldrich Inc.), bromomethyl cyclohexane (1.77 g) and potassium carbonate anhydride (1.38 g) according to a process described in the process c-1 in example 1.
(Process i) Synthesis of 4-cyclohexylmethyloxy-5-methoxy-3-phenylbenzaldehyde (Intermediate 28)

The intermediate 27 (749 mg), phenyl boric acid (1.22 g, Tokyo Chemical Ind. Co., Ltd.), potassium carbonate (1.38 g) and tetrakis (triphenylphosphine)palladium (0)(462 mg, Tokyo Chemical Ind. Co., Ltd.) were added to toluene (5 ml) and stirred at 100° C. for 12 hours under argon atmosphere. The reaction mixture was cooled and water (50 ml) was added thereto, then extracted with ethyl acetate (50 ml×3). The organic layer was washed with saturated aqueous ammonium chloride solution and saturated aqueous sodium chloride solution in this order, and dried. The solvent was removed off in vacuo and the residue was purified using flush column chromatography (hexane:ethyl acetate=9 1) to obtain the compound in the title (650 mg).
(Process h) Synthesis of Ethyl 3-(2-cyclohexylmethyloxy-3-methoxy-1,1'-biphenyl-5-yl)acrylate (Intermediate 29)

Ethyl diethylphosphono acetate (896 mg, Tokyo Chemical Ind. Co., Ltd.) and sodium hydride (160 mg) were added to 1,2-dimethoxyethane (10 ml) at 0° C. under argon atmosphere and stirred. Intermediate 28 (650 mg) was added, when hydrogen gas generation was stopped, and stirred at room temperature for 1 hour. The reaction mixture was washed with saturated aqueous ammonium chloride solution, dried and distilled off the solvent in vacuo. The residue was purified with flush column chromatography (hexane:ethyl acetate=9:1) to obtain the compound in the title (785 mg).
(Process g) Synthesis of Ethyl 3-(2-cyclohexylmethyloxy-3-methoxy-1,1'-biphenyl-5-yl)propionate (Intermediate 30)

The intermediate 29 (785 mg) and 10% palladium carbon powder (50 mg, Merck) were added to ethanol (5 ml), and stirred at room temperature for 3 hours under hydrogen atmosphere. The reaction mixture was filtered and the solvent was removed off in vacuo to obtain the compound in the title (753 mg).
(Process a) Synthesis of 3-(2-cyclohexylmethyloxy-3-methoxy-1,1'-biphenyl-5-yl)propionic Acid (Compound 23)

The compound of the title (668 mg) was obtained by reacting with the intermediate 30 (753 mg) according to the process described in the process a in example 1.

Rf=0.53 (chloroform:methanol=10:1)

Example 24

3-(2-cyclohexylmethyloxy-3-hydroxy-1,1'-biphenyl-5-yl)propionic Acid (Compound 24)
(Process c-2) Synthesis of Methyl 3-(2-cyclohexylmethyloxy-3-hydroxy-1,1'-biphenyl-5-yl)propionate (Intermediate 31)

The compound of the title (334 mg) was obtained by reacting with the compound 23 (334 mg), pyridine (7 ml), conc. HCl (7 ml) and thionyl chloride (238 mg) according to the method described in the process d in example 1.
(Process a) Synthesis of 3-(2-cyclohexylmethyloxy-3-hydroxy-1,1'-biphenyl-5-yl)propionic Acid (Compound 24)

The compound of the title (120 mg) was obtained by reacting with the intermediate 31 (151 mg) according to the process described in the process a in example 1.

Rf=0.38 (chloroform:methanol=10:1)

Example 25

3-(2-cyclohexylmethyloxy-4'-hydroxy-1,1'-biphenyl-5-yl)propionic Acid (Compound 25)
(Process c-1) Synthesis of 3-bromo-4-cyclohexylmethyloxy Benzaldehyde (Intermediate 32)

The compound in the title (1.97 g) was obtained by reacting with 3-bromo-4-hydroxybenzaldehyde [1.51 g, prepared from 3-bromo-p-anisaldehyde (Aldrich Inc.) using pyridine hydrochloric acid complex described in the process d in example 1], bromomethyl cyclohexane (3.34 g) and anhydride potassium carbonate (2.61 g) according to a process described in the process c-1 in example 1.
(Process i) Synthesis of 3-(4'-benzyloxyphenyl)-4-cyclohexylmethyloxy Benzaldehyde (Intermediate 33)

The intermediate 32 (1.76 g), 4-benzyloxyphenyl boric acid [6.75 g, 4-benzyloxy bromobenzene was prepared according to a process described in the process c-1 in example 1 from 4-bromophenol (Tokyo Chemical Ind. Co., Ltd.) and benzyl chloride (Tokyo Chemical Ind. Co., Ltd.), and the product was prepared according to a method described in the reference Y Satoh et al. SYNTHESIS page 1146, 1994], anhydrous potassium carbonate (4.09 g) and tetrakis (triphenylphosphine)palladium (0)(342 mg) were reacted according to the method described in the process i in example 23 to obtain the compound in the title (2.30 g).
(Process h) Synthesis of Methyl 3-(4'-benzyloxy-2-cyclohexylmethyloxy-1,1'-biphenyl-5-yl)acrylate (Intermediate 34)

The intermediate 33 (2.30 g), ethyl diethylphosphono acetate (1.99 g) and 28% methanol solution of sodium methoxide (1.75 ml, Wako Pure Chemical Ind., Ltd.) were reacted according to the process described in the process h in example 23 to obtain the compound in the title (1.45 g).
(Process g) Synthesis of Methyl 3-(2-cyclohexylmethyloxy-4'-hydroxy-1,1'-biphenyl-5-yl)propionate (Intermediate 35)

The intermediate 34 (1.45 g) and 10% palladium carbon powder (300 mg) were reacted under hydrogen atmosphere according to the method described in the process g in example 23 to obtain the compound in the title (1.13 g). Proviso that methanol was used as the solvent.
(Process a) Synthesis of 3-(2-cyclohexylmethyloxy-4'-hydroxy-1,1'-biphenyl-5-yl)propionic Acid (Compound 25)

The compound of the title (1.09 g) was obtained by reacting with the intermediate 35 (1.13 g) according to the process described in the process a in example 1.

Rf=0.36 (chloroform:methanol=10:1)

Example 26

3-(2-cyclohexylmethyloxy-4'-methoxy-1,1'-biphenyl-5-yl)propionic Acid (Compound 26)
(Process i) Synthesis of 3-(4'-methoxyphenyl)-4-cyclohexylmethyloxy Benzaldehyde (Intermediate 36)

The intermediate 32 (2.00 g), 4-methoxyphenyl boric acid (500 mg, Aldrich Inc.), potassium carbonate anhydride (464 mg) and tetrakis (triphenylphosphine)palladium (0)(39 mg) were reacted according to the method described in the process i in example 23 to obtain the compound in the title (218 mg).

(Process h) Synthesis of Methyl 3-(2-cyclohexylmethyloxy-4'-methoxy-1,1'-biphenyl-5-yl)acrylate (Intermediate 37)

The intermediate 36 (218 mg), ethyl diethylphosphono acetate (226 mg) and 28% methanol solution of sodium methoxide (0.21 ml) were reacted according to the process described in the process h in example 23 to obtain the compound in the title (245 mg). Proviso that methanol was used as the solvent.

(Process g) Synthesis of Methyl 3-(2-cyclohexylmethyloxy-4'-methoxy-1,1'-biphenyl-5-yl)propionate (Intermediate 38)

The intermediate 38 (245 mg), ammonium formate (163 mg, Wako Pure Chemical Ind., Ltd.) and 10% palladium carbon powder (25 mg) were reacted under according to the method described in the process g in example 23 to obtain the compound in the title (238 mg).

(Process a) Synthesis of 3-(2-cyclohexylmethyloxy-4'-methoxy-1,1'-biphenyl-5-yl)propionic Acid (Compound 26)

The compound of the title (229 mg) was obtained by reacting with the intermediate 38 (238 mg) according to the process described in the process a in example 1.

Rf=0.56 (chloroform:methanol=10:1)

Example 27

3-(2-cyclohexylmethyloxy-1,1-biphenyl-5-yl)propionamide (Compound 27)

(Process b-1) Synthesis of 3-(2-cyclohexylmethyloxy-1,1-biphenyl-5-yl)propionamide (Compound 27)

N,N-dimethylformamide (one drop) and thionyl chloride (0.35 ml) were added to toluene (4 ml) solution of the compound 7 (400 mg) and refluxed for 1 hour. After the reaction mixture was concentrated in vacuo, toluene (2 ml) was added and subjected to azeotropic drying in vacuo (twice). Residual tetrahydrofuran (2 ml) was added dropwise to 25% aqueous ammonia (5.0 ml) under ice-cooling, and stirred for 1 hour. Ethyl acetate (200 ml) was added to the reaction mixture. The reaction mixture was washed with saturated aqueous sodium bicarbonate solution, saturated aqueous ammonium chloride solution and saturated aqueous sodium chloride solution, in this order. The organic layer was dried and the solvent was distilled off in vacuo to obtain the compound in the title (391 mg).

Rf=0.36 (chloroform:methanol=10:1)

Example 28

4-(2-butoxy-1,1'-biphenyl-5-yl)butyric Acid (Compound 28)

(Process f) Synthesis of Methyl 4-(2-methoxy-1,1'-biphenyl-5-yl)-4-oxo Butyrate (Intermediate 39)

A solution of aluminum chloride (2.68 g, purity 99.99%, Aldrich Inc.) suspended in methylene chloride (50 ml) was stirred at 0° C. Methylene chloride (5 ml) solution of 3-carbomethoxypropionyl chloride (3.01 g, Aldrich Inc.) was added thereto and stirred at 0° C. for 10 minutes. Methylene chloride (20 ml) solution of 2-methoxybiphenyl (2.00 g, Aldrich Inc.) was added dropwise for 20 minutes and stirred at 0° C for 30 minutes and later at room temperature for 3 hours. Reaction mixture was poured into ice-cold 3 N—HCl (150 ml), vigorously stirred and extracted with methylene chloride (50 ml×3). The organic layer was washed with water, aqueous saturated sodium bicarbonate solution, water and aqueous saturated sodium chloride solution, in this order, then the organic layer was dried and distilled of in vacuo to obtain the compound in the title (2.81 g).

(Process e) Synthesis of Methyl 4-(2-methoxy-1,1'-biphenyl-5-yl)butyrate (Intermediate 40)

The intermediate 39 (2.02 g), conc. HCl (4 drops) and 10% palladium carbon powder (1.01 g) were added to a mixture of methylene chloride and methanol (1:2) (30 ml) and stirred at room temperature for overnight under hydrogen atmosphere. The reaction mixture was filtered and the solvent was distilled off. The residue was purified by flush column chromatography (hexane:ethyl acetate=12:1) to obtain the compound in the title (1.82 g).

(Process c-2) Synthesis of Methyl 4-(2-hydroxy-1,1'-biphenyl-5-yl)butyrate (Intermediate 41)

The compound in the title (389 mg) was obtained by reacting with the intermediate 40 (603 mg), pyridine (10 ml), conc. HCl (10 ml), methanol (5 ml) and thionyl chloride (505 mg) according to the method described in the process d in example 1.

(Process c-1) Synthesis of Methyl 4-(2-butoxy-1,1'-biphenyl-5-yl)butyrate (Intermediate 42)

The intermediate 41 (300 mg), butane iodide (404 mg) and anhydride potassium carbonate (277 mg) were reacted according to the process described in the process c-1 in example 1 to obtain the compound of the title (344 mg).

(Process a) Synthesis of 4-(2-butoxy-1,1'-biphenyl-5-yl) butyric Acid (Compound 28)

The compound of the title (175 mg) was obtained by reacting the intermediate 42 (285 mg) according to the process described in the process a in example 1.

Rf=0.38 (chloroform:methanol=20:1).

Example 29

4-(2-isobutoxy-1,1'-biphenyl-5-yl)butyric Acid (Compound 29)

(Process c-1) Synthesis of Methyl 4-(2-isobutoxy-1,1'-biphenyl-5-yl)butyrate (Intermediate 43)

The compound of the title (585 mg) was obtained by reacting with the intermediate 41(540 mg), isobutyl bromide (1.37 g) and anhydrous potassium carbonate (1.38 g) according to the method described in the process c-1 in example 1.

(Process a) Synthesis of 4-(2-isobutoxy-1,1'-biphenyl-5-yl) butyric Acid (Compound 29)

The compound of the title (561 mg) was obtained by reacting with the intermediate 43 (585 mg) according to the process described in the process a in example 1.

Rf=0.38 (chloroform:methanol=20:1)

Example 30

4-[2-(1-methylpropyloxy)-1,1'-biphenyl-5-yl]butyric Acid (Compound 30)

(Process c-1) Synthesis of Methyl 4-[2-(1-methylpropyloxy)-1,1'-biphenyl-5-yl)butyrate (Intermediate 44)

The compound of the title (140 mg) was obtained by reacting with the intermediate 41 (250 mg), 2-iodo butane (1.84 g, Tokyo Chemical Ind. Co., Ltd.) and anhydrous potassium carbonate (690 mg) according to the method described in the process c-1 in example 1.

(Process a) Synthesis of 4-[2-(1-methylpropyloxy)-1,1'-biphenyl-5-yl)butyric Acid (Compound 30)

The compound of the title (123 mg) was obtained by reacting with the intermediate 44 (140 mg) according to the process described in the process a in example 1.

Rf=0.37 (chloroform:methanol=20:1)

Example 31

4-(2-pentyloxy-1,1'-biphenyl-5-yl)butyric Acid (Compound 31)

(Process c-1) Synthesis of Methyl 4-(2-pentyloxy-1,1'-biphenyl-5-yl)butyrate (Intermediate 45)

The compound of the title (340 mg) was obtained by reacting with the intermediate 41 (270 mg), iodo pentane (910 mg) and potassium carbonate anhydride (680 mg) according to the method described in the process c-1 in example 1.
(Process a) Synthesis of 4-(2-pentyloxy-1,1'-biphenyl-5-yl)butyric Acid (Compound 31)

The compound of the title (251 mg) was obtained by reacting with the intermediate 45 (340 mg) according to the process described in the process a in example 1.

Rf=0.38 (chloroform:methanol=20:1)

Example 32

4-[2-(1-methylbutyloxy)-1,1'-biphenyl-5-yl]butyric Acid (Compound 32)
(Process c-1) Synthesis of Methyl 4-[2-(1-methylbutyloxy)-1,1'-biphenyl-5-yl]butyrate (Intermediate 46)

The compound of the title (464 mg) was obtained by reacting with the intermediate 41 (540 mg), 2-bromo pentane (1.51 g, Tokyo Chemical Ind. Co., Ltd.) and potassium carbonate anhydride (1.38 g) according to the method described in the process c-1 in example 1.
(Process a) Synthesis of 4-[2-(1-methylbutyloxy)-1,1'-biphenyl-5-yl]butyric Acid (Compound 32)

The compound of the title (434 mg) was obtained by reacting with the intermediate 48 (454 mg) according to the process described in the process a in example 1.

Rf=0.38 (chloroform:methanol=20:1)

Example 33

4-[2-(2-methylbutoxy)-1,1'-biphenyl-5-yl]butyric Acid (Compound 33)
(Process c-1) Synthesis of Methyl 4-[2-(2-methylbutoxy)-1,1'-biphenyl-5-yl]butyrate (Intermediate 47)

The compound of the title (495 mg) was obtained by reacting with the intermediate 41 (503 mg), sodium hydride (75.0 mg) and 2-methyl-1-(p-toluenesulfonyl)butane [528 mg, prepared from 2-methyl-1-butanol (Tokyo Chemical Ind. Co., Ltd.) and p-toluenesulfonyl chloride in pyridine] according to the method described in the process c-1 in example 1.
(Process a) Synthesis of 4-[2-(2-methylbutoxy)-1,1'-biphenyl-5-yl]butyric Acid (Compound 33)

The compound of the title (455 mg) was obtained by reacting with the intermediate 47 (495 mg) according to the process described in the process a in example 1.

Rf=0.36 (chloroform:methanol=20:1)

Example 34

4-(2-isopentyloxy-1,1'-biphenyl-5-yl)butyric Acid (Compound 34)
(Process c-1) Synthesis of Methyl 4-(2-isopentyloxy-1,1'-biphenyl-5-yl)butyrate (Intermediate 48)

The compound of the title (680 mg) was obtained by reacting with the intermediate 41(540 mg), 1-bromo-3-methylbutane (1.51 g, Tokyo Chemical Ind. Co., Ltd.) and potassium carbonate anhydride (1.38 g) according to the method described in the process c-1 in example 1.
(Process a) Synthesis of 4-(2-isopentyloxy-1,1'-biphenyl-5-yl)butyric Acid (Compound 34)

The compound of the title (642 mg) was obtained by reacting with the intermediate 48 (670 mg) according to the process described in the process a in example 1.

Rf=0.35 (chloroform:methanol=20:1)

Example 35

4-(2-cyclopentyloxy-1,1'-biphenyl-5-yl)butyric Acid (Compound 35)
(Process c-2) Synthesis of Methyl 4-(2-cyclopentyloxy-1,1'-biphenyl-5-yl)butyrate (Intermediate 49)

The compound of the title (900 mg) was obtained by reacting with the intermediate 41 (1.00 g), cyclopentyl alcohol (1.59 g), triphenylphosphine (4.85 g) and diethyl azodicarboxylate (3.22 g) according to the method described in the process c-2 in example 4.
(Process a) Synthesis of 4-(2-cyclopentyloxy-1,1'-biphenyl-5-yl)butyric Acid (Compound 35)

The compound of the title (781 mg) was obtained by reacting with the intermediate 49 (900 mg) according to the process described in the process a in example 1.

Rf=0.37 (chloroform:methanol=20:1)

Example 36

4-(2-cyclohexyloxy-1,1'-biphenyl-5-yl)butyric Acid (Compound 36)
(Process c-2) Synthesis of Methyl 4-(2-cyclohexyloxy-1,1'-biphenyl-5-yl)butyrate (Intermediate 50)

The compound of the title (630 mg) was obtained by reacting with the intermediate 41 (1.04 g), cyclohexyl alcohol (1.92 g), triphenylphosphine (5.05 g) and diethyl azodicarboxylate (3.35 g) according to the method described in the process c-2 in example 4.
(Process a) Synthesis of 4-(2-cyclohexyloxy-1,1'-biphenyl-5-yl)butyric Acid (Compound 36)

The compound of the title (514 mg) was obtained by reacting with the intermediate 50 (630 mg) according to the process described in the process a in example 1.

Rf=0.38 (chloroform:methanol=20:1)

Example 37

4-(2-cyclopentylmethyloxy-1,1'-biphenyl-5-yl)butyric Acid (Compound 37)
(Process c-1) Synthesis of Methyl 4-(2-cyclopentylmethyloxy-1,1'-biphenyl-5-yl)butyrate (Intermediate 51)

The compound of the title (140 mg) was obtained by reacting with the intermediate 41 (270 mg), sodium hydride (52.0 mg, 60% abt. in oil) and cyclopentylmethyl-p-toluenesulfonate (355 mg) according to the method described in the process c-1 in example 1.
(Process a) Synthesis of 4-(2-cyclopentylmethyloxy-1,1'-biphenyl-5-yl)butyric Acid (Compound 37)

The compound of the title (124 mg) was obtained by reacting with the intermediate 51 (140 mg) according to the process described in the process a in example 1.

Rf=0.38 (chloroform:methanol=20:1)

Example 38

4-(2-cyclohexylmethyloxy-1,1'-biphenyl-5-yl)butyric Acid (Compound 38)
(Process c-1) Synthesis of Methyl 4-(2-cyclohexylmethyloxy-1,1'-biphenyl-5-yl)butyrate (Intermediate 52)

The compound of the title (336 mg) was obtained by reacting with the intermediate 41 (250 mg), bromomethyl cyclohexane (885 mg) and potassium carbonate anhydride (690 mg) according to the method described in the process c-1 in example
(Process a) Synthesis of 4-(2-cyclohexylmethyloxy-1,1'-biphenyl-5-yl)butyric Acid (Compound 38)

The compound of the title (291 mg) was obtained by reacting with the intermediate 52 (336 mg) according to the process described in the process a in example 1.

Rf=0.38 (chloroform:methanol=20:1)

Example 39

4-[2-(4-hydroxybutyloxy)-1,1'-biphenyl-5-yl]butyric Acid (Compound 39)
(Process c-1) Synthesis of Methyl 4-[2-(4-acetyloxybutyloxy)-1,1'-biphenyl-5-yl]butyrate (Intermediate 53)

The compound of the title (1.53 g) was obtained by reacting with the intermediate 41 (1.08 g), 4-bromobutyl acetate (3.90 g, Aldrich Inc.) and potassium carbonate anhydride (2.76 g) according to the method described in the process c-1 in example 1.
(Process a) Synthesis of 4-[2-(4-hydroxybutyloxy)-1,1'-biphenyl-5-yl]butyric Acid (Compound 39)

The compound of the title (1.18 g) was obtained by reacting with the intermediate 53 (1.98 g) according to the process described in the process a in example 1.

Rf=0.50 (chloroform:methanol=10:1)

Example 40

4-[2-(3-hydroxybutyloxy)-1,1'-biphenyl-5-yl]butyric Acid (Compound 40)
(Process c-1) Synthesis of Methyl 4-[2-(3-acetyloxybutyloxy)-1,1'-biphenyl-5-yl]butyrate (Intermediate 54)

The compound of the title (482 mg) was obtained by reacting with the intermediate 41 (454 mg), sodium hydride (67.2 mg, 60% abt. in oil) and 3-acetyloxy-1-mesitylenesulfonyl butane [528 mg, obtained from reaction of 3-hydroxy-1-mesitylenesulfonyl butane, which was prepared from 1,3-butane diol (Tokyo Chemical Ind. Co., Ltd.) and 2-mesitylenesulfonyl chloride (Tokyo Chemical Ind. Co., Ltd.), with acetic anhydride in pyridine] according to the method described in the process c-1 in example 1.
(Process a) Synthesis of 4-[2-(3-hydroxybutyloxy)-1,1'-biphenyl-5-yl]butyric Acid (Compound 40)

The compound of the title (402 mg) was obtained by reacting with the intermediate 54 (480 mg) according to the process described in the process a in example 1.

Rf=0.49 (chloroform:methanol=10:1)

Example 41

4-[2-(2-hydroxybutyloxy)-1,1'-biphenyl-5-yl]butyric Acid (Compound 41)
(Process c-3) Synthesis of Methyl 4-[2-(2-hydroxybutyloxy)-1,1'-biphenyl-5-yl]butyrate (Intermediate 55)

The compound of the title (188 mg) was obtained by reacting with the intermediate 41 (1.35 g), triethylamine (2.5 ml) and 1,2-butyleneoxide (720 mg) according to the method described in the process c-3 in example 8.
(Process a) Synthesis of 4-[2-(2-hydroxybutyloxy)-1,1'-biphenyl-5-yl]butyric Acid (Compound 41)

The compound of the title (180 mg) was obtained by reacting with the intermediate 55 (188 mg) according to the process described in the process a in example 1.

Rf=0.48 (chloroform:methanol=10:1)

Example 42

Optically Active 4-[2-(2-hydroxybutyloxy)-1,1'-biphenyl-5-yl]butyric Acid (Compound 42)
(Process p) Preparative HPLC of Optically Active Methyl 4-[2-(2-hydroxybutyloxy)-1,1'-biphenyl-5-yl]butyrate (Intermediate 56)

The compound in the title (136 mg) was obtained from the intermediate 55 (500 mg) according to the method described in the process p in example 9.

Optical purity: 98.3%ee. Condition of preparative HPLC: CHIRALCEL OD (2 cm×25 cm) column, column temp. 35° C., monitored by UV absorption at 254 nm, solvent; hexane:ethanol=3.8:0.2, flow rate: 4.0 ml/min., retention time: 15.7 min.
(Process a) Synthesis of Optically Active 4-[2-(2-hydroxybutyloxy)-1,1'-biphenyl-5-yl]butyric Acid (Compound 42)

The compound in the title (128 mg) was obtained by reacting with the intermediate 56 (136 mg) according to the process described in the process a in example 1.

Condition for analysis: CHIRALCEL AD (0.46 cm×25 cm) column, column temp. 35° C, monitored by UV absorption at 254 nm, solvent; hexane:ethanol trifluoroacetic acid= 85:15:0.1, flow rate: 0.5 ml/min., retention time: 16 min., optical purity: 98.3%ee.

Rf=0.48 (chloroform:methanol=10:1)

Example 43

Optically Active 4-[2-(2-hydroxybutyloxy)-1,1'-biphenyl-5-yl]butyric Acid (Compound 43)
(Process p) Preparative HPLC of Optically Active Methyl 4-[2-(2-hydroxybutyloxy)-1,1'-biphenyl-5-yl]butyrate (Intermediate 57)

The compound in the title (138 mg) was obtained from the intermediate 55 (500 mg) according to the method described in the process p in example 9.

Optical purity: 94.2%ee. Condition of preparative HPLC: CHIRALCEL OD (2 cm×25 cm) column, column temp. 35° C., monitored by UV absorption at 254 nm, solvent; hexane:ethanol=3.8:0.2, flow rate: 4.0 ml/min., retention time: 17.9 min.
(Process a) Synthesis of Optically Active 4-[2-(2-hydroxybutyloxy)-1,1'-biphenyl-5-yl]butyric Acid (Compound 43)

The compound in the title (129 mg) was obtained by reacting with the intermediate 57 (138 mg) according to the process described in the process a in example 1.

Condition for analysis: CHIRALCEL AD (0.46 cm×25 cm) column, column temp. 35° C., monitored by UV absorption at 254 nm, solvent; hexane:ethanol trifluoroacetic acid= 85:15:0.1, flow rate: 0.5 ml/min., retention time: 14.6 min., optical purity: 95.8%ee.

Rf=0.48 (chloroform:methanol=10:1)

Example 44

4-(2-carboxymethyloxy-1,1'-biphenyl-5-yl)butyric Acid (Compound 44)
(Process c-1) Synthesis of Methyl 4-(2-methoxycarbonymethyloxy-1,1'-biphenyl-5-yl)butyrate (Intermediate 58)

The compound in the title (399 mg) was obtained by reacting the intermediate 41 (400 mg), methyl bromoacetate (1.13 g, Tokyo Chemical Ind. Co., Ltd.) and potassium carbonate anhydride (1.03 g) according to the method described in the process c-1 in example 1.
(Process a) Synthesis of 4-(2-carboxymethyloxy-1,1'-biphenyl-5-yl)butyric Acid (Compound 44)

The compound in the title (367 mg) was obtained by reacting with the intermediate 58 (399 mg) according to the process described in the process a in example 1.

Rf=0.4 (acetonitrile:acetic acid:water=100:2:1)

Example 45

4-[2-(2-carboxyethyloxy)-1,1'-biphenyl-5-yl]butyric Acid (Compound 45)
(Process c-4) Synthesis of Methyl 4-[2-(2-cyanoethyloxy)-1,1'-biphenyl-5-yl]butyrate (Intermediate 59)

The intermediate 41 (500 mg) and copper hydroxide (10.0 mg, Kanto Chemical Co.) were added to acrylonitrile (4 ml, Tokyo Chemical Ind. Co., Ltd.) and refluxed. After 4 hours, triethylamine (4 drops) was added, and after 8 hours, toluene (5 ml) was added, then further refluxed for 24 hours. The reaction mixture was cooled and acrylonitrile was distilled off in vacuo. The residue was purified by flush column chromatography (hexane:ethyl acetate=5:1) to obtain the compound in the title (206 mg).

(Process a) Synthesis of 4-[2-(2-carboxyethyloxy)-1,1'-biphenyl-5-yl]butyric Acid (Compound 45)

The compound in the title (203 mg) was obtained by reacting with the intermediate 59 (206 mg) according to the process described in the process a in example 1.

Rf=0.21 (chromoform:methanol=10:1)

Example 46

4-[2-(3-carboxypropyloxy)-1,1'-biphenyl-5-yl]butyric Acid (Compound 46)
(Process c-1) Synthesis of Methyl 4-[2-(3-ethoxycarbonylpropyloxy)-1,1'-biphenyl-5-yl]butyrate (Intermediate 60)

The compound in the title (541 mg) was obtained by reacting the intermediate 41 (400 mg), ethyl 4-bromobutylate (1.44 g, Aldrich Inc.) and potassium carbonate anhydride (1.03 g) according to the method described in the process c-1 in example 1.
(Process a) Synthesis of 4-[2-(3-carboxypropyloxy)-1,1'-biphenyl-5-yl]butyric Acid (Compound 46)

The compound in the title (312 mg) was obtained by reacting with the intermediate 60 (531 mg) according to the process described in the process a in example 1.

Rf=0.33 (chloroform:methanol 10:1)

Example 47

4-(2-carbamoylmethyloxy-1,1'-biphenyl-5-yl)butyric Acid (Compound 47)
(Process c-1) Synthesis of Methyl 4-(2-carbamoylmethyloxy-1,1'-biphenyl-5-yl)butyrate (Intermediate 61)

The compound in the title (568 mg) was obtained by reacting the intermediate 41 (540 mg), 2-bromoacetamide (1.38 g) and potassium carbonate anhydride (415 mg) according to the method described in the process c-1 in example 1.
(Process a) Synthesis of 4-(2-carbamoylmethyloxy-1,1'-biphenyl-5-yl)butyric Acid (Compound 47)

The compound in the title (117 mg) was obtained by reacting the intermediate 61 (274 mg) with triethylamine (2.0 ml) in the mixture of purified water (4 ml) and tetrahydrofuran (10 ml) according to the process described in the process a in example 1. Proviso that the reaction was carried out for 10 days.

Rf=0.36 (chloroform:methanol=10:1)

Example 48

4-[2-(N,N-dimethylcarbamoylmethyloxy)-1,1'-biphenyl-5-yl]butyric acid (Compound 48)
(Process c-1) Synthesis of Methyl 4-[2-(N,N-dimethylcarbamoylmethyloxy)-1,1'-biphenyl-5-yl]butyrate (Intermediate 62)

The compound in the title (455 mg) was obtained by reacting the intermediate 41 (350 mg), 2-chloro-N,N-dimethylacetamide (472 mg, Merck) and potassium carbonate anhydride (536 mg) according to the method described in the process c-1 in example 1.
(Process a) Synthesis of 4-[2-(N,N-dimethylcarbamoylmethyloxy)-1,1'-biphenyl-5-yl]butyric Acid (Compound 48)

The compound in the title (366 mg) was obtained by reacting the intermediate 62 (455 mg) with triethylamine (2.0 ml) in the mixture of purified water (2 ml) and tetrahydrofuran (10 ml) according to the process described in the process a in example 1. Proviso that the reaction was carried out for 10 days. Rf 0.60 (chloroform:methanol=10:1)

Example 49

4-[2-(N,N-diethylcarbamoylmethyloxy)-1,1'-biphenyl-5-yl]butyric Acid (Compound 49)
(Process c-1) Synthesis of Methyl 4-[2-(N,N-diethylcarbamoylmethyloxy)-1,1'-biphenyl-5-yl]butyrate (Intermediate 63)

The compound in the title (503 mg) was obtained by reacting the intermediate 41 (354 mg), 2-chloro-N,N-diethylacetamide (581 mg, Aldrich Inc.) and potassium carbonate anhydride (536 mg) according to the method described in the process c-1 in example 1.
(Process a) Synthesis of 4-[2-(N,N-diethylcarbamoylmethyloxy)-1,1'-biphenyl-5-yl]butyric Acid (Compound 49)

The compound in the title (344 mg) was obtained by reacting the intermediate 63 (503 mg) with triethylamine (2.0 ml) in the mixture of purified water (2 ml) and tetrahydrofuran (10 ml) according to the process described in the process a in example 1. Proviso that the reaction was carried out for 10 days.

Rf=0.62 (chloroform:methanol=10:1)

Example 50

4-(2-butoxy-3-nitro-1,1'-biphenyl-5-yl)butyric Acid (Compound 50)
(Process n) Synthesis of Methyl 4-(2-butoxy-3-nitro-1,1'-biphenyl-5-yl)butyrate (Intermediate 64)

The compound in the title (534 mg) was obtained by reacting with the intermediate 42 (652 mg) according to the process described in the process n in example 14.
(Process a) Synthesis of 4-(2-butoxy-3-nitro-1,1'-biphenyl-5-yl)butyric Acid (Compound 50)

The compound in the title (272 mg) was obtained by reacting with the intermediate 64 (310 mg) according to the process described in the process a in example 1.

Rf=0.62 (chloroform:methanol=10:1)

Example 51

4-(2-butoxy-3-formylamino-1,1'-biphenyl-5-yl)butyric Acid (Compound 51)
(Process m) Synthesis of Methyl 4-(3-amino-2-butoxy-1,1'-biphenyl-5-yl)butyrate (Intermediate 65)

The compound in the title (1.45 g) was obtained by reacting with the intermediate 64 (1.59 g) according to the process described in the process m in example 15.
(Process 1-1) Synthesis of Methyl 4-(2-butoxy-3-formylamino-1,1'-biphenyl-5-yl)butyrate (Intermediate 66)

The compound in the title (376 mg) was obtained by reacting the intermediate 65 (380 mg) and previously mixed 99% formic acid (1.0 ml) and acetic anhydride (0.32 ml) according to the process described in the process 1-1 in example 15.
(Process a) Synthesis of 4-(2-butoxy-3-formylamino-1,1'-biphenyl-5-yl)butyric Acid (Compound 51)

The compound in the title (345 mg) was obtained by reacting with the intermediate 66 (360 mg) according to the process described in the process a in example 1.

Rf=0.50 (chloroform:methanol=10:1)

Example 52

4-(3-acetylamino-2-butoxy-1,1'-biphenyl-5-yl)butyric Acid (Compound 52)
(Process 1-1) Synthesis of Methyl 4-(3-acetylamino-2-butoxy-1,1'-biphenyl-5-yl)butyrate (Intermediate 67)

The compound in the title (1.50 g) was obtained by reacting the intermediate 65 (1.45 g) with acetic anhydride (1.20 ml) according to the process described in the process 1-1 in example 15.

(Process a) Synthesis of 4-(3-acetylamino-2-butoxy-1,1'-biphenyl-5-yl)butyric Acid (Compound 52)

The compound in the title (1.27 g) was obtained by reacting with the intermediate 67 (1.50 g) according to the process described in the process a in example 1.

Rf=0.55 (chloroform:methanol=10:1)

Example 53

4-(2-butoxy-3-methylsulfonylamino-1,1'-biphenyl-5-yl)butyric Acid (Compound 53)

(Process 1-1) Synthesis of Methyl 4-(2-butoxy-3-methylsulfonylamino-1,1'-biphenyl-5-yl)butyrate (Intermediate 68)

The compound in the title (420 mg) was obtained by reacting the intermediate 65 (380 mg) with methylsulfonyl chloride (0.13 ml) in pyridine (3.0 ml) according to the method described in the process 1-1 in example 15. (Proviso that the reaction was performed under ice-cooling for 0.5 hour and at room temperature for 1 hour).

(Process a) Synthesis of 4-(2-butoxy-3-methylsulfonylamino-1,1'-biphenyl-5-yl)butyric Acid (Compound 53)

The compound in the title (370 mg) was obtained by reacting with the intermediate 68 (405 mg) according to the process described in the process a in example 1.

Rf=0.55 (chloroform:methanol=10:1)

Example 54

4-(2-butoxy-3-methoxy-1,1'-biphenyl-5-yl)butyric Acid (Compound 54)

(Process k) Synthesis of 2-methoxy-3-methoxybiphenyl (Intermediate 69) 2-methoxymethyloxyanisole [5.23 g, prepared from 2-methoxyphenol (Tokyo Chemical Ind. Co., Ltd.), chloromethylmethyl ether (Tokyo Chemical Ind. Co., Ltd.) and potassium carbonate anhydride according to the method described in the process c-1 in example 1]was added to anhydrous THF (30 ml) and stirred under argon atmosphere at −78° C. Hexane solution (21.4 ml, Wako Pure Chem. Co.) of 1.6 molar concentration of n-butyl lithium was added thereto and stirred for 1 hour. The reaction mixture was gradually changed to room temperature and stirred for 30 minutes. THF solution of 0.5 molar concentration of zinc chloride (62.0 ml, Aldrich Inc.) was added thereto and stirred at room temperature for 80 minutes. Anhydrous THF solution (10 ml) of iodo benzene (6.34 g, Tokyo Chemical Ind. Co., Ltd.) and tetrakis (triphenylphosphine)palladium (0)(1.79 g) and stirred for 16 hours under light shield condition. The reaction mixture was poured into 1 N—HCl solution (100 ml) and extracted with ethyl acetate (100 ml×3). The organic layer was washed with saturated aqueous sodium bicarbonate solution and saturated aqueous sodium chloride, dried and the solvent was distilled off in vacuo. The residue was purified with flush column chromatography (hexane:ethyl acetate=10:1) to obtain the compound in the title (5.76 g).

(Process j) Synthesis of 2-hydroxy-3-methoxybiphenyl (Intermediate 70)

The intermediate 69 (1.05 g) and 85% phosphoric acid solution (1 ml, Wako Pure Chem. Co.) were added to dioxane (10 ml) and refluxed. The reaction mixture was cooled and water was added thereto, then extracted with ethyl acetate. Organic layer was combined, washed with saturated aqueous sodium chloride solution and dried. The solvent was distilled off in vacuo. The residue was purified with flush column chromatography (hexane:ethyl acetate 9:1) to obtain the compound in the title (792 mg).

(Process c-1) Synthesis of 2-butoxy-3-methoxybiphenyl (Intermediate 71)

The compound in the title (957 mg) was obtained by reacting with the intermediate 70 (792 mg), 1-iodobutane (3.64 g) and potassium carbonate anhydride (2.73 g) according to the process described in the process c-1 in example 1.

(Process f) Synthesis of Methyl 4-(2-butoxy-3-methoxy-1,1'-biphenyl-5-yl)-4-oxo Butyrate (Intermediate 72)

The compound in the title (516 mg) was obtained by reacting with the intermediate 71 (940 mg), aluminum chloride (978 mg) and 3-carbomethoxypropionyl chloride (1.10 g) according to the process described in the process f in example 28.

(Process e) Synthesis of Methyl 4-(2-butoxy-3-methoxy-1,1'-biphenyl-5-yl)butyrate (Intermediate 73)

The compound in the title (303 mg) was obtained by reacting with the intermediate 72 (516 mg), conc. HCl (0.2 ml) and 10% palladium carbon (255 mg) according to the process described in the process e in example 28.

(Process a) Synthesis of 4-(2-butoxy-3-methoxy-1,1'-biphenyl-5-yl)butyric Acid (Compound 54)

The compound in the title (272 mg) was obtained by reacting with the intermediate 73 (303 mg) according to the process described in the process a in example 1.

Rf=0.52 (chloroform:methanol=10:1)

Example 55

4-(2-butoxy-1,1'-biphenyl-5-yl)butyramide (Compound 55)

(Process b-1) Synthesis of 4-(2-butoxy-1,1'-biphenyl-5-yl)butyramide (Compound 55)

The compound in the title (345 mg) was obtained by reacting with the compound 28 (400 mg), thionyl chloride (0.39 ml) and 25% aqueous ammonia (2.0 ml) according to the process described in the process b-1 in example 27.

Rf=0.58 (chloroform:methanol=10:1)

Example 56

4-(2-carbamoylmethyloxy-1,1'-biphenyl-5-yl)butyramide (Compound 56)

(Process b-1) Synthesis of 4-(2-carbamoylmethyloxy-1,1'-biphenyl-5-yl)butyramide (Compound 56)

The compound in the title (454 mg) was obtained by reacting with the compound 44 (630 mg), thionyl chloride (1.00 g) and 25% aqueous ammonia (20 ml) according to the process described in the process b-1in example 27.

Rf=0.42 (chloroform:methanol=10:1)

Example 57

4-[2-(3-carbamoylpropyloxy)-1,1'-biphenyl-5-yl]butyramide (Compound 57)

(Process b-1) Synthesis of 4-[2-(3-carbamoylpropyloxy)-1,1'-biphenyl-5-yl]butyramide (Compound 57)

The compound in the title (248 mg) was obtained by reacting with the compound 46 (450 mg), thionyl chloride (595 mg) and 25% aqueous ammonia (10 ml) according to the process described in the process b-1 in example 27.

Rf=0.37 (chloroform:methanol=10:1)

Example 58

4-[2-(4-chlorobutyloxy)-1,1'-biphenyl-5-yl]butyric Acid (Compound 58)

(Process c-1) Synthesis of Methyl 4-[2-(4-chlorobutyloxy)-1,1'-biphenyl-5-yl]butyrate (Intermediate 74)

The compound in the title (302 mg) was obtained by reacting with the intermediate 41 (270 mg), 1,4-dichlorobutane (1.14 g, Tokyo Chemical Ind. Co., Ltd.) and potassium carbonate anhydride (1.00 g) according to the process described in the process c-1 in example 1.

(Process a) Synthesis of 4-[2-(4-chlorobutyloxy)-1,1'-biphenyl-5-yl]butyric Acid (Compound 58)

The compound in the title (290 mg) was obtained by reacting with the intermediate 74 (302 mg) according to the process described in the process a in example 1.

Rf=0.43 (chloroform:methanol=20:1)

Example 59

4-[2-(3-chlorobutyloxy)-1,1'-biphenyl-5-yl]butyric Acid (Compound 59)
(Process c-1) Synthesis of Methyl 4-[2-(3-chlorobutyloxy)-1,1'-biphenyl-5-yl]butyrate (Intermediate 75)

The compound in the title (183 mg) was obtained by reacting with the intermediate 41 (270 mg), 1,3-dichlorobutane (1.12 g, Tokyo Chemical Ind. Co., Ltd.) and potassium carbonate anhydride (1.00 g) according to the process described in the process c-1 in example 1.
(Process a) Synthesis of 4-[2-(3-chlorobutyloxy)-1,1'-biphenyl-5-yl]butyric Acid (Compound 59)

The compound in the title (175 mg) was obtained by reacting with the intermediate 75 (183 mg) according to the process described in the process a in example 1.

Rf=0.42 (chloroform:methanol=20:1)

Example 60

4-[2-(4-bromobutyloxy)-1,1'-biphenyl-5-yl]butyric Acid (Compound 60)
(Process c-1) Synthesis of Methyl 4-[2-(4-bromobutyloxy)-1,1'-biphenyl-5-yl]butyrate (Intermediate 76)

The compound in the title (325 mg) was obtained by reacting with the intermediate 41 (270 mg), 1,4-dibromobutane (648 mg, Tokyo Chemical Ind. Co., Ltd.) and anhydrous potassium carbonate (414 mg) according to the process described in the process c-1 in example 1.
(Process a) Synthesis of 4-[2-(4-bromobutyloxy)-1,1'-biphenyl-5-yl]butyric Acid (Compound 60)

The compound in the title (292 mg) was obtained by reacting with the intermediate 76 (325 mg) according to the process described in the process a in example 1.

Rf=0.41 (chloroform:methanol=20:1)

Example 61

4-[2-(4,4,4-trifluorobutyloxy)-1,1'-biphenyl-5-yl]butyric Acid (Compound 61)
(Process c-1) Synthesis of Methyl 4-[2-(4,4,4-trifluorobutyloxy)-1,1'-biphenyl-5-yl]butyrate (Intermediate 77)

The compound in the title (703 mg) was obtained by reacting with the intermediate 41 (500 mg), 1-iodo-4,4,4-trifluorobutane (2.20 g, Oakwood Products, Inc.) and potassium carbonate anhydride (1.28 g) according to the process described in the process c-1 in example 1.
(Process a) Synthesis of 4-[2-(4,4,4-trifluorobutyloxy)-1,1'-biphenyl-5-yl]butyric Acid (Compound 61)

The compound in the title (611 mg) was obtained by reacting with the intermediate 77 (690 mg) according to the process described in the process a in example 1.

Rf=0.40 (chloroform:methanol=20:1)

Effect of the Invention

Pharmacological action of the compound of the present invention is explained hereinbelow.
1. Suppressive Effect on Mouse in vivo Anti-OVA-IgE Antibody Production
(1) A Method for Measurement BALB/c mice, female, 7 weeks old, 7 mice in a group, and 9–11 mice in control group, were used for tests.

Suppressive effect of the compound of the present invention on IgE antibody production was evaluated according to a method described in the reference, Levin and Vaz, International Archives of Allergy and Applied Immunology, 39: 156, 1970. Immunization was performed by intraperitoneally administering aluminium hydroxide gel (4 mg, PIERCE Inc.) adsorbed with egg albumin (OVA; Sigma Inc.) 10 μg in mice. Test compounds were suspended or dissolved in water containing 0.5% carboxymethyl cellulose, and administered orally to test animals, 100 mg/kg, immediately after immunization, once a day for 5 days. Water containing 0.5% carboxymethyl cellulose without addition of test compound was administered to the control group.

On day 14 after the immunization, blood was collected, and passive cutaneous anaphylaxis (PCA) reaction was performed according to the method described in the reference, Ovary et al. International Archives of Allergy and Applied Immunology, 48: 16, 1975, to determine the antibody production. Serum 0.1 ml, which was serially twofold diluted with physiological saline, was injected intracutaneously in the back of Wistar rats, male, 8 weeks old. After 24 hours, 0.5% Evans blue physiological saline solution, which contains OVA 2 mg, 1 ml was injected intravenously to determine the serum boundary concentration of pigment infiltration.

Compounds used as a control are as follows.

Control substance (1): 3-(2-methoxy-1,1'-biphenyl-5-yl) propionic acid (J. Am. Chem. Soc. 75: 2334, 1953);

Control substance (2): Methyl 3-(4'-allyloxy-2-benzyloxy-1,1'-biphenyl-5-yl)propionate (Chem. Pharm. Bull. 35: 1755, 1987);

Control substance (3): [2-(5,6,7,8-tetrahydro-5,5,8,8-tetramethyl-2-naphthalenyl)methyloxy-1,1'-biphenyl-5-yl]carboxylic acid (U.S. Pat. No. 5,391,817); and Control substance (4): 3-[3'-carboxy-2-(5,6,7,8-tetrahydro-5,5,8,8-tetramethyl-2-naphthalenyl) methyloxy-1,1'-biphenyl-6-yl]propionic acid.

In addition, compounds produced by the following methods are also used as control.

Control substance (5): N-ethyl-4-(2-butoxy-1,1'-biphenyl-5-yl)butyramide; and

Control substance (6): 4-(4-butoxy-1,1'-biphenyl-3-yl) butyric acid. Production of N-ethyl-4-(2-butoxy-1,1'-biphenyl-5-yl)butyramide [control (5)]: The compound (500 mg) was obtained by reacting with 4-(2-butoxy-1,1'-biphenyl-5-yl)butyric acid (compound 28)(1.00 g), thionyl chloride (0.50 ml) and 33% ethylamine aqueous solution (Tokyo Chemical Ind., Ltd.) 5 ml according to the method described in the process b-1 in example 27.

Mass (FAB+) 340 (MH+)

Production of 4-(4-butoxy-1,1'-biphenyl-3-yl)butyric acid [control (6)]:
(Process d) Synthesis of Methyl 4-(4-hydroxy-1,1'-biphenyl-3-yl)butyrate (Intermediate 78)

The compound (310 mg) was obtained by reacting with 4-(4-methoxy-1,1'-biphenyl-3-yl)butyric acid (350 mg), which was described in the reference, Fieser et al. J. Am. Chem. Soc. 58: 1783, 1936, pyridine (5 ml), concentrated hydrochloric acid (5 ml), methanol (5 ml) and thionyl chloride (300 ml) according to the method described in the process d in example 1.

Mass (FAB+) 271 (MH+)
(Process c-1) Synthesis of Methyl 4-(4-butoxy-1,1'-biphenyl-3-yl)butyrate (Intermediate 79)

The compound in the title (333 mg) was obtained by reacting the intermediate 78 (300 mg), iodo butane (404 mg) and anhydrous potassium carbonate (277 mg) according to the method described in the process c-1 in example 1.

Mass (FAB+) 327 (MH+)

(Process a) Synthesis of 4-(4-butoxy-1,1'-biphenyl-3-yl) butyric Acid [Control (6)]

The compound in the title (304 mg) was obtained by reacting with the intermediate 79 (320 mg) according to the method described in the process a in example 1.

Mass (FAB+) 313 (MH+)

Suppressive rate for IgE antibody production is determined by the following equation.

Suppressive rate for IgE antibody production (%)

$$= \left[1 - \frac{PCA \text{ titer of test compound administered group}}{PCA \text{ titer of control group}}\right] \times 100$$

(2) Test Results

Resuts are shown in the following table 2.

TABLE 2

| Test compound | Suppressive rate for IgE antibody production (%) |
|---|---|
| Compound(01) | 72.3 |
| Compound(03) | 50.9 |
| Compound(04) | 45.5 |
| Compound(07) | 62.0 |
| Compound(08) | 58.9 |
| Compound(12) | 50.8 |
| Compound(15) | 64.2 |
| Compound(22) | 48.1 |
| Compound(25) | 45.5 |
| Compound(28) | 44.5 |
| Compound(29) | 55.7 |
| Compound(31) | 49.8 |
| Compound(44) | 71.5 |
| Compound(45) | 57.0 |
| Compound(46) | 64.6 |
| Compound(47) | 65.7 |
| Compound(52) | 64.2 |
| Compound(55) | 55.7 |
| Control(1) | −14.4 |
| Control(2) | −11.6 |
| Control(3) | −2.8 |
| Control(4) | −8.4 |
| Control(5) | −2.5 |
| Control(6) | 7.3 |

As shown in table 2, the compounds of the present invention in oral administration have significant suppressive action for IgE production in BALB/c mice, which was sensitized by egg albumin. No suppressive action for IgE production was noted in the control compounds.

Consequently, novel biphenyl-5-alkanoic acid derivatives of the present invention are useful for IgE antibody production suppressor and drugs for treatment and/or prevention of allergic diseases involved in IgE antibody. Namely, the compound of the present invention is useful for treatment and prevention of bronchial asthma, allergic rhinitis, atopic dermatitis and allergic conjunctivitis.

2. Effect on Suppression of Mouse in vivo Foot-pad Reaction (1) Method of Measurement BALB/c mice, female, 7 weeks old, 5 mice in a group for test group and 12–14 mice for control group were used for tests.

Effect of the compounds of the present invention on suppression of mouse in vivo foot-pad reaction is evaluated by the following method.

Mice were immunized by administering intraperitoneally 4 mg of aluminium hydroxide gel, which was adsorbed with OVA 5 μg. Test compounds were suspended or dissolved in water containing 0.5% carboxymethyl cellulose, and were administered to test animals orally at 3–100 mg/kg, once a day, for 5 days, from immediately after immunization. For control groups, water containing 0.5% carboxymethyl cellulose without addition of the test compound was administered.

After 10 days of immunization, OVA 10 μg was injected into the hindlim pads of mice to induce immediate type allergic foot-pad reaction. Control groups were divided into tow groups. The one was injected OVA to induce allergic foot-pad reaction for positive control, and the other was injected physiological saline for negative control. After 30 minutes, foot-pad volume of hidlimb of mice was measured by using Plethysmometer (Unicom Co.) to determine increased rate for comparison before induction of foot-pad reaction.

Suppressive rate for foot-pad reaction is obtained by the following equation.

Suppressive rate for foot-pad reaction (%)

$$= \left[1 - \frac{C - B}{A - B}\right] \times 100$$

wherein

A: increased rate of foot-pad reaction in positive control group,

B: increased rate of foot-pad reaction in negative control group,

C: increased rate of foot-pad reaction in test group (test compound administered group).

(2) Results

Test compounds (compound Nos. 04, 07, 22, 25, 28, 44, 47 and 55) showed significant suppressive action against immediate type allergic foot-pad reaction in BALB/c mice, which were immunized by egg albumin, by oral administration of the compound at 3–100 mg/kg, as compared with the positive control.

Consequently, the novel biphenyl-5-alkanoic acid derivatives or salt thereof of the present invention are useful for treatment and/or prevention of immediate type allergic diseases caused by IgE antibody.

3. Effect on Cytokine Production From Antigen Sensitized Spleen Cells in Mice (1) Method of Measurement Spleen cells of BALB/c mice, female, which were previously immunized by injecting aluminium hydroxide gel adsorbed with OVA intraperitoneally twice in 10 days interval, were stimulated by immobilized anti-mouse CD-3 monoclonal antibody (Famigen Inc.). Amounts of production of interleukin (IL)-4 and IL-5 in the culture supernatant after 48 hours were assayed by using enzyme-linked immunosorbent assay (Endogen Inc.) The test compounds, 1–10 μg/ml, were added at the initial stage of culture. No test compound added group was set as positive control, and a group without stimulation of immobilized anti-mouse CD-3 monoclonal antibody was set as negative control.

Suppressive rate for cytokine (IL-4 and IL-5) production is calculated by the following equation.

Suppressive rate for cytokine production (%)

$$= \left[1 - \frac{C - B}{A - B}\right] \times 100$$

wherein

A: cytokine production of positive control group,

B: cytokine production of negative control group,

C: cytokine production of test group (test compound added group).

(2) Result

Test compounds (compound Nos. 01, 07, 11, 17, 18, 20, 22, 25, 27 and 28) showed suppressive action with 50% or more for IL-4 and IL-5 production as a result of anti-mouyse CD-3 antibody stimulation in OVA sensitized mouse spleen cells.

Human B cells differentiate to IgE producing cells in the presence of IL-4 (Romagnani, S. Immunol. Today, 11: 316, 1990) and anti-IL-4 antibody inhibits IgE production (Finkelman et al. Ann. Rev. Immunol. 8: 303, 1990). IL-4 has known to be an essential cytokine for IgE production. On the other hand, IL-5 is an essential cytokine for differentiation and activation of eosinophils (Sanderson et al. Proc. Natl. Acad. Sci. USA, 83: 437, 1986) and has an action for infiltration of eosinophils, which have important role in allergic inflammation, to inflammatory region (Durham et al. J. Immunol., 148: 2390, 1992).

Consequently, as the results, the above shown suppressive action for IgB production by the test compounds of the present invention might be possibly based on suppressive action for IL-4 production. Further, the compound of the present invention might have possibility to show suppressive action against allergic inflammation bated on suppressive action for IL-5 production.

TABLE 1

| Compound No. | 1H-NMR(CDCl3): δ(ppm), J(Hz) | MS m/z |
|---|---|---|
| Inter. 1 | 2.63(2H, t, J=7.4), 2.92(2H, t, J=7.4), 3.67(3H, s), 5.14(1H, J=1.7), 6.90(1H, d, J=7.7), 7.07–7.11(2H, m), 7.34–7.52 (5H, m). | 256 (M+) |
| Inter. 2 | 0.90(3H, t, J=7.4), 1.33–1.46 (2H, m), 1.63–1.73(2H, m), 2.64 (2H, t, J=7.4), 2.94(2H, t, J=7.4), 3.67(3H, s), 3.93(2H, t, J=6.3), 6.89(1H, d, J=8.2), 7.11 (1H, dd, J=8.2, 2.2), 7.16(1H, d, J=2.2), 7.27–7.42(3H, m), 7.51–7.55(2H, m). | 312 (M+) |
| 01 | 0.90(3H, t, J=7.4), 1.33–1.47 (2H, m), 1.63–1.73(2H, m), 2.68 (2H, t, J=7.4), 2.94(2H, t, J=7.4), 3.93(2H, t, J=6.3), 6.89 (1H, d, J=8.5), 7.12(1H, dd, J=8.5, 2.4), 7.17(1H, d, J=2.4), 7.26–7.42(3H, m), 7.50–7.55(2H, m). | 298 (M+) |
| Inter. 3 | 0.92(6H, d, J=6.9), 1.94–2.05 (1H, m), 2.63(2H, t, J=7.4), 2.94 (2H, t, J=7.4), 3.67(3H, s), 3.69(2H, d, J=6.3), 6.88(1H, d, J=8.5), 7.11(1H, dd, J=8.5, 2.4), 7.16(1H, d, J=2.4), 7.27–7.42(3H, m), 7.51–7.55(2H, m). | 312 (M+) |
| 02 | (DMSO-d6): 0.89(6H, d, J=6.9), 1.83–1.98(1H, m), 2.53(2H, t, J=7.4), 2.80(2H, t, J=7.4), 3.71 (2H, d, J=6.3), 6.96–6.99(1H, m), 7.13–7.18(2H, m) 7.27–7.42(3H, m), 7.47–7.52(2H, m), 12.09(1H, br). | 298 (M+) |
| Inter. 4 | 0.87(3H, t, J=7.1), 1.23–1.42 (4H, m), 1.64–1.75(2H, m), 2.63 (2H, t, J=7.4), 2.93(2H, t, J= 7.4), 3.67(3H, s), 3.92(2H, t, J=6.6), 6.89(1H, d, J=8.5), 7.11 (1H, dd, J=8.5, 2.4), 7.16(1H, d, J=2.4), 7.27–7.42(3H, m), 7.51–7.55(2H, m). | 326 (M+) |

TABLE 1-continued

| Compound No. | 1H-NMR(CDCl3): δ(ppm), J(Hz) | MS m/z |
|---|---|---|
| 03 | 0.88(3H, t, J=7.1), 1.23–1.42 (4H, m), 1.65–1.75(2H, m), 2.69 (2H, t, J=7.7), 2.94(2H, t, J=7.7), 3.92(2H, t, J=6.6), 6.90 (1H, d, J=8.5), 7.12(1H, dd, J=8.5, 2.4), 7.17(1H, d, J=2.4), 7.27–7.42(3H, m), 7.50–7.55(2H, m). | 312 (M+) |
| Inter. 5 | 1.49–1.82(8H, m), 2.63(2H, t, J=7.4), 2.93(2H, t, J=7.4), 3.67 (3H, s), 4.67–4.72(1H, m), 6.89 (1H, d, J=8.2), 7.10(1H, dd, J=8.2, 2.2), 7.16(1H, d, J=2.2), 7.25–7.40(3H, m), 7.49–7.53 (2H, m). | 324 (M+) |
| 04 | 1.52–1.80(8H, m), 2.69(2H, t, J=7.4), 2.94(2H, t, J=7.4), 4.67–4.73(1H, m), 6.90(1H, d J=8.2), 7.11(1H, dd, J=8.2, 2.2), 7.17(1H, d, J=2.2), 7.28–7.40 (3H, m), 7.50–7.53(2H, m). | 310 (M+) |
| Inter. 6 | 1.20–1.53(6H, m), 1.58–1.70(2H, m), 1.78–1.88(2H, m), 2.63 (2H, t, J=7.4), 2.93(2H, t, J=7.4), 3.68(3H, s), 4.09–4.18(1H, m), 6.91(1H, d, J=8.5), 7.09 (1H, dd, J=8.5, 2.5), 7.16(1H, d, J=2.5), 7.26–7.41(3H, m), 7.52–7.56(2H, m). | 338 (M+) |
| 05 | 1.20–1.54(6H, m), 1.58–1.70(2H, m), 1.78–1.88(2H, m), 2.69 (2H, t, J=7.4), 2.94(2H, t, J=7.4), 4.10–4.18(1H, m), 6.91(1H, d, J=8.5), 7.10(1H, dd, J=8.5, 2.5), 7.17(1H, d, J=2.5), 7.25–7.41(3H, m), 7.52–7.56(2H, m). | 324 (M+) |
| Inter. 7 | 1.19–1.33(2H, m), 1.49–1.60(4H, m), 1.69–1.79(2H, m), 2.22–2.32(1H, m), 2.64(2H, t, J=7.7), 2.93(2H, t, J=7.7), 3.67(3H, s), 3.81(2H, d, J=6.8), 6.89 (1H, d, J=8.5), 7.11(1H, dd, J=8.5, 2.5), 7.17(1H, d, J=2.5), 7.27–7.41(3H, m), 7.52–7.56(2H, m). | 338 (M+) |
| 06 | 1.18–1.34(2H, m), 1.48–1.58(4H, m), 1.68–1.80(2H, m), 2.22–2.32(1H, m), 2.68(2H, t, J=7.4), 2.95(2H, t, J=7.4), 3.80(2H, d, J=6.8), 6.89(1H, d, J=8.2), 7.12(1H, dd, J=8.2, 2.2), 7.18 (1H, d, J=2.2), 7.25–7.41(3H, m), 7.53–7.56(2H, m). | 324 (M+) |
| Inter. 8 | 0.90–1.30(5H, m), 1.60–1.81(6H, m), 2.63(2H, t, J=7.4), 2.93(2H, t, J=7.4), 3.67(3H, s), 3.72 (2H, d, J=6.0), 6.88(1H, d, J=8.2), 7.11(1H, dd, J=8.2, 2.2), 7.16(1H, d, J=2.2), 7.27–7.42 (3H, m), 7.50–7.55(2H, m). | 352 (M+) |
| 07 | (DMSO-d6): 0.90–1.26(5H, m), 1.55–1.75(6H, m), 2.53(2H, t, J=7.4), 2.80(2H, t, J=.74), 3.74 (2H, d, J=5.8), 6.95–7.00(1H, m), 7.12–7.17(2H, m), 7.27–7.42 (3H, m), 7.46–7.51(2H, m). | 338 (M+) |
| Inter. 9 | 0.95(3H, t, J=7.4), 1.45–1.58 (2H, m), 2.06(1H, d, J=3.6), 2.64 (2H, t, J=7.4), 2.94(2H, t, J=7.4), 3.68(3H, s), 3.72–3.83 (2H, m), 3.94–4.02(1H, m), 6.91 (1H, d, J=8.0), 7.12–7.17(2H, m), 7.29–7.44(3H, m), 7.46–7.51 (2H, m). | 328 (M+) |
| 08 | (DMSO-d6): 0.85(3H, t, J=7.4), 1.26–1.58(2H, m), 2.53(2H, t, J=7.4), 2.81(2H, t, J=7.4), 3.56– | 314 (M+) |

TABLE 1-continued

| Compound No. | 1H-NMR(CDCl3): δ(ppm), J(Hz) | MS m/z |
|---|---|---|
| | 3.67(1H, m), 3.77–3.90(2H, m), 4.69(1H, d, J=5.2), 6.98–7.02(1H, m), 7.13–7.17(2H, m), 7.27–7.41(3H, m), 7.51–7.56 (2H, m), 12.09(1H, s). | |
| Inter. 10 | 0.95(3H, t, J=7.4), 1.45–1.58 (2H, m), 2.06(1H, d, J=3.6), 2.64 (2H, t, J=7.4), 2.94(2H, t, J=7.4), 3.68(3H, s), 3.72–3.83 (2H, m), 3.94–4.02(1H, m), 6.91 (1H, d, J=8.0), 7.12–7.17(2H, m), 7.29–7.44(3H, m), 7.46–7.51 (2H, m). | 328 (M+) |
| 09 | (DMSO-d6): 0.85(3H, t, J=7.4), 1.26–1.58(2H, m), 2.53(2H, t, J=7.4), 2.81(2H, t, J=7.4), 3.56–3.67(1H, m), 3.77–3.90(2H, m), 4.69(1H, d, J=5.2), 6.98–7.02(1H, m), 7.13–7.17(2H, m), 7.27–7.41(3H, m), 7.51–7.56 (2H, m), 12.09(1H, s). | 314 (M+) |
| Inter. 11 | 0.95(3H, t, J=7.4), 1.45–1.58 (2H, m), 2.06(1H, d, J=3.6), 2.64 (2H, t, J=7.4), 2.94(2H, t, J=7.4), 3.68(3H, s), 3.72–3.83 (2H, m), 3.94–4.02(1H, m), 6.91 (1H, d, J=8.0), 7.12–7.17(2H, m), 7.29–7.44(3H, m), 7.46–7.51 (2H, m). | 328 (M+) |
| 10 | (DMSO-d6): 0.85(3H, t, J=7.4) 1.26–1.58(2H, m), 2.53(2H, t, J=7.4), 2.81(2H, t, J=7.4), 3.56–3.67(1H, m), 3.77–3.90(2H, m), 4.69(1H, d, J=5.2), 6.98–7.02(1H, m), 7.13–7.17(2H, m), 7.27–7.41(3H, m), 7.51–7.56 (2H, m), 12.09(1H, s). | 314 (M+) |
| Inter. 12 | 1.01(3H, t, J=7.4), 2.60(2H, q, J=7.4), 2.64(2H, t, J=7.4), 2.95 (2H, t, J=7.4), 3.68(3H, s) 4.47(2H, s), 6.76(1H, d, J=8.2), 7.12(1H, dd, J=8.2, 2.2), 7.19 (1H, d, J=2.2), 7.31–7.45(3H, m), 7.52–7.56(2H, m). | 326 (M+) |
| 11 | 1.01(3H, t, J=7.4), 2.60(2H, q, J=7.4), 2.69(2H, t, J=7.4),2.95 (2H, t, J=7.4), 4.47(2H, s) 6.76(1H, d, J=8.2), 7.14(1H, dd, J=8.2, 2.2), 7.20(1H, d, J=2.2), 7.32–7.45(3H, m), 7.52–7.56(2H, m). | 314 (M+) |
| Inter. 13 | 1.27(3H, t, J=7.1), 2.63(2H, t, J=7.4), 2.94(2H, t, J=7.4), 3.67 (3H, s), 4.23(2H, q, J=7.1), 4.56(2H, s), 6.80(1H, d, J=8.5), 7.10(1H, dd, J=8.6, 2.4), 7.19 (1H, d, J=2.4), 7.29–7.44(3H, m), 7.57–7.62(2H, m). | 342 (M+) |
| 12 | (DMSO-d6): 2.54(2H, t, J=7.4), 2.80(2H, t, J=7.4), 4.66(2H, s), 6.88(1H, d, J=8.2), 7.12–7.18 (2H, m), 7.27–7.43(3H, m), 7.53–7.58(2H, m). | 300 (M+) |
| Inter. 14 | 2.65(2H, t, J=7.7), 2.96(2H, t, J=7.7), 3.68(3H, s), 4.45(2H, s), 5.47(1H, br), 6.25(1H, br), 6.86(1H, d, J=8.2), 7.16–7.19 (2H, m), 7.33–7.50(3H, m). | 314 (MH+) |
| 13 | (DMSO-d6): 2.63(2H, t, J=7.7) 2.81(2H, t, J=7.7), 4.40(2H, s), 6.90(1H, d, J=9.3), 7.10(2H, br), 7.15–7.18(2H, m) 7.30–7.44(3H, m), 7.56–7.59(2H, m). | 300 (MH+) |
| Inter. 15 | 0.75(3H, t, J=7.4), 1.13–1.28 (2H, m), 1.39–1.48(2H, m), 2.68 (2H, t, J=7.4), 3.00(2H, t, J=7.4), 3.57(2H, t, J=6.3), 3.69 | 358 (MH+) |
| | (3H, s), 7.33–7.47(4H, m), 7.50–7.56(3H, m). | |
| 14 | 0.75(3H, t, J=7.4), 1.13–1.26 (2H, m), 1.39–1.49(2H, m), 2.74 (2H, t, J=7.4), 3.01(2H, t, J=7.4), 3.57(2H, t, J=6.3), 7.36–7.47(4H, m), 7.50–7.57(3H, m). | 344 (MH+) |
| Inter. 16 | 0.78(3H, t, J=7.4), 1.19–1.32 (2H, m), 1.42–1.52(2H, m), 1.58 (1H, br), 2.62(2H, t, J=7.4), 2.86(2H, t, J=7.4), 3.42(2H, t, J=6.3),3.68(3H, s), 3.92(1H, br), 6.55(1H, d, J=2.2), 6.59 (1H, d, J=2.2), 7.27–7.42(3H, m), 7.53–7.57(2H, m). | 327 (M+) |
| Inter. 17 | 0.82(3H, t, J=7.4), 1.23–1.37 (2H, m), 1.43–1.52(2H, m), 2.21 (3H, s), 2.66(2H, t, J=7.4), 2.92(2H, t, J=7.4), 3.41(2H, t, J=6.3), 3.68(3H, s), 6.89(1H, d, J=2.2), 7.30–7.44(3H, m), 7.50–7.54(2H, m), 7.94(1H, br) 8.23(1H, d, J=2.2). | 370 (MH+) |
| 15 | 0.82(3H, t, J=7.4), 1.21–1.36 (2H, m), 1.42–1.52(2H, m), 2.21 (3H, s), 2.70(2H, t, J=7.4), 2.96 (2H, t, J=7.4), 3.41(2H, t, J=6.3), 6.91(1H, d, J=2.2), 7.30–7.44(3H, m), 7.50–7.54(2H, m), 7.98(1H, br), 8.23(1H, d, J=2.2). | 356 (MH+) |
| Inter. 18 | 0.79(3H, t, J=7.4), 1.17–1.30 (2H, m), 1.42–1.52(2H, m), 2.65 (2H, t, J=7.4) 2.95(2H, t, J=7.4), 3.09(3H, s), 3.40(2H, t, J=6.6), 3.69(3H, s), 6.92(1H, d, J=2.2), 7.04(1H, br), 7.32–7.46(4H, m), 7.49–7.4(2H, m). | 405 (M+) |
| 16 | 0.78(3H, t, J=7.4), 1.16–1.30 (2H, m), 1.42–1.52(2H, m), 2.70 (2H, t, J=7.7), 2.96(2H, t, J=7.7), 3.08(3H, s), 3.41(2H, t, J=6.6), 6.94(1H, d, J=2.2), 7.06 (1H, br), 7.32–7.46(4H, m), 7.50–7.54(2H, m). | 391 (M+) |
| Inter. 19 | 0.68–0.85(2H, m), 0.98–1.22 3H, m), 1.38–1.67(6H, m), 2.67 (2H, t, J=7.7), 2.99(2H, t, J=7.4), 3.36(2H, d, J=6.0), 3.69(3H, s), 7.36–7.55(7H, m). | 397 (M+) |
| Inter. 20 | 0.77–1.20(5H, m), 1.40–1.70(7H, m), 2.62(2H, t, J=7.7), 2.85 (2H, t, J=7.4), 3.21(2H, d, J=6.0), 3.68(3H, s), 3.91(1H, br), 6.55(1H, d, J=1.9), 6.59(1H, d, J=1.9), 7.27–7.41(3H, m), 7.52–7.56(2H, m). | 367 (M+) |
| Inter. 21 | 0.86–1.33(5H, m), 1.40–1.75(6H, m), 2.20(3H, s), 2.65(2H, t, J=7.7), 2.95(2H, t, J=7.7), 3.19 (2H, d, J=5.8), 3.68(3H, s), 6.89(1H, d, J=2.2), 7.31–7.43 (3H, m), 7.50–7.54(2H, m), 7.96 (1H, br), 8.22(1H, d, J=2.2). | 410 (MH+) |
| 17 | (DMSO-d6): 0.68–1.16(6H, m), 1.35–1.62(6H, m), 2.08(3H, s), 2.53(2H, t, J=7.7), 2.80(2H, t, J=7.4), 3.17(2H, d, J=5.8), 6.96(1H, br), 7.32–7.51(5H, m), 7.64(1H, br), 9.13(1H, br). | 396 (MH+) |
| Inter. 22 | 0.77–1.31(6H, m), 1.40–1.75(6H, m), 2.65(2H, t, J=7.4), 2.95 (2H, t, J=7.4), 3.00(3H, s), 3.19 (2H, d, J=6.0), 3.69(3H, s), 6.93(1H, d, J=2.2), 7.01(1H, br), 7.31–7.53(6H, m). | 445 (M+) |

TABLE 1-continued

| Compound No. | 1H-NMR(CDCl3): δ(ppm), J(Hz) | MS m/z |
|---|---|---|
| 18 | 0.75–1.30(5H, m), 1.40–1.72(6H, m), 2.70(2H, t, J=7.7), 2.96 (2H, t, J=7.4), 3.08(3H, s), 3.19 (2H, d, J=5.8), 6.93(1H, d, J=1.9), 7.03(1H, br), 7.32–7.53 (6H, m). | 432 (MH+) |
| Inter 23 | 0.77–1.26(5H, m), 1.40–1.72(6H, m), 2.24(3H, s), 2.66(2H, t, J=7.4), 2.96(2H, t, J=7.4), 3.20 (2H, d, J=6.0), 3.68(3H, s), 4.73(2H, s), 6.94(1H, d, J=2.2), 7.32–7.44(3H, m), 7.49–7.54 (2H, m), 8.26(1H, d, J=2.2), 8.65(1H, br). | 468 (MH+) |
| 19 | (DMSO–d6): 0.75–1.21(5H, m), 1.40–1.66(6H, m), 2.54(2H, t, J=7.7), 2.82(2H, t, J=7.4), 3.17 (2H, d, J=5.8), 4.01(2H, s), 6.94(1H, d, J=2.2), 7.35–7.54 (5H, m), 8.21(1H, d, J=1.9), 9.34 (1H, s). | 412 (MH+) |
| Inter. 24 | 0.77–1.24(5H, m), 1.36–1.72(6H, m), 2.65(2H, t, J=7.7), 2.93 (2H, t, J=7.4), 3.06(6H, s), 3.19 (2H, d, J=6.3), 3.67(3H, s), 6.79(1H, d, J=2.5), 7.29(1H, br), 7.31–7.43(3H, m), 7.49–7.53 (2H, m), 8.08(1H, d, J=2.2). | 439 (MH+) |
| 20 | 0.77–1.24(5H, m), 1.36–1.70(6H, m), 2.70(2H, t, J=7.7), 2.94 (2H, t, J=7.4), 3.07(6H, s), 3.19 (2H, d, J=6.0), 6.81(1H, d, J=2.2), 7.29(1H, br), 7.31–7.43 (3H, m), 7.49–7.53(2H, m), 8.06 (1H, d, J=2.2). | 425 (MH+) |
| Inter. 25 | 0.79–1.27(5H, m), 1.44–1.72(6H, m), 2.64(2H, t, J=7.4), 2.92 (6H, s), 2.94(2H, t, J=7.4), 3.20 (2H, d, J=5.8), 3.69(3H, s), 6.87(1H, d, J=2.2), 6.98(1H, br, J=2.2), 7.28(1H, d, J=2.2), 7.32–7.44(3H, m), 7.48–7.54(2H, m). | 474 (M+) |
| 21 | 0.79–1.28(1H, m), 1.42–1.72(6H, m), 2.69(2H, t, J=7.4), 2.91 (6H, s), 2.94(2H, t, J=7.4), 3.21 (2H, d, J=6.0), 6.88(1H, d, J=2.2), 6.99(1H, br), 7.30(1H, d, J=2.2), 7.32–7.44(3H, m), 7.48–7.53(2H, m). | 461 (MH+) |
| Inter. 26 | 0.78–1.28(5H, m), 1.40–1.72(6H, m), 2.65(2H, t, J=7.7), 2.94 4(2H, t, J=7.7), 3.20(2H, d, J=6.0), 3.68(3H, s), 4.75(2H, br), 6.86(1H, d, J=2.2), 7.05(1H, br), 7.30–7.43(3H, m), 7.48–7.53(2H, m), 7.80(1H, d, J=2.2). | 411 (MH+) |
| 22 | (DMSO–d6): 0.50–0.70(2H, m), 0.90–1.18(3H, m), 1.42–1.65 (6H, m), 2.51(2H, t, J=7.7), 2.77 (2H, t, J=7.7), 3.12(2H, d, J=6.3), 6.28(2H, br), 6.74(1H, d, J=2.2), 7.30–7.50(6H, m), 7.78 (1H, br), 7.92(1H, d, J=2.2). | 397 (MH+) |
| Inter. 27 | 1.06–1.38(5H, m), 1.69–1.97 (6H, m), 3.88–3.90(5H, m), 7.39 (1H, d, J=1.6), 7.85(1H, d, J=1.6), 9.82(1H, s). | 375 (MH+) |
| Inter. 28 | 0.71–0.90(2H, m), 1.02–1.20(3H, m), 1.43–1.65(6H, m), 3.58 (2H, d, J=6.0), 3.96(3H, s), 7.34–7.55(7H, m), 9.93(1H, s). | 325 (MH+) |
| Inter. 29 | 0.68–0.86(2H, m), 1.02–1.20(3H, m), 1.34(3H, t, J=7.1), 1.43–1.64(6H, m), 3.49(2H, d, J=6.3), 3.92(3H, s), 4.26(2H, q, J=7.1), 6.38(1H, d, J=15.9), 7.06 (1H, d, J=1.9), 7.13(1H, d, J=1.9), 7.30–7.43(3H, m), 7.49–7.53(2H, m), 7.66(1H, d, J=15.9). | 394 (M+) |
| Inter. 30 | 0.68–0.80(2H, m), 1.02–1.18(3H, m), 1.24(3H, t, J=7.1), 1.44–1.63(6H, m), 2.64(2H, t, J=7.4), 2.94(2H, t, J=7.4), 3.41(2H, d, J=6.3), 3.87(3H, s), 4.14 (2H, q, J=7.1), 6.74–6.78(2H, m), 7.26–7.41(3H, m), 7.49–7.53 (2H, m). | 396 (M+) |
| 23 | 0.68–0.80(2H, m), 1.02–1.17(3H, m), 1.42–1.63(6H, m), 2.71 (2H, t, J=7.4), 2.96(2H, t, J=7.4), 3.41(2H, d, J=6.3), 3.87(3H, s), 6.75–6.79(2H, m), 7.28–7.41(3H, m), 7.49–7.53(2H, m). | 368 (M+) |
| Inter. 31 | 0.80–0.94(2H, m), 1.02–1.26 (3H, m) 1.43–1.70(6H, m), 2.64 (2H, t, J=7.4), 2.91(2H, t, J=7.4), 3.23(2H, d, J=6.0), 3.68(3H, s), 5.85(1H, s), 6.70(1H, d, J=2.2), 6.80(1H, d, J=2.2), 7.31–7.43(3H, m), 7.52–7.56(2H, m). | 368 (M+) |
| 24 | 0.80–0.94(2H, m), 1.02–1.28(3H, m), 1.47–1.70(6H, m), 2.68 (2H, t, J=7.4), 2.91(2H, t, J=7.4), 3.24(2H, d, J=6.0), 6.71(1H, d, J=2.2), 6.81(1H, d, J=2.2), 7.31–7.43(3H, m), 7.52–7.56 (2H, m). | 354 (M+) |
| Inter. 32 | 1.06–1.40(5H, m), 1.70–1.94(6H, m), 3.90(2H, d, J=6.0), 6.97 (1H, d, J=8.5), 7.79(1H, dd, J=8.5, 2.2), 8.07(1H, d, J=2.2), 9.83(1H, s). | 296 (M+) |
| Inter. 33 | 0.90–1.31(5H, m), 1.59–1.83(6H, m), 3.86(2H, d, J=6.0), 3.71 (2H, d, J=6.0), 5.12(2H, s), 7.00–7.06(3H, m), 7.26–7.51(7H, m), 7.79–7.84(2H, m), 9.91(1H, s). | 400 (M+) |
| Inter. 34 | 0.95–1.32(5H, m), 1.60–1.82 (6H, m), 3.78–3.80(5H, m), 5.11 (2H, s), 6.33(1H, d, J=15.9), 6.92 (1H, d, J=8.5), 7.00–7.05(2H, m), 7.18–7.50(9H, m), 7.68 (1H, d, J=15.9). | 456 (M+) |
| Inter. 35 | 0.90–1.34(5H, m), 1.54–1.83 (6H, m), 2.63(2H, t, J=7.4), 2.92 (2H, t, J=7.4), 3.68(3H, s), 3.71 (2H, d, J=6.0), 4.89(1H, br), 6.84–6.90(3H, m), 7.06–7.15 (2H, m), 7.41–7.46(2H, m). | 368 (M+) |
| 25 | 0.86–1.30(5H, m), 1.56–1.80(6H, m), 2.68 (2H, t, J=7.4), 2.93 (2H, t, J=7.4), 3.71(2H, d, J=6.0), 6.83–6.89(3H, m), 7.07–7.14(2H, m), 7.39–7.46(2H, m). | 354 (M+) |
| Inter. 36 | 0.96–1.32(5H, m), 1.65–1.83(6H, m), 3.85–3.87(5H, m), 6.94–6.98(2H, m), 7.04(1H, d, J=8.5), 7.47–7.51(2H, m), 7.79–7.84 (2H, m), 9.92(1H, s). | 324 (M+) |
| Inter. 37 | 0.95–1.30(5H, m), 1.65–1.81(6H, m), 3.79–3.86(8H, m), 6.34 (1H, d, J=15.9), 6.92–6.97(3H, m), 7.41–7.51(4H, m), 7.68(1H, d, J=15.9). | 380 (M+) |
| Inter. 38 | 0.92–1.30(5H, m), 1.60–1.80(6H, m), 2.63(2H, t, J=7.4), 2.92 (2H, t, J=7.4), 3.67(3H, s), 3.72 (2H, d, J=6.0), 3.85(3H, s), 6.86(1H, d, J=8.2), 6.90–6.96 (2H, m), 7.08(1H, dd, J=8.2, 2.2), 7.14(1H, d, J=2.2), 7.45–7.50(2H, m). | 382 (M+) |

TABLE 1-continued

| Compound No. | 1H-NMR(CDCl3): δ(ppm), J(Hz) | MS m/z |
|---|---|---|
| 26 | 0.92–1.30(5H, m), 1.60–1.80(6H, m), 2.68(2H, t, J=7.4), 2.93 (2H, t, J=7.4), 3.72(2H, d, J=6.0), 3.85(3H, s), 6.87(1H, d, J=8.2), 6.90–6.96(2H, m), 7.09 (1H, dd, J=8.2, 2.2), 7.15(1H, d, J=2.2), 7.45–7.50(2H, m). | 368 (M+) |
| 27 | 0.90–1.32(5H, m), 1.57–1.80(6H, m), 2.53(2H, t, J=7.4), 2.96 (2H, t, J=7.4), 3.72(2H, d, J=5.8), 6.88(1H, d, J=8.2), 7.13 (1H, dd, J=8.2, 2.2), 7.17(1H, d, J=2.2), 7.25–7.42(3H, m), 7.50–7.55(2H, m). | 338 (MH+) |
| Inter. 39 | 2.76(2H, t, J=6.6), 3.60(2H, t, J=6.6), 3.70(3H, s), 3.88(3H, s), 7.02(1H, d, J=8.5), 7.33–7.45(3H, m), 7.50–7.53(2H, m), 7.97(1H, d, J=2.2), 8.00(1H, dd, J=8.5, 2.2). | 298 (M+) |
| Inter. 40 | 1.92–2.02(2H, m), 2.39(2H, t, J=7.4), 2.66(2H, t, J=7.4), 3.79 (3H, s), 5.10(1H, s), 6.89–6.92 (1H, m), 7.11–7.14(2H, m) 7.29–7.43(3H, m), 7.51–7.54 (2H, m). | 284 (M+) |
| Inter. 41 | 1.90–2.00(2H, m), 2.35(2H, t, J=7.4), 2.62(2H, t, J=7.4), 3.66 (3H, s), 5.10(1H, s), 6.91(1H, d, J=7.7), 7.05–7.09(2H, m), 7.37–7.52(5H, m). | 270 (M+) |
| Inter. 42 | 0.90(3H, t, J=7.4), 1.34–1.46 (2H, m), 1.64–1.73(2H, m), 1.91–2.01(2H, m), 2.35(2H, t, J=7.4), 2.63(2H, t, J=7.4), 3.66(3H, s), 3.93(2H, t, J=6.3), 6.89 (1H, d, J=8.2), 7.09(1H, dd, J=2.5, 8.2), 7.14(1H, d, J=2.5), 7.27–7.42(3H, m), 7.52–7.56 (2H, m). | 326 (M+) |
| 28 | 0.90(3H, t, J=7.4), 1.33–1.47 (2H, m), 1.62–1.72(2H, m), 1.92–2.02(2H, m), 2.39(2H, t, J=7.4), 2.66(2H, t, J=7.4), 3.93(2H, t, J=6.3), 6.90(1H, d, J=8.5), 7.10(1H, dd, J=2.5, 8.5). 7.14 (1H, d, J=2.5), 7.30–7.41 (3H, m), 7.53–7.56(2H, m). | 312 (M+) |
| Inter. 43 | 0.93(6H, d, J=6.3), 1.91–2.04 (3H, m), 2.35(2H, t, J=7.4), 2.63 (2H, t, J=7.4), 3.66(3H, s), 3.69(2H, d, J=6.3), 6.88(1H, d, J=8.2), 7.09(1H, dd, J=8.2, 2.2), 7.14(1H, d, J=2.2), 7.27–7.41(3H, m), 7.52–7.56(2H, m). | 326 (M+) |
| 29 | 0.93(6H, d, J=6.3), 1.92–2.04 (3H, m), 2.39(2H, t, J=7.4), 2.66 (2H, t, J=7.4), 3.69(2H, d, J=6.3), 6.88(1H, d, J=8.2), 7.09 (1H, dd, J=8.2, 2.2), 7.15(1H, d, J=2.2), 7.27–7.41(3H, m), 7.53–7.56(2H, m). | 312 (M+) |
| Inter. 44 | 0.86(3H, t, J=7.4), 1.18(3H, d, J=6.0), 1.44–1.71(2H, m), 1.91–2.01(2H, m), 2.35(2H, t, J=7.4), 2.63(2H, t, J=7.4), 3.66 (3H, s), 4.16–4.22(1H, m), 6.89 (1H, d, J=8.2), 7.07(1H, dd, J=8.2, 2.2), 7.13(1H, d, J=2.2), 7.25–7.41(3H, m), 7.52–7.56 (2H, m). | 326 (M+) |
| 30 | 0.86(3H, t, J=7.4), 1.17(3H, d, J=6.0), 1.44–1.71(2H, m), 1.91–2.01(2H, m), 2.38(2H, t, J=7.4), 2.64(2H, t, J=7.4), 4.12–4.24(1H, m), 6.89(1H, d, J=8.5), | 311 (M—H—) |
| | 7.07(1H, dd, J=8.5, 2.2), 7.13 (1H, d, J=2.2), 7.25–7.40 (3H, m), 7.52–7.55(2H, m). | |
| Inter. 45 | 0.88(3H, t, J=7.1), 1.26–1.40 (4H, m), 1.65–1.75(2H, m), 1.91–2.01(2H, m), 2.35(2H, t, J=7.4), 2.63(2H, t, J=7.4), 3.66 (3H, s), 3.92(2H, t, J=6.6), 6.89, (1H, d, J=8.2), 7.09(1H, dd, J=8.2, 2.2), 7.14(1H, d, J=2.2), 7.27–7.41(3H, m), 7.52–7.56 (2H, m). | 340 (M+) |
| 31 | 0.88(3H, t, J=7.1), 1.26–1.38 (4H, m), 1.65–1.75(2H, m), 1.91–2.01(2H, m), 2.39(2H, t, J=7.4), 2.65(2H, t, J=7.4), 3.92(2H, t, J=6.6), 6.89(1H, d, J=8.5), 7.09(1H, dd, J=8.5, 2.2), 7.14 (1H, d, J=2.2), 7.27–7.41 (3H, m), 7.51–7.55(2H, m). | 326 (M+) |
| Inter. 46 | 0.85(3H, t, J=7.4), 1.17(3H, d, J=6.3), 1.25–1.69(4H, m), 1.91–2.01(2H, m), 2.35(2H, t, J=7.4), 2.63(2H, t, J=7.4), 3.66 (3H, s), 4.19–4.30(2H, m), 6.89 (1H, d, J=8.2), 7.07(1H, dd, J=2.2, 8.2), 7.13(1H, d, J=2.2), 7.25–7.40(3H, m), 7.52–7.55 (2H, m). | 340 (M+) |
| 32 | 0.86(3H, t, J=7.4), 1.17(3H, d, J=6.3), 1.25–1.69(4H, m), 1.92–2.02(2H, m), 2.40(2H, t, J=7.4), 2.65(2H, t, J=7.4), 4.19–4.30(2H, m), 6.89(1H, d, J=8.2), 7.08(1H, dd, J=2.2, 8.2), 7.13 (1H, d, J=2.2), 7.26–7.40 (3H, m), 7.51–7.54(2H, m). | 326 (M+) |
| Inter. 47 | 0.84–0.93(6H, m), 1.09–1.82 (3H, m), 1.91–2.01(2H, m), 2.35 (2H, t, J=7.4), 2.63(2H, t, J=7.4), 3.66(3H, s), 3.70–3.79(2H, m), 6.88(1H, d, J=8.2), 7.09 (1H, dd, J=8.2, 2.2), 7.14(1H, d, J=2.2), 7.25–7.41(3H, m), 7.51–7.55(3H, m). | 340 (M+) |
| 33 | 0.84–0.93(6H, m), 1.11–1.82 (3H, m), 1.91–2.01(2H, m), 2.36 (2H, t, J=7.4), 2.64(2H, t, J=7.4), 3.66–3.81(2H, m), 6.88(1H, d, J=8.2), 7.08(1H, dd, J=8.2, 2.2), 7.14(1H, d, J=2.2), 7.26–7.40(3H, m), 7.51–7.55(3H, m). | 326 (M+) |
| Inter. 48 | 0.87(6H, d, J=6.6), 1.58(2H, q, J=7.4), 1.65–1.79(1H, m), 1.91–2.01(2H, m), 2.35(2H, t, J=7.4), 2.63(2H, t, J=7.4), 3.66 (3H, s), 3.95(2H, t, J=6.6), 6.90 90(1H, d, J=8.2), 7.09(1H, dd, J=2.2, 8.2), 7.14(1H, d, J=2.2), 7.27–7.41(3H, m), 7.51–7.55 (2H, m). | 340 (M+) |
| 34 | 0.87(6H, d, J=6.6), 1.59(2H, q, J=6.6), 1.65–1.78(1H, m), 1.92–2.02(2H, m), 2.39 (2H, t, J=7.4), 2.65(2H, t, J=7.4), 3.95 (2H, t, J=6.6), 6.90(1H, d, J=8.2), 7.09(1H, dd, J=2.2, 8.2), 7.14(1H, d, J=2.2), 7.27–7.41 (3H, m), 7.51–7.65(2H, m). | 326 (M+) |
| Inter. 49 | 1.48–1.84(8H, m), 1.91–2.01(2H, m), 2.35(2H, t, J=7.4), 2.63 (2H, t, J=7.4), 3.66(3H, s), 4.67–4.72(1H, m), 6.89(1H, d, J=8.2), 7.07(1H, dd, J=8.2, 2.2), 7.13(1H, d, J=2.2), 7.25–7.40 | 338 (M+) |

TABLE 1-continued

| Compound No. | 1H-NMR(CDCl3): δ(ppm), J(Hz) | MS m/z |
|---|---|---|
| | (3H, m), 7.60–7.54(2H, m). | |
| 35 | 1.48–1.84(8H, m), 1.92–2.02(2H, m), 2.39(2H, t, J=7.4), 2.65 (2H, t, J=7.4), 4.67–4.72(1H, m), 6.89(1H, d, J=8.2), 7.08(1H, dd, J=8.2, 2.2), 7.14(1H, d, J=2.2), 7.27–7.40(3H, m),7.50–7.54(2H, m). | 324 (M+) |
| Inter. 50 | 1.20–1.88(10H, m), 1.90–2.01 (2H, m), 2.34(2H, t, J=7.4), 2.62 (2H, t, J=7.4), 3.65(3H, s), 4.08–4.16(1H, m), 6.90(1H, d, J=8.5), 7.06(1H, dd, J=8.5, 2.2), 7.14(1H, d, J=2.2), 7.25–7.40 (3H, m), 7.50–7.57(2H, m). | 352 (M+) |
| 36 | 1.20–1.86(10H, m), 1.90–2.02 (2H, m), 2.39(2H, t, J=7.4), 2.65 (2H, t, J=7.4), 4.08–4.16(1H, m), 6.91(1H, d, J=8.5), 7.07 (1H, dd, J=8.5, 2.2), 7.14(1H, d, J=2.2), 7.25–7.41(3H, m), 7.54–7.57(2H, m). | 338 (M+) |
| Inter. 51 | 1.21–1.34(2H, m), 1.48–1.60 (4H, m), 1.69–1.79(2H, m), 1.91–2.01(2H, m), 2.22–2.32(1H, m), 2.35(2H, t, J=7.4), 2.63(2H, t, J=7.4), 3.66(3H, s), 3.81 (2H, d, J=6.6), 6.89(1H, d, J = 8.2), 7.09(1H, dd, J=8.2, 2.2), 7.14(1H, d, J=2.2), 7.27–7.41 (3H, m), 7.53–7.57(2H, m). | 352 (M+) |
| 37 | 1.23–1.33(2H, m), 1.49–1.60 (4H, m), 1.69–1.79(2H, m), 1.91–2.01(2H, m), 2.22–2.32(1H, m), 2.39(2H, t, J=7.4), 2.65(2H, t, J=7.4), 3.80(2H, d, J=6.6), 6.88(1H, d, J=8.2), 7.09(1H, dd, J=8.2, 2.2), 7.14(1H, d, J=2.2), 7.26–7.41(3H, m), 7.52–7.56(2H, m). | 338 (M+) |
| Inter. 52 | 0.93–1.28(5H, m), 1.64–1.77 (6H, m), 1.90–2.00(2H, m), 2.35 (2H, t, J=7.4), 2.63(2H, t, J=7.4), 3.66(3H, s), 3.72(2H, d, J=6.0), 6.88(1H, d, J=8.2), 7.09 (1H, dd, J=8.2, 2.2), 7.14(1H, d, J=2.2), 7.26–7.42(3H, m), 7.52–7.56(2H, m). | 366 (M+) |
| 38 | 0.96–1.26(5H, m), 1.68–1.77 (6H, m), 1.92–2.02(2H, m), 2.39 (2H, t, J=7.4), 2.66(2H, t, J=7.4), 3.72(2H, d, J=6.0), 6.88 (1H, d, J=8.2), 7.09(1H, dd, J=8.2, 2.2), 7.14(1H, d, J=2.2), 7.28–7.41(3H, m), 7.53–7.55 (2H, m). | 352 (M+) |
| Inter. 53 | 1.66–1.81(4H, m), 0.86(3H, t, J=7.4), 1.91–2.01(2H, m), 2.03 3(3H, s), 2.35(2H, t, J=7.4), 2.64 (2H, t, J=7.4), 3.66(3H, s), 3.95(2H, t, J=5.8), 4.03(2H, t, J=6.3), 6.89(1H, d, J=8.2), 7.09(1H, dd, J=8.2, 2.2), 7.14 (1H, d, J=2.2), 7.26–7.41(3H, m), 7.51–7.54(2H, m). | 384 (M+) |
| 39 | 1.58–1.67(2H, m), 1.74–1.83 2H, m), 1.91–2.01(2H, m), 2.39 (2H, t, J=7.4), 2.66(2H, t, J=7.4), 3.58(2H, t, J=6.3), 3.97 (2H, t, J=6.3), 6.90(1H, d, J=8.2), 7.10(1H, dd, J=8.2, 2.2), 7.14(1H, d, J=2.2), 7.26–7.42 (3H, m), 7.50–7.53(2H, m). | 328 (M+) |
| Inter. 54 | 1.20(3H, d, J=6.3), 1.90–2.00 (7H, m), 2.35(2H, t, J=7.4), 2.63 (2H, t, J=7.4), 3.66(3H, s), | 384 (M+) |

TABLE 1-continued

| Compound No. | 1H-NMR(CDCl3): δ(ppm), J(Hz) | MS m/z |
|---|---|---|
| | 3.96(2H, t, J=6.3), 4.98–5.09 (1H, m), 6.88(1H, d, J=8.2), 7.09(1H, dd, J=8.2, 2.2), 7.14 (1H, d, J=2.2), 7.28–7.53(5H, m). | |
| 40 | 1.15(3H, d, J=6.3), 1.83(2H, q, J=6.3), 1.91–2.01(2H, m), 2.39 (2H, t, J=7.4), 2.66(2H, t, J= 7.4), 3.84–3.97(2H, m), 3.99–4.17(2H, m), 6.92(1H, d, J=8.2), 7.10–7.13(2H, m), 7.28–7.50 (5H, m). | 328 (M+) |
| Inter. 55 | 0.94(3H, t, J=7.4), 1.44–1.54 (1H, m), 1.91–2.01(2H, m), 2.13 (1H, br), 2.34(2H, t, J=7.4), 2.63(2H, t, J=7.4), 3.65(3H, s), 3.72–3.78(2H, m), 3.94–4.02 (1H, m), 6.90(1H, d, J=8.2), 7.10(1H, dd, J=8.2, 2.2), 7.14 (1H, d, J=2.2), 7.28–7.42(3H, m), 7.47–7.51(2H, m). | 342 (M+) |
| 41 | 0.95(3H, t, J=7.4), 1.45–1.55 (2H, m), 1.91–2.01(2H, m), 2.09 (1H, br), 2.38(2H, t, J=7.4), 2.66(2H, t, J=7.4), 3.73–3.80 (2H, m), 3.94–4.02(1H, m), 6.91 (1H, d, J=8.2), 7.11(1H, dd, J=8.2, 2.2), 7.14(1H, d, J=2.2), 7.29–7.43(3H, m), 7.48–7.51 (2H, m). | 328 (M+) |
| Inter. 56 | 0.94(3H, t, J=7.4), 1.44–1.54 (1H, m), 1.91–2.01(2H, m), 2.13 (1H, br), 2.34(2H, t, J=7.4), 2.63(2H, t, J=7.4), 3.65(3H, s), 3.72–3.78(2H, m), 3.94–4.02 (1H, m), 6.90(1H, d, J=8.2), 7.10(1H, dd, J=8.2, 2.2), 7.14 (1H, d, J=2.2), 7.28–7.42(3H, m), 7.47–7.51(2H, m). | 342 (M+) |
| 42 | 0.95(3H, t, J=7.4), 1.45–1.55 (2H, m), 1.91–2.01(2H, m), 2.09 (1H, br), 2.38(2H, t, J=7.4), 2.66(2H, t, J=7.4), 3.73–3.80 (2H, m), 3.94–4.02(1H, m), 6.91 (1H, d, J=8.2), 7.11(1H, dd, J=8.2, 2.2), 7.14(1H, d, J=2.2), 7.29–7.43(3H, m), 7.48–7.51 (2H, m). | 328 (M+) |
| Inter. 57 | 0.94(3H, t, J=7.4), 1.44–1.54 (2H, m), 1.91–2.01(2H, m), 2.13 (1H, br), 2.34(2H, t, J=7.4), 2.63(2H, t, J=7.4), 3.65(3H, s), 3.72–3.78(2H, m), 3.94–4.02 (1H, m), 6.90(1H, d, J=8.2), 7.10(1H, dd, J=8.2, 2.2), 7.14 (1H, d, J=2.2), 7.28–7.42(3H, m), 7.47–7.51(2H, m). | 342 (M+) |
| 43 | 0.95(3H, t, J=7.4), 1.45–1.55 (2H, m), 1.91–2.01(2H, m), 2.09 (1H, br), 2.38(2H, t, J=7.4), 2.66(2H, t, J=7.4), 3.73–3.80 (2H, m), 3.94–4.02(1H, m), 6.91 (1H, d, J=8.2), 7.11(1H, dd, J=8.2, 2.2), 7.14(1H, d, J=2.2, 7.29–7.43(3H, m), 7.48–7.51 (2H, m). | 328 (M+) |
| Inter. 58 | 1.91–2.01(2H, m), 2.35(2H, t, J=7.4), 2.64(2H, t, J=7.4), 3.66 (3H, s), 3.77(3H, s), 4.57(2H, s), 6.80(1H, d, J=8.2), 7.09 (1H, dd, J=8.2, 2.2), 7.16(1H, d, J=2.2), 7.29–7.44(3H, m), 7.57–7.61(2H, m). | 342 (M+) |
| 44 | (CD3OD): 1.86–1.96(2H, m), 2.31 (2H, t, J=7.4), 2.64(2H, t, J= 7.4), 4.58(2H, s), 6.89(1H, d, J=8.2), 7.10–7.14(2H, m), | 314 (M+) |

TABLE 1-continued

| Compound No. | 1H-NMR(CDCl3): δ(ppm), J(Hz) | MS m/z |
|---|---|---|
|  | 7.25–7.44(3H, m), 7.54–7.58(2H, m). |  |
| Inter. 59 | 1.91–2.01(2H, m), 2.34(2H, t, J=7.4), 2.62–2.69(4H, m), 3.66 (3H, s), 4.09(2H, t, J=6.6), 6.88(1H, d, J=8.2), 7.11(1H, dd, J=8.2, 2.2), 7.17(1H, d, J=2.2), 7.29–7.44(3H, m), 7.52–7.56(2H, m). | 323 (M+) |
| 45 | (CD3OC): 1.86–1.96(2H, m), 2.31 (2H, t, J=7.4), 2.61–2.67 (4H, m), 4.19(2H, t, J=6.0), 6.98–7.01(1H, m), 7.12–7.15(2H, m), 7.22–7.37(3H, m), 7.45–7.49 (2H, m) | 328 (M+) |
| Inter. 60 | 1.24(3H, t, J=7.1), 1.91–2.06 (4H, m), 2.35(2H, t, J=7.4), 2.39 (2H, t, J=7.4), 2.63(2H, t, J=7.4), 2.66(3H, s), 3.97(2H, t, J=6.0), 4.10(2H, q, J=7.1), 6.89(1H, d, J=8.2), 7.09(1H, dd, J=8.2, 2.5), 7.14(1H, d, J=2.5), 7.28–7.42(3H, m), 7.49–7.53 (2H, m). | 384 (M+) |
| 46 | 1.94–2.05(4H, m), 2.37(2H, t, J=7.4), 2.44(2H, t, J=7.4), 2.66 (2H, t, J=7.4), 3.99(2H, t, J=6.0), 6.89(1H, d, J=8.2), 7.08–7.12(2H, m), 7.28–7.41 (3H, m), 7.48–7.51(2H, m). | 342 (M+) |
| Inter. 61 | 1.91–2.02(2H, m), 2.36(2H, t, J=7.4), 2.66(2H, t, J=7.4), 3.67(3H, s), 4.45(2H, s), 6.85–6.88(1H, m), 7.13–7.17(2H, m), 7.32–7.51(5H, m). | 328 (M+) |
| 47 | (DMSO-d6): 1.66–1.76(2H, m), 2.21(2H, t, J=7.4), 2.57(2H, t, J=7.4), 4.40(2H, s), 6.89–6.92 (1H, m), 7.10–7.15(4H, m), 7.30–7.44(3H, m), 7.56–7.59 (2H, m), 11.83, (1H, br). | 314 (MH+) |
| Inter. 62 | 1.90–2.00(2H, m), 2.35(2H, t, J=7.4), 2.63(2H, t, J=7.4), 2.88 (3H, s), 2.92(3H, s), 3.66(3H, s), 4.63(2H, s), 6.93(1H, d, J=8.2), 7.09(1H, dd, J=8.2, 2.2), 7.14(1H, d, J=2.2), 7.26–7.42(3H, m), 7.52–7.55(2H, m). | 356 (MH+) |
| 48 | 1.91–2.01(2H, m), 2.38(2H, t, J=7.4), 2.65(2H, t, J=7.4), 2.87(3H, s), 2.91(3H, s), 4.63(2H, s), 6.93(1H, d, J=8.2), 7.10 (1H, dd, J=8.2, 2.2), 7.13(1H, d, J=2.2), 7.26–7.41(3H, m), 7.50–7.54(2H, m). | 342 (MH+) |
| Inter. 63 | 0.98(3H, t, J=7.1), 1.09(3H, t, J=7.1), 1.90–2.00(2H, m), 2.35 (2H, t, J=7.1), 2.63(2H, t, J=7.1), 3.21(2H, q, J=7.1), 3.35 (2H, q, J=7.1), 3.66(3H, s), 4.60 (2H, s), 6.92(1H, d, J=8.2), 7.09(1H, dd, J=8.2, 2.2), 7.14 (1H, d, J=2.2), 7.27–7.41(3H, m), 7.52–7.56(2H, m). | 384 (MH+) |
| 49 | 0.97(3H, t, J=7.1), 1.09(3H, t, J=7.1), 1.91–2.01(2H, m), 2.38 (2H, t, J=7.1), 2.65(2H, t, J=7.1), 3.21(2H, q, J=7.1), 3.35 (2H, q, J=7.1), 4.60(2H, s) 6.92(1H, d, J=8.2), 7.09(1H, dd, J=8.2, 2.2), 7.14(1H, d, J=2.2), 7.26–7.41(3H, m), 7.52–7.55(2H, m). | 370 (MH+) |
| Inter. 64 | 0.75(2H, t, J=7.4), 1.14–1.28 (2H, m), 1.39–1.49(2H, m), 1.94–2.05(2H, m), 2.38(2H, t, J=7.4), 2.70(2H, t, J=7.4), 3.57 (2H, t, J=6.3), 3.68(3H, s), 7.34–7.47(4H, m), 7.50–7.56(3H, m). | 372 (MH+) |
| 50 | 0.75(3H, t, J=7.4), 1.13–1.26 (2H, m), 1.39–1.49(2H, m), 1.95–2.05(2H, m), 2.43(2H, t, J=7.4), 2.73(2H, t, J=7.4), 3.57 (2H, t, J=6.3), 7.35–7.47(4H, m), 7.51–7.55(3H, m). | 358 (MH+) |
| Inter. 65 | 0.78(3H, t, J=7.4), 1.19–1.32 (2H, m), 1.41–1.51(2H, m), 1.57 (1H, br), 1.89–1.99(2H, m), 2.35(2H, t, J=7.4), 2.56(2H, t, J=7.4), 3.43(2H, t, J=6.3), 3.66 (3H, s), 3.92(1H, br), 6.54(1H, d, J=2.2), 6.57(1H, d, J=2.2), 7.26–7.42(3H, m), 7.54–7.58 (2H, m). | 341 (M+) |
| Inter. 66 | 0.79 & 0.81(3H(1:2), each t, J=7.4), 1.18–1.29(2H, m), 1.31–1.46(2H, m), 1.92–2.03(2, m), 2.33–2.40(2H, m), 2.65(2H, t, J=7.4), 3.40 & 3.42(2H(1:2), each t, J=6.3), 3.67 & 3.68(3H(2:1), each s), 6.91 & 6.95(1H(2:1), each d, J=1.9), 7.32–7.44(3H, m), 7.51–7.56(2H, m), 7.79 (1/3H, br), 7.92(2/3, br), 7.03 & 8.22(1H(1:2), d, J=1.9), 8.49(2/3H, d, J=1.6), 8.83(1/3H, d, J=11.5). | 369 (M+) |
| 51 | 0.75 & 0.79(3H(1:2), each t, J=7.4), 1.16–1.31(2H, m), 1.40–1.53(2H, m), 1.94–2.04(2, m), 2.36–2.44(2H, m), 2.68(2H, t, J=7.4), 3.40 & 3.42(2H(1:2), each t, J=6.3), 6.91 & 6.96(1H(2:1), each d, J=1.9), 7.30–7.44(3H, m), 7.51–7.57(2H, m), 7.96 (2/3H, br), 8.14(1/3, br), 7.03 & 8.22(1H(1:2), d, J=1.9), 8.50(2/3H, d, J=1.6), 8.82 (1/3H, d, J=11.5). | 355 (M+) |
| Inter. 67 | 0.82(2H, t, J=7.4), 1.24–1.37 (2H, m), 1.43–1.53(2H, m), 1.92–2.03(2H, m), 2.21(3H, s), 2.36(2H, t, J=7.4), 2.65(2H, t, J=7.4), 3.41(2H, t, J=6.3), 3.66(3H, s), 6.87(1H, d, J=2.2), 7.30–7.44(3H, m), 7.50–7.55 (2H, m), 7.94(1H, br), 8.20(1H, d, J=2.2). | 384 (MH+) |
| 52 | 0.82(2H, t, J=7.4), 1.24–1.37 (2H, m), 1.43–1.53(2H, m), 1.93–2.03(2H, m), 2.21(3H, s), 2.39 (2H, t, J=7.4), 2.67(2H, t, J=7.4), 3.41(2H, t, J=6.3), 6.87 (1H, d, J=2.2), 7.30–7.44(3H, m), 7.50–7.55(2H, m), 7.96(1H, br), 8.19(1H, d, J=2.2). | 370 (MH+) |
| Inter. 68 | 0.79(2H, t, J=7.4), 1.17–1.30 (2H, m), 1.42–1.52(2H, m), 1.92–2.02(2H, m), 2.36(2H, t, J=7.4), 2.65(2H, t, J=7.4), 3.09(3H, s), 3.41(2H, t, J=6.3), 3.67 (3H, s), 6.91(1H, d, J=1.9), 7.03(1H, br), 7.33–7.46(4H, m), 7.50–7.55(2H, m). | 419 (M+) |
| 53 | 0.78(2H, t, J=7.4), 1.17–1.30 (2H, m), 1.42–1.52(2H, m), 1.93–2.03(2H, m), 2.41(2H, t, J=7.4), 2.67(2H, t, J=7.4), 3.09(3H, s), 2.67(2H, t, J=7.4), 3.09(3H, s), 3.41(2H, t, J=6.3), 6.91 (1H, d, J=1.9), 7.05(1H, br), 7.33–7.54(6H, m). | 405 (M+) |
| Inter. | 3.00(3H, s), 3.89(3H, s), 4.84 | 244 |

TABLE 1-continued

| Compound No. | 1H-NMR(CDCl3): δ(ppm), J(Hz) | MS m/z |
|---|---|---|
| 69 | (2H, s), 6.91–6.97(2H, m), 7.13 (1H, t, J=8.0), 7.28–7.42(3H, m), 7.52–7.56(2H, m). | (M+) |
| Inter. 70 | 3.95(3H, s), 5.85(1H, s), 6.86–7.00(3H, m), 7.31–7.46(3H, m), 7.60–7.63(2H, m). | 201 (MH+) |
| Inter. 71 | 0.74(3H, t, J=7.4), 1.14–1.28 (2H, m), 1.42–1.52(2H, m), 3.66 (2H, t, J=6.6), 3.90(3H, s),6.91 (1H, dd, J=8.0, 1.6), 6.95(1H, dd, J=8.0, 1.6), 7.10(1H, t, J=8.0), 7.29–7.42(3H, m), 7.53–7.57(2H, m). | 256 (M+) |
| Inter. 72 | 0.75(3H, t, J=7.4), 1.14–1.28 (2H, m), 1.43–1.53(2H, m), 2.77 (2H, t, J=6.6), 3.32(2H, t, J=6.6), 3.71(3H, s), 3.76(2H, t, J=6.6), 3.94(3H, s), 7.33–7.45 (3H, m), 7.51–7.61(4H, m). | 371 (MH+) |
| Inter. 73 | 0.74(3H, t, J=7.4), 1.13–1.27 (2H, m), 1.41–1.51(2H, m), 1.93—2.03(2H, m), 2.36(2H, t, J=7.4), 2.64(2H, t, J=7.4), 3.62(2H, t, J=6.6), 3.67(3H, s), 3.88 (3H, s), 6.72(1H, d, J=2.2), 6.76(1H, d, J=2.2), 7.28–7.41 (3H, m), 7.52–7.56(2H, m). | 357 (MH+) |
| 54 | 0.74(3H, t, J=7.4), 1.13–1.27 (2H, m), 1.41–1.51(2H, m), 1.94–2.04(2H, m), 2.42(2H, t, J=7.4), 2.67(2H, t, J=7.4), 3.62(2H, t, J=6.6), 3.88(3H, s), 6.72 (1H, d, J=2.2), 6.76(1H, d, J=2.2), 7.29–7.41(3H, m), 7.51–7.55(2H, m). | 342 (M+) |
| 55 | 0.90(3H, t, J=7.4), 1.34–1.47 (2H, m), 1.65–1.73(2H, m), 1.92–2.02(2H, m), 2.24(2Ht, J=7.4), 2.66(2H, t, J=7.4), 3.93(2H, t, J=6.3), 5.37(2H, br), 6.90 (1H, d, J=8.2), 7.10(1H, dd, J=8.2, 2.2), 7.14(1H, d, J=2.2), 7.26–7.42(3H, m), 7.51–7.56 (2H, m). | 311 (M+) |
| 56 | (DMSO-d6: 1.72–1.82(2H, m), 2.06(2H, t, J=7.4), 2.54(2H, t, J=7.4), 4.40(2H, s), 6.72(2H, br), 6.91(1H, d, J=9.0), 7.12–7.15(4H, m), 7.29–7.46 (3H, m), 7.57–7.60(2H, m). | 313 (MH+) |
| 57 | (CD3OD): 1.86–2.01(4H, m), 2.23 (2H, t, J=7.4), 2.28(2H, t, J=7.4), 2.63(2H, t, J=7.4, 3.96(2H, t, J=6.6), 4.88(4H, br), 6.95–6.99(1H, m), 7.11–7.14 (2H, m), 7.25–7.40(3H, m), 7.48–7.50(2H, m). | 341 (MH+) |
| Inter. 74 | 1.83–1.87(4H, m), 1.91–2.01 (2H, m), 2.35(2H, t, J=7.4), 2.64(2H, t, J=7.4), 3.48(2H, t, J=6.6), 3.66(3H, s), 3.96(2H, t, J=5.5), 6.89(1H, d, J=8.2), 7.10 (1H, dd, J=2.2, 8.2), 7.14(1H, d, J=2.2), 7.28–7.42(3H, m), 7.49–7.52(2H, m). | 360 (M+) |
| 58 | 1.82–1.86(4H, m), 1.91–2.01 (2H, m), 2.39(2H, t, J=7.4), 2.65 (2H, t, J=7.4), 3.48(2H, t, J=6.6), 3.95(2H, t, J=5.5), 6.89 (1H, d, J=8.2), 7.10(1H, dd, J=2.2, 8.2), 7.14(1H, d, J=2.2), 7.28–7.41(3H, m), 7.49–7.52 (2H, m). | 346 (M+) |
| Inter. 75 | 1.48(3H, d, J=6.6), 1.71–2.10 (4H, m), 2.35(2H, t, J=7.4), 2.64(2H, t, J=7.4), 3.66(3H, s), 4.03–4.19(3H, m), 6.93(1H, d, J=8.2), 7.09–7.14(2H, m), 7.28–7.42(3H, m), 7.47–7.56(2H, m). | 360 (M+) |
| 59 | 1.47(3H, d, J=6.6), 1.91–2.16 (4H, m, 2.39(2H, t, J=7.4), 2.65(2H, t, J=7.4), 4.02–4.18 (3H, m), 6.92(1H, d, J=8.2), 7.09–7.14(2H, m), 7.28–7.41(3H, m), 7.49–7.55(2H, m). | 346 (M+) |
| Inter. 76 | 181–201(6H, m), 2.35(2H, t, J=7.4), 2.63(2H, t, J=7.4), 3.35 (2H, t, J=6.6), 3.66(3H, s), 3.95(2H, t, J=6.0), 6.89(1H, d, J=8.2), 7.10(1H, dd, J=2.2, 8.2), 7.14(1H, d, J=2.2), 7.28–7.42(3H, m), 7.48–7.52 (2H, m). | 405 (MH+) |
| 60 | 1.72–2.02(6H, m), 2.39(2H, t, J=7.4), 2.66(2H, t, J=7.4), 3.35 (2H, t, J=6.6), 3.95(2H, t, J=5.8), 6.89(1H, d, J=8.2), 7.10 (1H, dd, J=2.2, 8.2), 7.14 (1H, d, J=2.2), 7.28–7.42 (3H, m), 7.47–7.54(2H, m). | 390 (m+) |
| Inter. 77 | 1.89–2.01(4H, m), 2.05–2.21 (2H, m), 2.35(2H, t, J=7.4), 2.64 (2H, t, J=7.4), 3.66(3H, s), 3.97(2H, t, J=6.0), 6.88(1H, d, J=8.2), 7.11(1H, dd, J=2.2, 8.2), 7.15(1H, d, J=2.2), 7.29–7.43 (3H, m), 7.47–7.51(2H, m). | 380 (M+) |
| 61 | 1.89–2.02(4H, m), 2.05–2.21 (2H, m), 2.39(2H, t, J=7.4), 2.66(2H, t, J=7.4), 3.97(2H, t, J=6.0), 6.88(1H, d, J=8.2), 7.11 (1H, dd, J=2.2, 8.2), 7.15(1H, d, J=2.2), 7.29–7.43(3H, m), 7.47–7.51(2H, m). | 366 (M+) |

What is claimed is:

1. A compound of the general formula (I) or salt thereof:

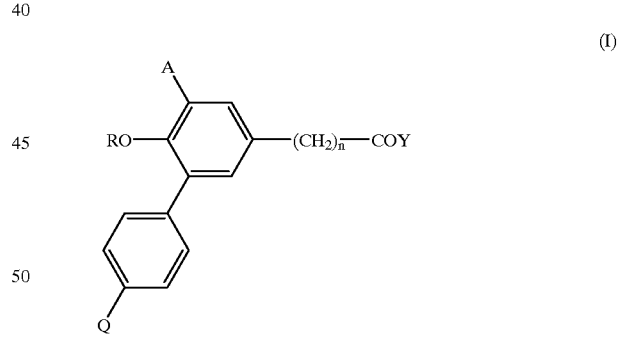

(I)

wherein n=2 or 3;

R=straight or branched $C_{1-4}$ saturated alkyl optionally substituted by hydroxy, oxygen or halogen; cyclopentyl, cyclohexyl, cyclopentylmethyl, cyclohexylmethyl or $(CH2)_mW$; m=1–3; W=carboxy or $CONR^1R^2$; $R^1$, $R^2$=are together or each separately hydrogen or $C_{1-4}$ lower alkyl; Y=hydroxy or amino; A=hydrogen, hydroxy, methoxy, nitro or NHZ; Z=$COR^3$ or $SO_2R^4$; $R^3$=hydrogen, $C_{1-4}$ saturated alkyl optionally substituted by hydroxy or halogen or $NR^5_2$; $R^4$=$C_{1-4}$ saturated alkyl optionally substituted by halogen or N $R^6_2$; $R^5$, $R^6$ hydrogen or $C_{1-4}$ lower alkyl; Q=hydrogen, hydroxy, methoxy.

2. The compound or salt thereof according to claim 1, wherein R in the general formula (I) is n-butyl, cyclohexylmethyl, carboxymethyl or carbamoylmethyl.

3. The compound or salt thereof according to claim 1, wherein the compound represented by the general formula (I) is selected from the group consisting of
3-(2-butoxy-1,1'-biphenyl-5-yl)propionic acid;
3-(2-isobutoxy-1,1'-biphenyl-5-yl)propionic acid;
3-(2-pentyloxy-1,1'-biphenyl-5-yl)propionic acid;
3-(2-cyclopentyloxy-1,1'-biphenyl-5-yl)propionic acid;
3-(2-cyclohexyloxy-1,1'-biphenyl-5-yl)propionic acid;
3-(2-cyclopentylmethyloxy-1,1'-biphenyl-5-yl)propionic acid;
3-(2-cyclohexylmethyloxy-1,1'-biphenyl-5-yl)propionic acid;
3-[2-(2-hydroxybutyloxy)-1,1'-biphenyl-5-yl]propionic acid;
3-[2-(2-oxobutyloxy)-1,1'-biphenyl-5-yl]propionic acid;
3-(2-carboxymethyloxy-1,1'-biphenyl-5-yl)propionic acid;
3-(2-carbamoylmethyloxy-1,1'-biphenyl-5-yl)propionic acid;
3-(2-butoxy-3-nitro-1,1'-biphenyl-5-yl)propionic acid;
3-(3-acetylamino-2-butoxy-1,1'-biphenyl-5-yl)propionic acid;
3-(2-butoxy-3-methylsulfonylamino-1,1'-biphenyl-5-yl)propionic acid;
3-(3-acetylamino-2-cyclohexylmethyloxy-1,1'-biphenyl-5-yl)propionic acid;
3-(2-cyclohexylmethyloxy-3-methylsulfonylamino-1,1'-biphenyl-5-yl)propionic acid;
3-(2-cyclohexylmethyloxy-3-hydroxyacetylamino-1,1'-biphenyl-5-yl)propionic acid;
3-[2-cyclohexylmethyloxy-3-(N,N-dimethylcarbamoylamino)-1,1'-biphenyl-5-yl]propionic acid;
3-[2-cyclohexylmethyloxy-3-(N,N-dimethylsulfamoylamino)-1,1'-biphenyl-5-yl]propionic acid;
3-(3-carbamoylamino-2-cyclohexylmethyloxy-1,1'-biphenyl-5-yl)propionic acid;
3-(2-cyclohexylmethyloxy-3-methoxy-1,1'-biphenyl-5-yl)propionic acid;
3-(2-cyclohexylmethyloxy-3-hydroxy-1,1'-biphenyl-5-yl)propionic acid;
3-(2-cyclohexylmethyloxy-4'-hydroxy-1,1'-biphenyl-5-yl)propionic acid;
3-(2-cyclohexylmethyloxy-4'-methoxy-1,1'-biphenyl-5-yl)propionic acid;
3-(2-cyclohexylmethyloxy-1,1'-biphenyl-5-yl)propionamide;
4-(2-butoxy-1,1'-biphenyl-5-yl)butyric acid;
4-(2-isobutoxy-1,1'-biphenyl-5-yl)butyric acid;
4-[2-(1-methylpropyloxy)-1,1'-biphenyl-5-yl]butyric acid;
4-(2-pentyloxy-1,1'-biphenyl-5-yl)butyric acid;
4-[2-(1-methylbutyloxy)-1,1'-biphenyl-5-yl]butyric acid;
4-[2-(2-methylbutyloxy)-1,1'-biphenyl-5-yl]butyric acid;
4-(2-isopentyloxy-1,1'-biphenyl-5-yl)butyric acid;
4-(2-cyclopentyloxy-1,1'-biphenyl-5-yl)butyric acid;
4-(2-cyclohexyloxy-1,1'-biphenyl-5-yl)butyric acid;
4-(2-cyclopentylmethyloxy-1,1'-biphenyl-5-yl)butyric acid;
4-(2-cyclohexylmethyloxy-1,1'-biphenyl-5-yl)butyric acid;
4-[2-(4-hydroxybutyloxy)-1,1'-biphenyl-5-yl]butyric acid;
4-[2-(3-hydroxybutyloxy)-1,1'-biphenyl-5-yl]butyric acid;
4-[2-(2-hydroxybutyloxy)-1,1'-biphenyl-5-yl]butyric acid;
4-(2-carboxymethyloxy-1,1'-biphenyl-5-yl)butyric acid;
4-[2-(2-carboxyethyloxy)-1,1'-biphenyl-5-yl]butyric acid;
4-[2-(3-carboxypropyloxy)-1,1'-biphenyl-5-yl]butyric acid;
4-(2-carbamoylmethyloxy-1,1'-biphenyl-5-yl)butyric acid;
4-[2-(N,N-dimethylcarbamoylmethyloxy)-1,1'-biphenyl-5-yl]butyric acid;
4-[2-(N,N-diethylcarbamoylmethyloxy)-1,1'-biphenyl-5-yl]butyric acid;
4-(2-butoxy-3-nitro-1,1'-biphenyl-5-yl)butyric acid;
4-(2-butoxy-3-formylamino-1,1'-biphenyl-5-yl)butyric acid;
4-(3-acetylamino-2-butoxy-1,1'-biphenyl-5-yl)butyric acid;
4-(2-butoxy-3-methylsulfonylamino-1,1'-biphenyl-5-yl)butyric acid;
4-(2-butoxy-3-methoxy-1,1'-biphenyl-5-yl)butyric acid;
4-(2-butoxy-1,1'-biphenyl-5-yl)butyramide;
4-(2-carbamoylmethyloxy-1,1'-biphenyl-5-yl)butyramide;
4-[2-(3-carbamoylpropyloxy)-1,1'-biphenyl-5-yl]butyramide;
4-[2-(4-chlorobutyloxy)-1,1'-biphenyl-5-yl]butyric acid;
4-[2-(3-chlorobutyloxy)-1,1'-biphenyl-5-yl]butyric acid;
4-[2-(4-bromobutyloxy)-1,1'-biphenyl-5-yl]butyric acid and
4-[2-(4,4,4-trifluorobutyloxy)-1,1'-biphenyl-5-yl]butyric acid.

4. A pharmaceutical composition comprising at least one of compounds or pharmacologically acceptable salt thereof according to claim 1 and a pharmaceutically acceptable carrier.

5. The pharmaceutical composition according to claim 4 wherein the pharmaceutical composition is IgE production suppressor or agent for prevention or treatment of allergic disease involved in IgE antibody.

6. The pharmaceutical composition according to claim 4 wherein the pharmaceutical composition is agent for treatment or prevention of bronchial asthma, allergic rhinitis, atopic dermatitis or allergic conjunctivitis.

* * * * *